(12) United States Patent
Tseng et al.

(10) Patent No.: US 7,494,802 B2
(45) Date of Patent: Feb. 24, 2009

(54) AMNIOTIC MEMBRANE COVERING FOR A TISSUE SURFACE AND DEVICES FACILITATING FASTENING OF MEMBRANES

(75) Inventors: Scheffer C. G. Tseng, Pinecrest, FL (US); Helga Sandoval, Charleston, SC (US); William G. Lee, Sunny Isles Beach, FL (US)

(73) Assignee: TissueTech, Inc., Miami, FL (US)

( * ) Notice: Subject to any disclaimer, the term of this patent is extended or adjusted under 35 U.S.C. 154(b) by 782 days.

(21) Appl. No.: 10/472,117

(22) PCT Filed: Mar. 14, 2003

(86) PCT No.: PCT/US03/07853

§ 371 (c)(1), (2), (4) Date: Apr. 19, 2004

(87) PCT Pub. No.: WO03/077794

PCT Pub. Date: Sep. 25, 2003

(65) Prior Publication Data

US 2004/0181240 A1    Sep. 16, 2004

Related U.S. Application Data

(60) Provisional application No. 60/365,356, filed on Mar. 14, 2002.

(51) Int. Cl.
*C12M 3/00* (2006.01)

(52) U.S. Cl. .................................. 435/285.1; 424/424

(58) Field of Classification Search ........................ None
See application file for complete search history.

(56) References Cited

U.S. PATENT DOCUMENTS

| | | | | |
|---|---|---|---|---|
| 4,184,360 | A | 1/1980 | Vadnay et al. | 73/28 |
| 4,686,190 | A * | 8/1987 | Cramer et al. | 435/287.1 |
| 5,474,490 | A * | 12/1995 | Allport | 451/58 |
| 5,665,596 | A | 9/1997 | Mussi | 435/373 |
| 5,932,205 | A | 8/1999 | Wang et al. | 424/78.04 |
| 6,143,315 | A | 11/2000 | Wang et al. | 424/427 |
| 6,152,142 | A | 11/2000 | Tseng | 128/898 |
| 6,162,193 | A | 12/2000 | Ekberg | 604/22 |
| 6,254,637 | B1 | 7/2001 | Lee et al. | 623/5.14 |
| 6,326,019 | B1 | 12/2001 | Tseng | 424/424 |

OTHER PUBLICATIONS

Meller et al., "Amniotic Membrane Transplantation For Symptomatic Conjunctivochalasis Refractory To Medical Treatments," *Cornea* 19(6): 796-803, 2000.

Chen, et al., "Amniotic Membrane Transplantation For Severe Neurotrophic Corneal Ulcers," *Br J Ophthalmol* 84: 826-833, 2000.

Shimazaki, et al., "Transplantation of amniotic membrane and limbal autograft for patients with recurrent pterygium associated with symblepharon," *Br J Ophthalmol* 82: 235-240, 1998.

Shimazaki, et al., "Amniotic Membrane Transplantation for Ocular Surface reconstruction in patients with Chemical and Thermal Burns," *Ophthalmol* 104 (12): 2068-2076, 1997.

Kim JC, Tseng SCG. Transplantation of preserved human amniotic membrane for surface reconstruction in severely damaged rabbit corneas. *Cornea* 1995;14:473-84.

Dua HS, Azuara-Blanco A. Amniotic membrane transplantation. *Br J Ophthalmol* 1999;83:748-52.

Kruse FE, et al. Cryoperserved human amniotic membrane for ocular surface reconstruction. Graefe's *Arch Clin Exp Ophthalmol* 2000;238 :68-75.

Trelford JD, et al, The amnion in surgery, past and present *Am J Obstet Gynecol* 1979:134-833-45.

de Rotth A., Plastic repair of conjunctival defects with fetal membrane. *Arch Ophthalmol* 1940;23:522-5.

Koizumi N, et al., Growth factor mRNA and protein in preserved human preserved human amniotic membrane. *Curr Eye Res*; 20 (3):173-7 2000.

Hao Y, et al. Identification of antiangiogenic and antiinflammatory proteins in human amniotic membrane. *Cornea*;19 (3):348-52 2000.

International Search Report dated Feb. 26, 2004, for PCT/US03/07853.

* cited by examiner

*Primary Examiner*—James S Ketter
(74) *Attorney, Agent, or Firm*—Wilson Sonsini Goodrich & Rosati

(57) ABSTRACT

The present invention relates to a biopolymer covering for a tissue surface including, for example, a dressing, a bandage, a drape such as a bandage contact lens, a composition or covering to protect tissue, a covering to prevent adhesions, to exclude bacteria, to inhibit bacterial activity, or to promote healing or growth of tissue. An example of such a composition is an amniotic membrane covering for an ocular surface. Use of a covering for a tissue surface according to the invention eliminates the need for suturing. The invention also includes devices facilitating the fastening of a membrane to a support, culture inserts, compositions, methods, and kits for making and using coverings for a tissue surface and culture inserts. Compositions according to the invention may include cells grown on a membrane or attached to a membrane, and such compositions may be used as scaffolds for tissue engineering or tissue grafts. A method of preparing and using an amniotic membrane covering for a tissue surface as a controlled release drug delivery vehicle is also disclosed.

109 Claims, 26 Drawing Sheets

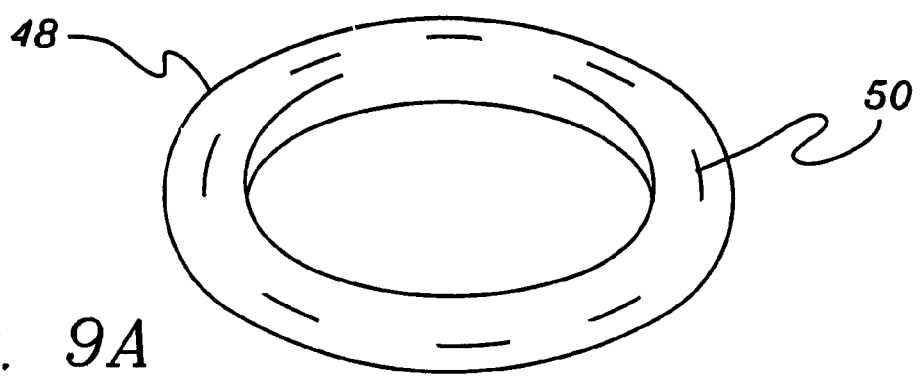
fig. 9A
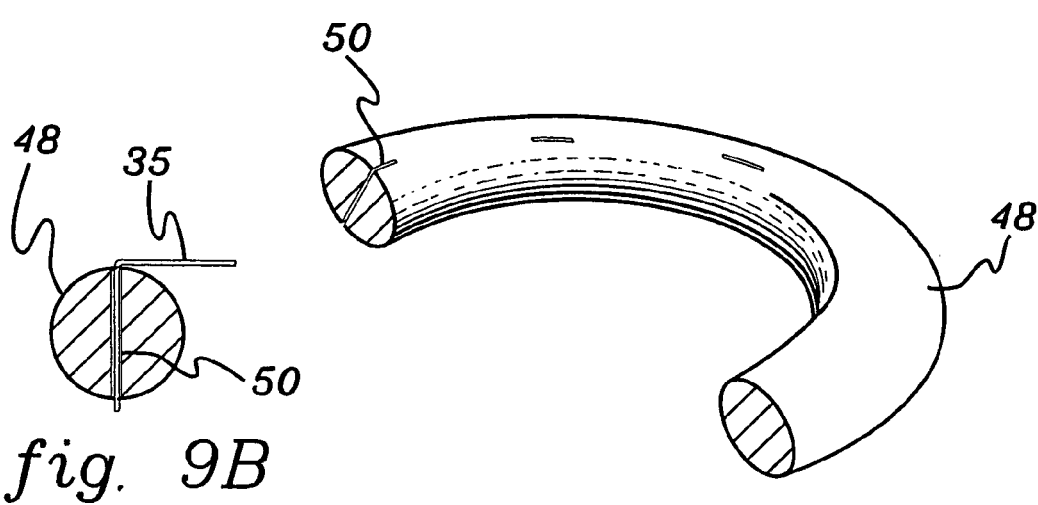
fig. 9B
fig. 9C
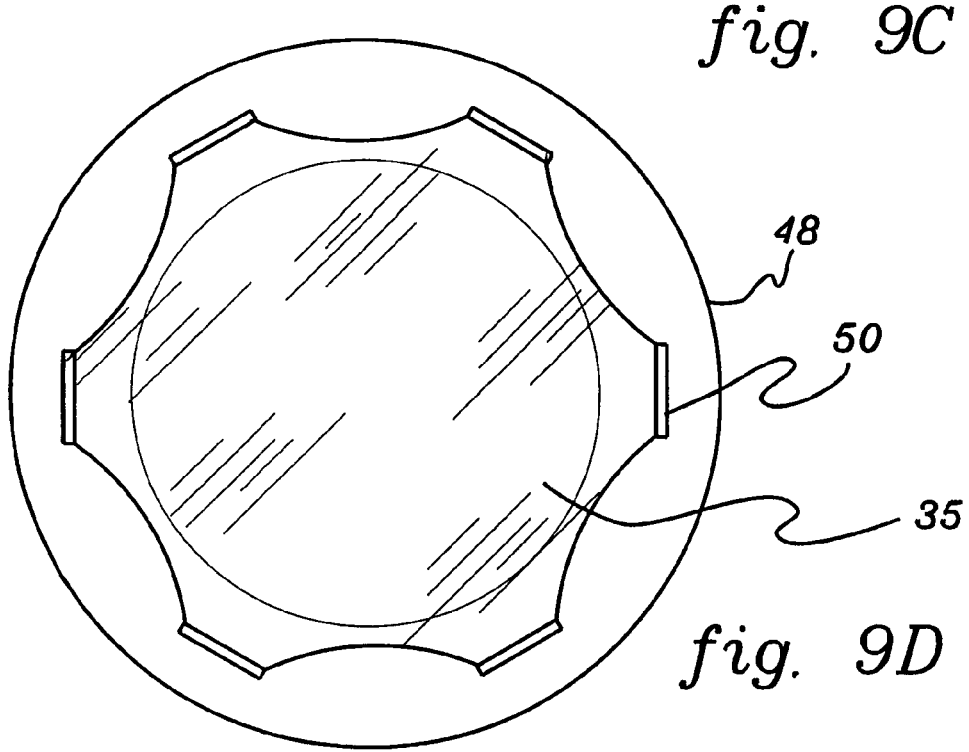
fig. 9D

AMNIOTIC MEMBRANE COVERING FOR A TISSUE SURFACE AND DEVICES FACILITATING FASTENING OF MEMBRANES

RELATED APPLICATION

This application claims the benefit of U.S. Provisional Application No. 60/365,356 filed on Mar. 14, 2002, the teachings of which are incorporated herein by reference in their entirety.

GOVERNMENT SUPPORT

The invention was supported, in whole or in part, by grant number EY06819 from National Institutes of Health. The Government has certain rights in the invention.

BACKGROUND OF THE INVENTION

Amniotic compositions, such as amniotic membrane and extracts from amniotic membrane obtained from amniotic tissue derived from mammals, such as humans, pigs, or horses, include biological growth factors. Amniotic membrane is a biological membrane that lines the inner surface of the amniotic cavity and comprises a simple, cuboidal epithelium, a thick basement membrane, and an avascular mesenchymal layer containing hyaluronic acid. Amniotic compositions are known to reduce inflammation, fibrovascular ingrowth, and to facilitate epithelialization in animal models. Amniotic membrane is believed to play a role in the scarless wound healing process in a fetus (Tseng, S.-C.-G., et al., "Suppression of Transforming Growth Factor-Beta Isoforms, TGF-β Receptor Type II, and Myofibroblast Differentiation in Cultured Human Corneal and Limbal Fibroblasts by Amniotic Membrane Matrix," *J. Cell. Physiol.*, 179: 325-335 (1999)).

Fetal membrane, including the amnion (amniotic membrane) and chorion has been used in surgeries, documented as early as 1910 with the use by Davis on burned and ulcerated skin (Davis, J. W., "Skin Transplantation With a Review of 550 cases at the Johns Hopkins Hospital," *Johns Hopkins Med. J*, 15: 307 (1910). Beginning in 1973, Trelford and associates reported other uses of amnion, including, for example, a use to replace pelvic peritoneum, use on full-thickness skin wounds, use to cover exposed deep surfaces in pedicle graft procedures, use as a graft over the surgical defect of total glossectomy, and in the prevention of meningocerebral adhesions following head injury (See Trelford and Trelford-Sauder, "The Amnion in Surgery, Past and Present," *Am. J. Obstet. Gynecol.*, 134: 833 (1979)).

Amniotic compositions have been used for treatment of injured corneal tissue. For example, amniotic membrane transplantation has been used for ocular surface reconstruction for acute chemical and thermal burns (Kim, J.-C., and Tseng, S.-C.-G., "A Transplantation of Preserved Human Amniotic Membrane for Surface Reconstruction in Severely Damaged Rabbit Corneas," *Cornea* 14(5): 473-484 (1995)). The surgical technique of suturing is used to secure the transplanted amniotic membrane to a tissue surface, either internally or externally (Id. at 475). For example, in the case of injured corneal tissue, whether amniotic membrane is used is used as a permanent graft or as a temporary patch, sutures are used to secure the membrane on a patient's eye at a major operating room.

Although, for example, amniotic membrane may be sutured to an ocular surface, it may not be possible to bring patients under critical care to the operating room for the needed eye surgery. Thus, a need exists for a device to facilitate the use of amniotic membrane for treatment of injured or diseased tissue, such as, for example, chemically or thermally burned corneal tissue, without the requirement of suturing the membrane in place.

Suturing has also been used to fasten amniotic membrane to a culture insert, such as a silicone ring, for use in culturing cells. The making of culture inserts by the suturing method, however, is time-consuming. Thus a need exists for an efficient method of making culture inserts.

SUMMARY OF THE INVENTION

The invention inter alia includes the following, alone or in combination. In one embodiment, amniotic membrane is fastened onto a device or support, that may be, for example, in the shape of a conformer to be fitted to cover a portion of the corneal surface, the corneal surface, or the entire ocular surface. The support may be ring-shaped. The support with amniotic membrane attached thereto may me used as a temporary patch to reduce inflammation and scarring, hence facilitating wound healing and restoring comfort and vision.

The present invention relates, in one aspect, to a method and an apparatus for fastening a membrane to a support, for example, a culture insert. The method includes the steps of contacting the membrane with the culture insert; positioning the membrane on the culture insert, thereby completely covering the culture insert with the membrane; placing a radially elastic band over the apex of a conical shaped expander having an apex, a base, and an outer surface of increasing diameter from the apex towards the base thereof, the base having a shoulder; placing the base of the expander in contact with a ring having a peripheral annular groove for receiving the band; urging the band in a direction from the apex of the expander over the outer surface of the expander towards the shoulder of the base of the expander, thereby causing the band to stretch and form a radially expanded state; urging the band over the shoulder of the expander and into the peripheral annular groove on the ring, thereby controllably releasing the band from the expander and attaching the band to the ring; contacting the ring having the band attached thereto with the membrane on the insert; and controllably releasing the band from the ring such that the band is translocated from the ring to the insert, thereby fastening the band over the membrane and fastening the membrane to the insert.

The invention inter alia also includes the following embodiments, alone or in combination. One embodiment of the method of the invention is carried out by use of an apparatus of the invention, an apparatus for urging a radially elastic band over the outer surface of the expander, the apparatus including a longitudinally extending cannula having a proximal end portion and a distal end portion, the cannula defining a bore extending longitudinally therethrough from the proximal end portion to the distal end portion, and fitting coaxially over the apex of the expander and radially expandable at the distal end portion. As such, an apparatus of the invention is used to frictionally engage a radially elastic band placed over the apex of a conical shaped expander having an apex, a base, and an outer surface of increasing diameter from the apex towards the base thereof, and to urge the band in a direction from the apex of the expander over the outer surface of the expander towards the base of the expander, thereby causing the band to stretch and form a radially expanded state.

Another embodiment of the invention is a method of fastening a membrane to a ring having an inner surface defining a hole and having at least one annular groove sized to receive an O-ring, the method including the steps of contacting the membrane to be fastened with the ring; positioning the membrane on the ring, thereby completely covering the ring with the membrane; and inserting the O-ring into the annular groove, thereby fastening the membrane to the ring. Accordingly, a composite of the invention is a culture insert including a ring having an inner surface defining a hole and having at least one annular groove sized to receive an O-ring; a membrane mounted to the ring, the membrane completely covering the ring; and the O-ring inserted in the annular groove to fasten the membrane to the ring during assembly.

Another embodiment of the invention is a method of fastening a membrane between an O-ring having an outer peripheral annular surface and a ring having an inner annular surface defining a hole and having at least one annular groove, the method including the steps of contacting the membrane to be fastened with the O-ring; positioning the membrane on the O-ring, thereby completely covering the O-ring with the membrane; wrapping the membrane over the outer peripheral annular surface of the O-ring to form a wrapped O-ring; and inserting the wrapped O-ring into the annular groove, thereby fastening the membrane between the O-ring and the ring.

A membrane fastened between two rings according to this embodiment of a method of the invention is a composite of the invention. Accordingly, a composite of the invention is a culture insert including an O-ring having an inner surface defining a hole and an outer peripheral annular surface; a membrane mounted to the O-ring, the membrane completely covering the O-ring and wrapped over the outer peripheral annular surface thereof to form a wrapped O-ring; and a ring having an inner annular surface defining a hole and having at least one annular groove sized to receive the wrapped O-ring; wherein the wrapped O-ring is positioned in the annular groove to fasten the membrane between the O-ring and the ring during assembly.

Another embodiment of the invention is a method of fastening a membrane between a first snap together ring and a second snap together ring, the first snap together ring including a surface comprising a plurality of spaced fastener posts, and the second snap together ring including a surface defining a plurality of spaced fastener post apertures, the method including the steps of contacting the membrane to be fastened with the surface of the first ring; positioning the membrane on the first ring, thereby completely covering the first ring with the membrane; positioning the second ring over the first ring for alignment of at least one of the spaced fastener posts with at least one of the spaced fastener post apertures; and lockingly engaging the first ring with the second ring, by inserting at least one of the posts in a fastener post aperture, thereby fastening the membrane between the first ring and the second ring.

Accordingly, a composite of the invention is a culture insert including a first snap together ring having a first surface; a plurality of spaced fastener posts located on the first surface; a second snap together ring having a second surface defining a plurality of spaced fastener post apertures thereon, wherein at least one of the apertures is spaced to align with a position of at least one of the posts when the two rings are matingly engaged during assembly; and a membrane fastened between the two snap together rings.

Another embodiment of the invention is a method of fastening a membrane to a ring having a peripheral annular surface, an inner annular surface, a top surface and a bottom surface, with at least one surface defining at least one cut slit thereon. The method includes the steps of contacting the membrane to be fastened with the ring; positioning the membrane on the top surface or the bottom surface of the ring, thereby covering the ring with the membrane; and inserting the membrane into the cut slit, thereby fastening the membrane to the ring.

Accordingly, a composite of the invention is a culture insert including a ring having a peripheral annular surface, an inner annular surface, a top surface and a bottom surface, with at least one surface defining at least one cut slit thereon; and a membrane positioned on the top surface or the bottom surface of the ring, the membrane covering the ring, and at least a portion of the membrane inserted into the cut slit to thereby fasten the membrane to the ring during assembly.

Another embodiment of the invention is a method of preparing a biopolymer covering for a tissue surface including the steps of contacting a biopolymer membrane with the surface of a first ring having an outer annular edge and an outside diameter sized to snap-fit within the inside diameter of a second ring having an inner annular edge; positioning the membrane on the first ring, thereby completely covering the first ring with the membrane and wrapping the membrane over the outer annular edge of the first ring; positioning the second ring over the first ring for coaxial alignment therewith; and lockingly engaging the first ring with the second ring, thereby fastening the membrane between the first ring and the second ring, and making a biopolymer covering for a tissue surface.

Accordingly, a composite of the invention is a tissue surface covering including a first ring having an outer annular edge and an outside diameter; a membrane completely covering the first ring, the membrane wrapped over the outer annular edge of the first ring; and a second ring having an inner annular edge and an inside diameter, the inside diameter of the second ring sized to snap-fit over the outside diameter of the first ring, and positioned over the first ring for coaxial alignment therewith; the membrane fastened between the first ring and the second ring by a locking engagement of the first ring with the second ring during assembly of the tissue surface covering.

Another embodiment of the invention is a method of preparing an amniotic membrane covering for a tissue surface including the steps of applying an adhesive composition to at least one surface of a support having an outside diameter; contacting the adhesive composition on the surface of the support with an amniotic membrane, the membrane having a surface with a diameter greater than the outside diameter of the support; positioning the support on the membrane so that the membrane can be folded inwardly over the support; and folding the membrane inwardly over the support such that the support is covered by the membrane, thereby making an amniotic membrane covering for a tissue surface.

Accordingly, a composite of the invention is an amniotic membrane covering for a tissue surface including a support having an outside diameter; an adhesive composition applied to at least one surface of the support; and an amniotic membrane in contact with the adhesive composition, the membrane having a surface with a diameter greater than the outside diameter of the support and folded inwardly over the support during assembly such that the support is covered by the membrane and secured to the membrane by the adhesive composition.

Another embodiment of the invention is a method of preparing an amniotic membrane covering for a tissue surface including the steps of positioning a support having an outside diameter on a center portion of an amniotic membrane having a surface with a diameter greater than the outside diameter of the support; applying an adhesive composition to a portion of the surface of the amniotic membrane that extends beyond the outside diameter of the support; and folding the amniotic membrane inwardly over the support such that the support is covered by the amniotic membrane, thereby making an amniotic membrane covering for a tissue surface.

Accordingly, a composite of the invention is an amniotic membrane covering for a tissue surface including a support having an outside diameter; an amniotic membrane having a surface with a diameter greater than the outside diameter of the support; and an adhesive composition applied to at least one surface of the membrane for securing the membrane to the support, the membrane folded inwardly over the support such that the support is contacted by the adhesive composition and is covered by the membrane during assembly of the amniotic membrane covering for a tissue surface.

Another embodiment of the invention is a method of preparing an amniotic membrane covering for a tissue surface including the steps of positioning a support having an outside diameter on a center portion of a stromal side of an amniotic membrane having a surface with a diameter greater than the outside diameter of the support; folding the amniotic membrane inwardly over the support such that the support is covered by the amniotic membrane to form a covered support; and allowing a portion of the stromal side of the folded membrane to adhere to another portion of the stromal side of the membrane, thereby holding the covered support in place and making an amniotic membrane covering for a tissue surface.

Accordingly, a composite of the invention is an amniotic membrane covering for a tissue surface including a support having an outside diameter; an amniotic membrane having a surface with a diameter greater than the outside diameter of the support, and having a stromal side; the support positioned on a center portion of the stromal side of the membrane, the membrane folded inwardly over the support during assembly such that the support is covered by the membrane, and a portion of the stromal side of the folded membrane adheres to another portion of the stromal side of the membrane, thereby holding the support in place.

Another embodiment of the invention is a kit comprising an apparatus of the invention for urging a radially elastic band over the outer surface of the expander; a conical shaped expander; an O-ring; a ring having an inner surface defining a hole and having at least one annular groove sized to receive the O-ring; and at least one membrane sized to completely cover the ring.

The present invention has many advantages. The devices and methods according to various embodiments of the invention facilitate the fastening of an elastic band or ring, placed over a membrane, to a support such as a culture insert or a covering for a tissue surface. The ring is applied to the support while the ring is in an expanded state, and the stored elastic forces in the ring apply a contracting force, thereby securing the membrane to the support. When heavy rings are used, considerable force is required to achieve expansion and the process is labor-intensive and time-consuming. Use of the method and apparatus of the invention to expand a ring and to apply the ring to a support facilitates the fastening of the ring to the support and the securing of a membrane to the support.

An amniotic membrane covering for a tissue surface according to an embodiment of the invention can be comprised of a support that is flexible or that is molded to fit the contour of a given tissue surface. For example, an amniotic membrane covering for a tissue surface can be molded to fit the contour of the ocular surface, and to cover a portion of the ocular surface or the entire ocular surface, to form a bandage for the eye.

After eye surgery or eye injury, instead of taping the upper eye lid shut over the eye, or suturing the upper and lower lids together over the eye, or suturing the amniotic membrane to the ocular surface, an amniotic membrane covering for an ocular tissue surface according to an embodiment of the invention can be placed between the eyelids and the cornea to function as a bandage contact lens. The amniotic membrane covering can protect the cornea, promote healing, eliminate the need for immobilizing the eye lids, eliminate the need for suturing, can readily be removed or replaced, and can serve as a controlled release drug delivery vehicle.

According to an embodiment of the invention, a covering for a tissue surface includes a support. Use of a support not only facilitates the insertion or placement of the covering on a tissue surface and the removal of the covering from the tissue surface, but also reduces the likelihood of tearing a fragile membrane attached thereto.

An amniotic membrane covering for a tissue surface can be molded to fit the contour of a tissue surface within the body, and can be implanted at a desired tissue site. The covering for a tissue surface can also be shaped to interface with a combination of an implanted tissue and the recipient's own body tissue, to facilitate the acceptance of the implanted tissue by the recipient's immune system by shielding or insulating the transplanted tissue from the recipient's immune cells.

Amniotic membrane transplantation, both by means of a permanent graft, for host cells to grow over or onto the membrane; and by means of a temporary patch, dressing, or bandage, is useful for a variety of ophthalmic indications, and is effective in facilitating epithelial wound healing, and reducing stromal inflammation, scarring and unwanted new blood vessel formation.

Thus, the invention includes a support with amniotic membrane attached thereto, for use as a temporary patch applied to an ocular surface inflicted with any of various diseases and insults. These include acute chemical burns of the ocular surface (10;11;18;26;27), which remain to be one of the most devastating and challenging ophthalmic emergencies. Chemical, especially alkali, burns result in severe inflammation, which frequently become relentless and chronic. As a result, granulation tissues mixed with necrosis invariably leads to prominent scarring. Scarring in the corneal surface will reduce vision, in the conjunctiva will cause motility restriction, and in the lids will cause exposure, mechanical micro-trauma (due to misdirected lashes and keratinization), or dryness.

Patients with life-threatening injuries often cannot undergo emergency surgery, for example the transplant of a graft of amniotic membrane, to treat chemical or thermal burns of the eye. The use of an amniotic membrane covering for an ocular surface, as a temporary patch, that is a dressing or bandage "contact lens" can be used as an emergency treatment. Because the amniotic membrane covering for an ocular surface is "sutureless," it will facilitate the ease of patient care (e.g., applicable in Intensive Care or Burn Units for patients who cannot be brought to the operating room for the needed surgery), and allow us to explore other clinical applications in the future. Further, it can be used in office practices to eliminate cumbersome and costly surgical facilities.

Conventional therapies with various medical treatments to suppress inflammation and encourage wound healing have a limited success. The majority of patients with chemical burns, worse than grade I severity, eventually face severe ocular surface failure in the later stage. Recently amniotic membrane transplantation as a temporary patch has been shown to reduce inflammation and scarring, hence facilitating wound healing and restoring comfort and vision (26).

Amniotic membrane as a temporary patch has also been successfully used to suppress inflammation, promote healing, and prevent scarring in patients suffering from Stevens Johnson syndrome or toxic epidermal necrolysis at the acute stage (36). Patients suffering from Stevens Johnson syndrome, if not fatal during the care at either the Intensive Care Unit or the Burn Unit, are frequently inflicted with a blinding disease because of the poor management of the ocular surface complication. This is because the surface breakdown is not promptly treated at the acute stage, while the patient is under critical care.

An amniotic membrane covering for a tissue surface according to an embodiment of the invention may also be used to reduce ocular pain and corneal haze for patients receiving excimer laser surgeries, and to improve the success of keratoprosthesis implantation.

The amniotic membrane suitable for use in an embodiment of the invention may be procured, processed and prepared according to the teachings of U.S. Pat. Nos. 6,152,142 and 6,326,019, the teachings of which are incorporated herein by reference in their entirety. The amniotic membranes suitable for use in an embodiment of the invention are commercially available under the trade name of AmnioGraft™, distributed by Bio-Tissue (Miami, Fla.).

The preserved amniotic membrane is devoid of viable allogeneic cells but retains its anti-inflammatory and anti-scarring effects. This novel method of preparation has been proven by others to devitalize all allogeneic cells (6), thus eliminating the potential side effect of allograft rejection, but preserving the properties of the amniotic membrane, that is, facilitating epithelialization, and reducing stromal inflammation, scarring and unwanted blood vessel formation that are inherently present in utero (2-5).

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

FIG. 9A is a perspective view of a ring (48) with cut slits (50) on the top surface thereof.

FIG. 9B is a cross-sectional view of a portion of ring (48) showing membrane (35) in slit (50).

FIG. 9C is a sectional view of a portion of ring (48).

FIG. 9D is a top plan view of ring (48), showing membrane (35) covering a portion of ring (48), the edge of membrane (35) inserted into slits (50).

DETAILED DESCRIPTION OF THE INVENTION

Figure 1A:
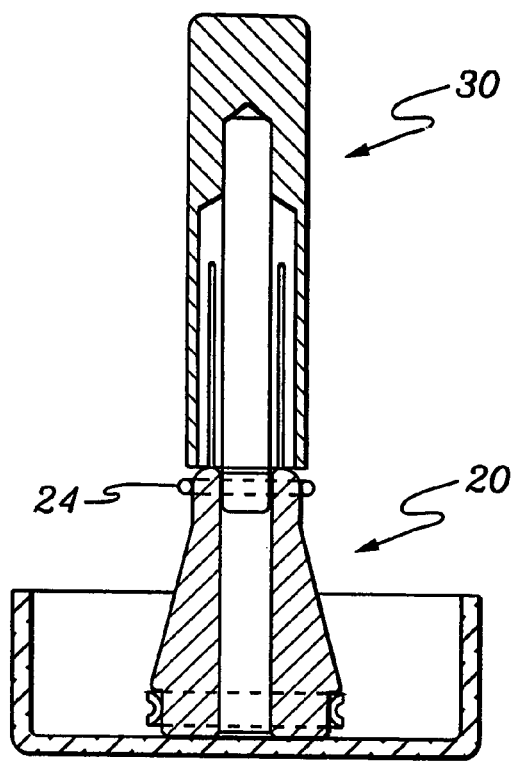
FIG. 1A is a partial transectional elevational view of an apparatus (30) for frictionally engaging a radially elastic band (24), showing apparatus (30) and band (24) positioned over the apex of a conical shaped expander (20), and the base of expander (20) in contact with a ring having a peripheral annular groove for receiving band (24).

A description of preferred embodiments of the invention follows. It will be understood that the particular embodiments of the invention are shown by way of illustration and not as limitations of the invention. At the outset, the invention is described in its broadest overall aspects, with a more detailed description following. The features and other details of the compositions and methods of the invention will be further pointed out in the claims.

The present invention is directed to an apparatus and methods for fastening a membrane to a support; culture inserts; and coverings for a tissue surface. As used herein, the term "membrane" includes those materials having a sheet-like structure formed from a biological matrix or a polymer matrix. Membranes suitable for use in an embodiment of the invention include, for example, biopolymer membranes. A "biopolymer," as the term is used herein, includes polymers that occur in a living system or that are derived from biological materials. Examples of biopolymers include, but are not limited to, amniotic membrane, polysaccharides and mucopolysaccharides such as hyaluronic acid and derivatives thereof, collagen and collagen derivatives. Amniotic membrane, as the term is used herein, is a biological membrane that lines the inner surface of the amniotic cavity and comprises a simple, cuboidal epithelium, a thick basement membrane, and an avascular mesenchymal layer containing hyaluronic acid. In general, a membrane suitable for use in an embodiment has a thickness of between about 0.001 mm and about 1 mm.

As the term is used herein, a "support" is a solid material in contact with a membrane or film. A support used in an embodiment is generally inert. The support helps form a membrane or film into a desired shape, or aids in the retention by the membrane or film of a particular shape. In one embodiment of the invention the membrane fastened to the support is a culture insert. Accordingly, as the term is used herein, a "culture insert" is a sheet or membrane to which at least one cell or at least one piece of tissue has been added, the sheet or membrane to be inserted or placed in a culture medium. According to an embodiment of the invention, a culture insert includes a support.

A "culture," as the term is used herein, refers to the cultivation or growth of cells, for example, tissue cells, in or on a nutrient medium. As is well known to those of skill in the art of cell or tissue culture, a cell culture is generally begun by removing cells or tissue from a human or other animal, dissociating the cells by treating them with an enzyme, and spreading a suspension of the resulting cells out on a flat surface, such as the bottom of a Petri dish. There the cells generally form a thin layer of cells called a "mono-layer" by producing glycoprotein-like material that causes the cells to adhere to the plastic or glass of the Petri dish. A layer of culture medium, containing nutrients suitable for cell growth, is then placed on top of the mono-layer, and the culture is incubated to promote the growth of the cells.

Any one of a number of types of cells may be expanded on a culture insert according to the invention. For example, the cells expanded on a culture insert of the invention, which may then be used to make an amniotic membrane covering for a tissue surface according to the invention, may be a type of cell used to generate an action of gene therapy.

Amniotic membrane, prepared according to U.S. Pat. No. 6,452,142 to Tseng, is an excellent substrate for expansion of epithelial stem cells. Additionally, an amniotic membrane covering for a tissue surface may include cells of at least one type that have been expanded on the amniotic membrane portion of the covering. A method for expansion of epithelial stem cells, limbal stem cells and limbal epithelial cells, taken from a healthy eye, is described in published PCT application No. WO 01/80760, the teachings of which are incorporated herein by reference in their entirety. WO 01/80760 teaches the use of amniotic membrane (Bio Tissue, Miami, Fla.), processed and preserved according to the method described in U.S. Pat. No. 6,452,142 to Tseng, the teachings of which are incorporated herein by reference in their entirety, for the expansion of cells.

In one embodiment of the invention, a solid support with fastened amniotic membrane with or without additional cryopreservation may be used as a substrate with the basement membrane surface facing up to culture a limbal explant with epithelial stem cells which will be placed at the center of the membrane with one drop of FBS (fetal bovine serum) overnight to allow adequate adhesion, and then cultured as described in detail below in a suitable medium.

Epithelial stem cells, limbal stem cells and limbal epithelial cells, taken from a healthy eye and expanded on amniotic membrane of a culture insert according to the invention may be used as therapeutic agents in contact with an amniotic membrane covering for a tissue surface placed in contact with an ocular surface, and may be used to treat a disease in which there is a stem cell or limbal epithelial cell deficiency. For example, an amniotic membrane covering for an ocular surface may include cultivated limbal epithelial stem cells and may be used as a corneal graft.

In one embodiment of the invention, a solid support with fastened amniotic membrane with or without additional cryopreservation may be used as a substrate with the basement membrane surface facing up to culture retinal pigment epithelial cells (RPE cells), as taught in U.S. Provisional Application Serial No. 60/415,986.

The expanded RPE cells grown on a culture insert according to the invention may be transplanted to the subretinal space according to a method taught in U.S. Provisional Application No. 60/415,986. The teachings of U.S. Provisional Application No. 60/415,986 are incorporated herein by reference in their entirety. The expanded RPE cells on an amniotic membrane may be used to make a biomolecular covering for a tissue surface.

Instead of a mono-layer, pieces of organs or whole organs may be cultured. In some instances, pieces of tissue or cells removed from an animal are placed on a sheet or membrane, which may be stretched like the head of a drum. Then the sheet or membrane, referred to as a "culture insert," is placed in a container, such as a Petri dish, covered with a culture medium, and incubated. Cells cultured in this manner tend to grow on the sheet or membrane, rather than on the bottom of the container. Uses of the cultured cells and the membrane include tissue engineering for grafts.

In one embodiment the membrane fastened to the support is a tissue covering. As used herein, the terms "tissue covering," "covering for a tissue surface," and "covering" have the same meaning and include, for example, a dressing, a bandage, a drape such as a bandage contact lens, a composition or covering to protect tissue, a covering to prevent adhesions, to exclude bacteria, to inhibit bacterial activity, or to promote healing or growth of tissue. As the term is used herein, "tissue" may include any collection of cells or integrated group of cells with a common structure and function, for example, skin cells, conjunctival tissue, corneal epithelial cells, bone tissue, liver tissue, or pancreatic tissue.

Figure 4A:
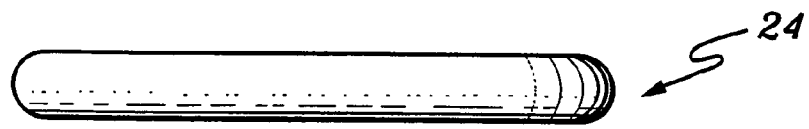
FIG. 4A depicts an elevational view of an O-ring (24).

Method and Device for Fastening a Membrane to a Support Using a Conical Expander In one embodiment of the method of the invention a membrane is positioned on a support, for example, a first ring, thereby completely covering the first ring with the membrane. As depicted in FIGS. 1A-1D and FIG. 2, a radially elastic band (24) is placed over the apex of a conical shaped expander (20) having an apex (27), a base (28), and an outer surface of increasing diameter from the apex towards the base thereof, the base having a shoulder (26). A conical shaped expander suitable for use in an embodiment is shown in FIGS. 1A-1D, and FIG. 2. The base (28) of the expander is placed in contact with a second ring having a peripheral annular groove for receiving the band. See, for example, FIGS. 4C and 4D, which show a support ring (22) having a peripheral annular groove (23). Band (24) is then biased in a direction from the apex (27) of the expander over the outer surface of the expander towards the shoulder (26) of the base (28) of the expander, thereby causing the band to stretch and form a radially expanded state. The band is further biased over the shoulder (26) of the expander and into the peripheral annular groove on the second ring, thereby controllably releasing the band from the expander and attaching the band to the second ring. The second ring having the band attached thereto is then contacted with the membrane on the first ring; and the band is controllably released from the second ring such that the band is translocated from the second ring to the first ring, thereby fastening the band over the membrane and fastening the membrane to the first ring.

In one embodiment of the invention the membrane comprises an amniotic membrane. Methods of preparing amniotic membrane suitable for use in an embodiment of the invention are well known in the art and are described, for example in U.S. Pat. Nos. 6,326,019 B1 and 6,152,142 to Tseng, the teachings of each of which are incorporated herein by reference in their entireties. Methods of preservation of amniotic membrane are also described in WO 01/08716 A1, the teachings of which are incorporated herein by reference in their entirety.

Amniotic membrane suitable for use in an embodiment of the invention is obtained from mammalian placenta, especially human placenta, from which the chorion has been separated. The amniotic membrane used in an embodiment may also be derived, for example, from an equine, a bovine, or an alpaca source. Amniotic membrane suitable for use in an embodiment of the invention generally includes an epithelial layer, a basement membrane, and a stroma, the combination of the three layers preferably having a total thickness of between about 0.05 mm to about 0.5 mm. Sheets of the amniotic membrane can be cut to size, mounted on filter paper, and stored in a storage solution. The storage solution comprises a culture medium and a hyperosmotic agent, wherein the hydration of the amniotic membrane is maintained. The membrane can be impregnated with therapeutic agents, prior to storage or prior to use.

In another embodiment of the method and compositions of the invention the membrane comprises a hyaluronan derivative or a collagen derivative. In another embodiment, the membrane is formed from a polycarbonate, polyethylene terephthalate, polyester or styrene-acrylonitrile material. In another embodiment, the membrane is a biopolymer membrane such as a hyaluronan derivative or a collagen derivative, wherein a biochemical extract from amniotic membrane or another amniotic composition is attached to the surface of the biopolymer membrane, or entrapped within the biopolymer membrane.

In one embodiment, the ring having a peripheral annular groove is comprised of a polymer material such as silicone or silicone foam. In another embodiment, the ring is comprised of polymethyl methacrylate, polytetrafluoroethylene, or polyurethane. In another embodiment the ring is comprised of a material which is a glass or a ceramic.

Figure 1B:
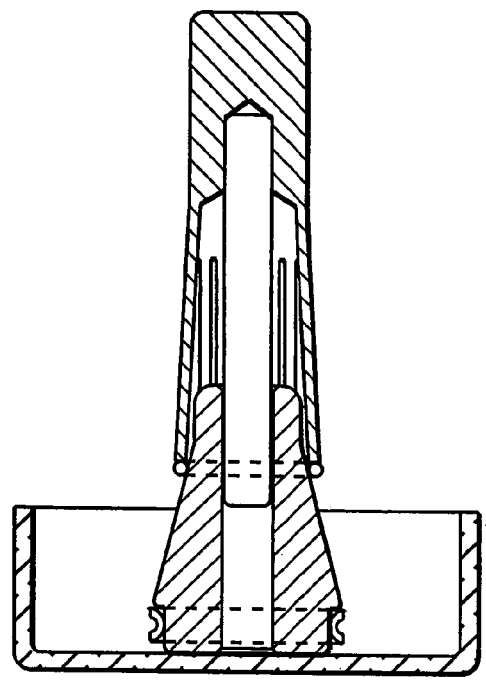
FIG. 1B-1D depict the use of apparatus (30) to urge band (24) in a direction from the apex of expander (20) towards the base of expander (20), and into the peripheral annular groove on the ring.
Figure 1C:
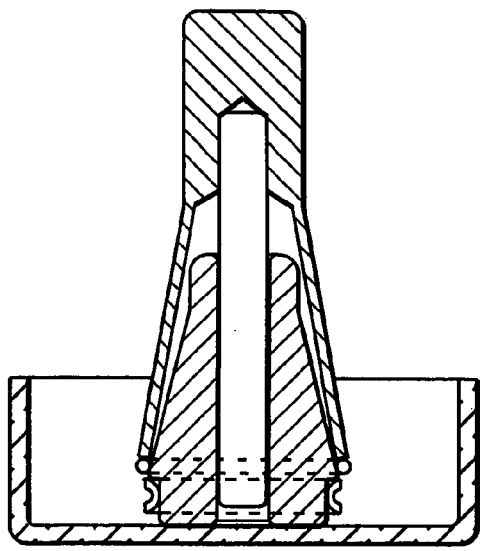
Figure 1D:
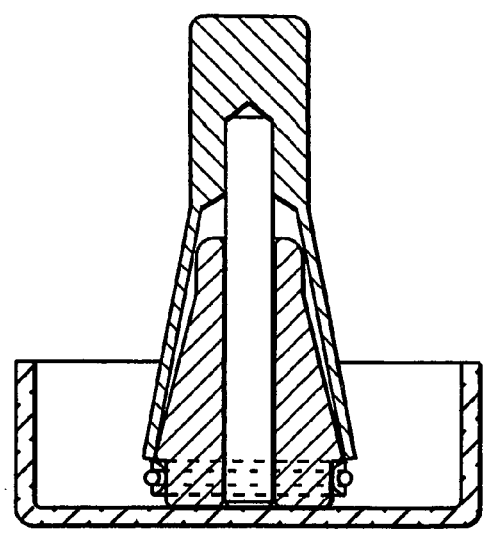
Figure 2:
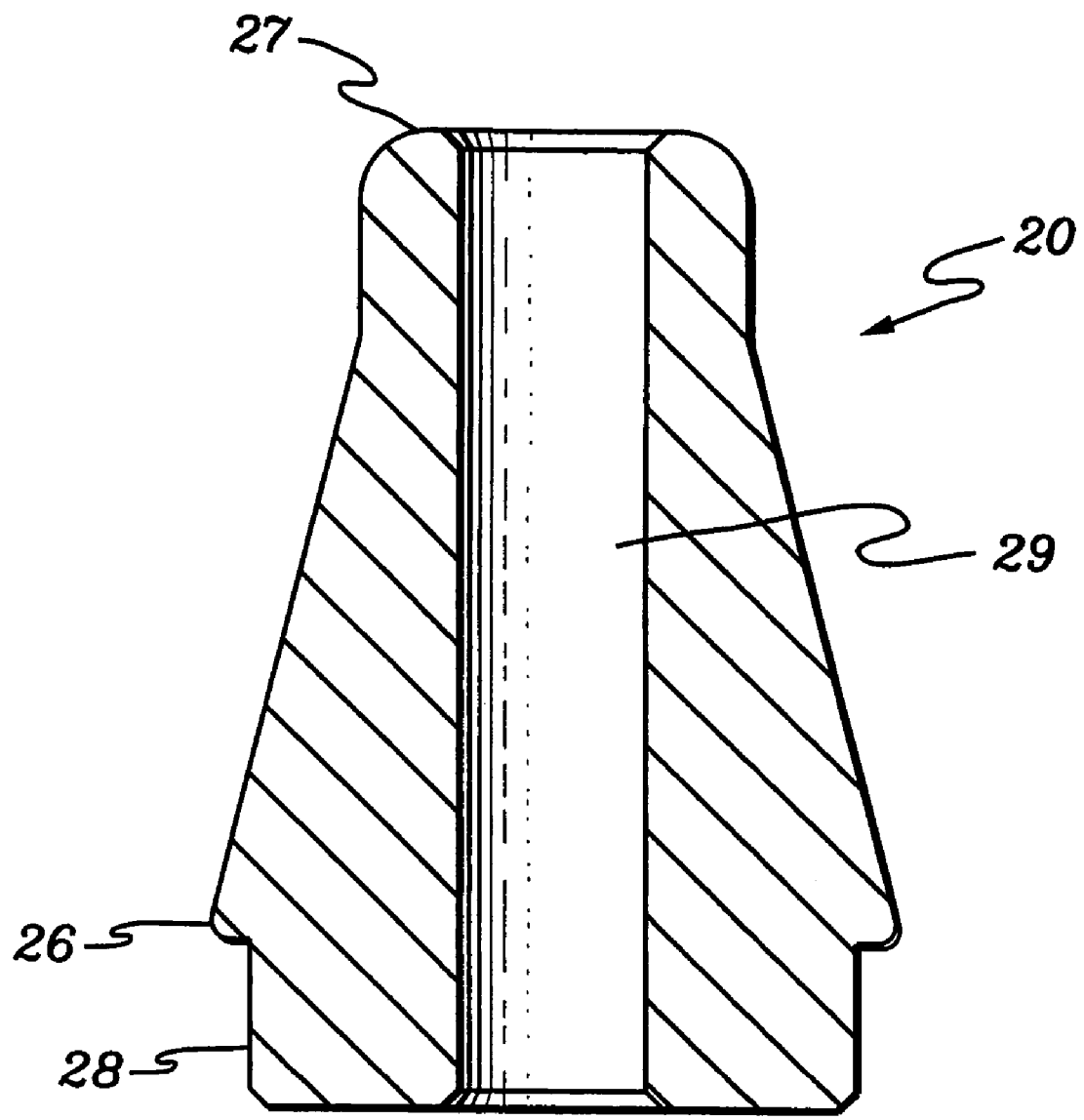
FIG. 2 is a partial transectional elevational view of a conical expander (20).
Figures 3A, 3B:
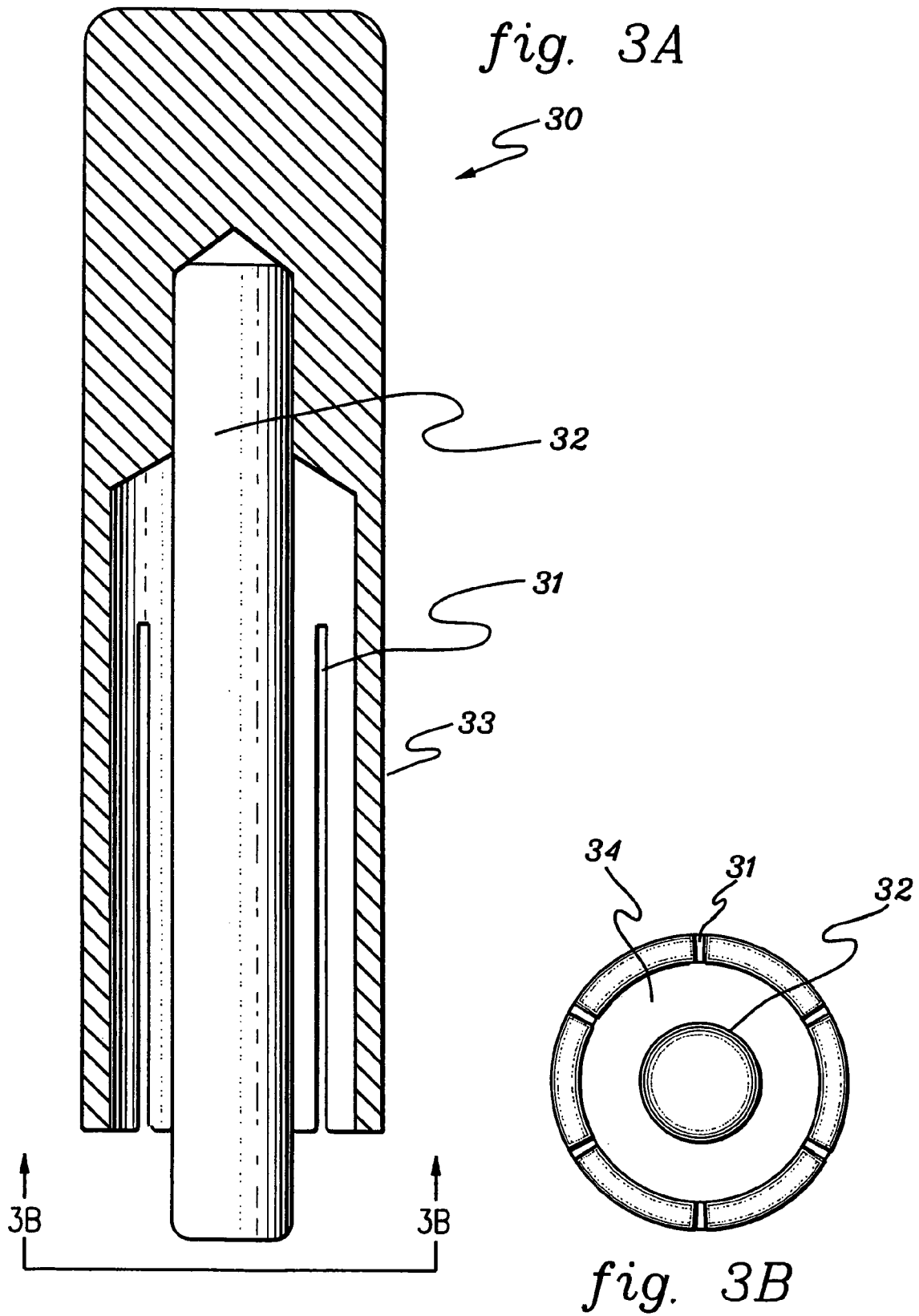
FIG. 3A is a partial transectional elevational view of apparatus (30) used to urge band (24) over the outer surface of the expander.
FIG. 3B is a cross-sectional view of apparatus (30).

According to an embodiment of the method of the invention, shown in FIG. 1A-1D, and FIG. 2, the urging of the band over the outer surface of the expander is carried out by the steps of contacting the band placed over the apex (27) of the expander (20) with an apparatus shown in FIGS. 1A-1D, and in FIG. 3A & B. The apparatus, shown in detail in FIGS. 3A and 3B, according to an embodiment includes a longitudinally extending cannula (34) having a proximal end portion and a distal end portion (33), the cannula defining a bore extending longitudinally therethrough from the proximal end portion to the distal end portion, and the cannula fitting coaxially over the apex (27) of the expander (20) and radially expandable at the distal end portion (33). According to an embodiment, the band placed over the expander (20) is frictionally engaged with the distal end portion (33) of the cannula, and biased over the outer surface of the expander (20) by advancing the cannula towards the base (28) of the expander (20).

According to a particular embodiment of the method, the expander (20) defines a rod-receiving space (29) having a first diameter and extending longitudinally from the apex (27) of the expander at least partially through the expander towards the base (28) of the expander (See FIG. 2.). FIGS. 1A and 3A show an embodiment of the apparatus of the invention (30) in a non-stressed configuration. The cannula (34) of the apparatus of the invention further comprises a rod (32) extending through the bore of the cannula, the rod having a second diameter that is less than the first diameter, the rod fitting coaxially in the rod-receiving space (29) of the expander to frictionally engage the expander and act as a stop to control the movement of the cannula when the cannula is fitted coaxially over the apex of the expander and advanced towards the base of the expander.

According to an embodiment, the cannula has a first shape, as shown in FIGS. 1A and 3A, which is substantially cylindrical when not subjected to mechanical stress, and a second shape in which the distal end portion (33) is substantially a radial flange (as shown in FIGS. 1C and 1D) when subjected to mechanical stress in a direction perpendicular to the axis of the cannula. The second shape of the cannula, in which the distal portion (33) forms a radial flange, allows the cannula to be advanced over the expander, and to be brought into grasping or frictional contact with an elastic band (24) placed over the apex of the expander.

To achieve the radial flange shape, an apparatus according to an embodiment may be comprised of a flexible material. A flexible material, as the term is used herein, is a material which is bendable or deformable and able to return to its original shape to a greater extent than is a non-flexible material.

According to another embodiment, depicted in FIG. 1A-1D and 3A and B the distal end portion (33) of the cannula of the apparatus includes a plurality of segments defined by a plurality of longitudinally cut slits (31) therein, the segments having a body portion and an end portion, and wherein as the cannula is advanced over the surface of said expander towards the base of said expander the segments thereof are splayed outwardly in a radial direction (as shown in FIGS. 1B-D, thereby forming the radial flange, and wherein the end portion of the segments are capable of frictionally engaging the radially elastic band placed over the apex of the expander.

Elastic band expansion is accomplished by applying a force to a band that has been placed over the apex (27) of a conical expander (20), and biasing the band over the outside surface of the expander (20) from the apex (27) or small diameter end to the base (28) or large diameter end, the base (28) having a shoulder (26), thereby expanding the band. The band is further biased over the shoulder (26) and into a peripheral annular groove on a ring placed in contact with the base (28) of the expander (22). In one embodiment the band is pushed manually by contacting the band with a hand, e.g., and pushing the band over the shoulder and in to the grove.

Figure 4B:
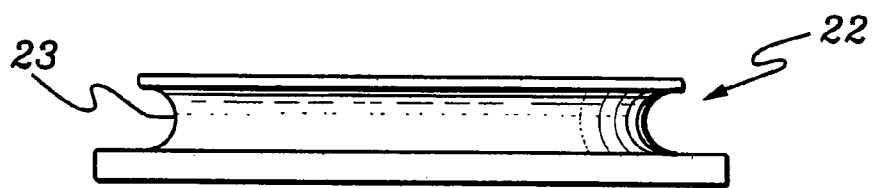
FIG. 4B is an elevational view of a ring (22) having a peripheral annular grove (23).
Figure 4C:
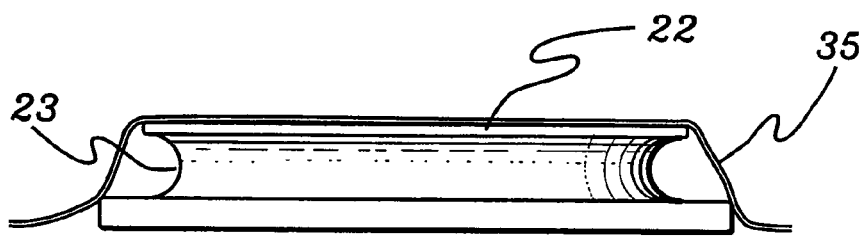
FIG. 4C depicts ring (22) draped with amniotic membrane (35).
Figure 4D:
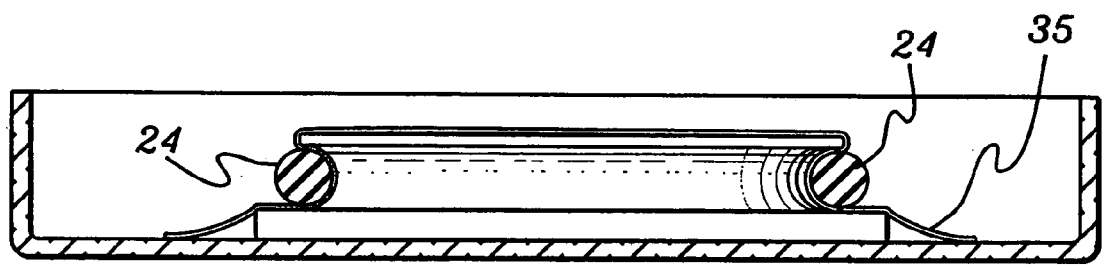
FIG. 4D depicts a culture insert including membrane (35) covering ring (22), the membrane secured by O-ring (24) inserted in the inner annular groove of ring (22), with the culture insert placed in a culture dish.

In one embodiment the ring (22), for example, the ring of FIG. 4B, having a peripheral annular groove (23) and placed in contact with base (28) of the expander (20) is a holding device having an annular rim, the rim curved to facilitate a controlled release of the band. In one embodiment, the ring or holding device is equipped with an actuator means, for example, a lever arm that can be pushed up against the band from under the band, providing a gap between the band and the rim of the holding device. According to an embodiment, the expanded band then moves through the gap in a controlled manner by means of its own stored elastic force from the holding device to a support such as a culture insert. As the band is released from the holding device, the band is translocated from the holding device to the support, and a membrane is fastened to the support.

Method and Device for Fastening a Membrane Between a Grooved Ring and an O-Ring Another embodiment of the invention, shown in FIG. 4A-FIG. 4D, is a device and a method of preparing the device comprising fastening a membrane to a ring (22) having an inner surface defining a hole and having at least one annular groove (23) sized to receive an O-ring (24). The device is formed by a method including the steps of contacting the membrane to be fastened with ring (22); positioning the membrane (35) on ring (22), thereby completely covering ring (22) with the membrane; and inserting O-ring (24) into the annular groove, thereby fastening the membrane to the ring. Accordingly, a composite of the invention is a culture insert including ring (22) having an inner surface defining a hole and having at least one annular groove (23) sized to receive O-ring (24); a membrane (35) mounted to ring (22), membrane (35) completely covering ring (22); and O-ring (24) inserted in annular groove (23) to fasten the membrane to ring (22) during assembly.

Figure 5A:
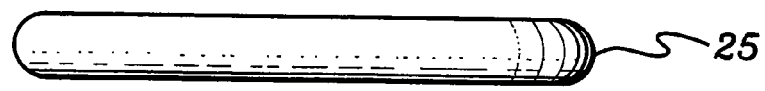
FIG. 5A depicts an O-ring (25).
Figure 5B:
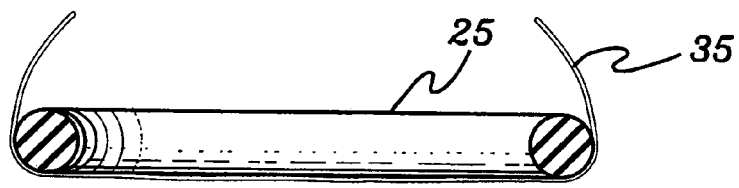
FIGS. 5B and 5C depict O-ring (25) wrapped with membrane (35).
Figure 5C:
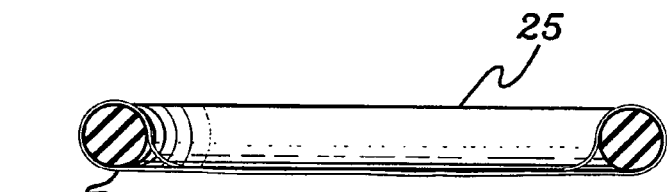
Figure 5D:
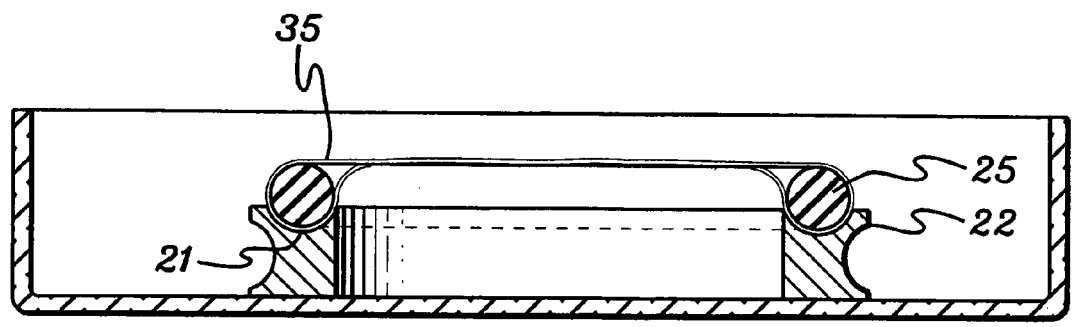
FIG. 5D depicts wrapped O-ring (25) inserted in the inner annular groove (21) of ring (22) to form a culture insert, the insert shown placed in a culture dish.

In an alternative embodiment of the method and device of the invention, shown in FIG. 5A-FIG. 5D, O-ring (25) is first covered with the membrane (35). As such, another embodiment of the invention is a method of fastening a membrane between O-ring (25) having an outer peripheral annular surface and a ring (22) having an inner annular surface defining a hole and having at least one annular groove (21), the method including the steps of contacting the membrane to be fastened with O-ring (25); positioning membrane (35) on O-ring (25), thereby completely covering O-ring (25) with membrane (35); wrapping the membrane (See FIG. 5B.) over the outer peripheral annular surface of O-ring (25) to form a wrapped O-ring (See FIG. 5C.); and inserting the wrapped O-ring into annular groove (21) (See FIG. 5D.), thereby fastening membrane (35) between O-ring (25) and ring (22). The device formed according to an embodiment of the invention is a culture insert, and can be placed in a culture dish, as shown in FIG. 5D.

The membrane used in an embodiment of the method and device of the invention comprises an amniotic membrane. In another embodiment of the invention the membrane is a hyaluronan derivative, collagen or a collagen derivative, or a material formed from a polycarbonate, polyethylene terephthalate, polyester or styrene-acrylonitrile material. A membrane and a support used in an embodiment comprise one or more biocompatible materials. "Biocompatible," as the term is used herein, refers to a material that has no medically unacceptable toxic or injurious effects on biological function.

In one embodiment (shown in FIG. 4B the annular groove (23) is located on the periphery of the ring. In another shown in FIG. 5D embodiment, the annular groove (21) or is located on the inner annular surface of the ring. In a particular embodiment (FIG. 5D) there are two annular grooves.

Figure 6A:
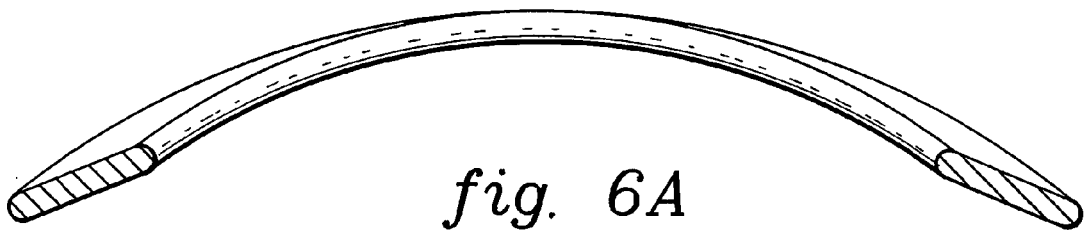
FIGS. 6A & 6B are perspective views of sections of two snap together rings.
Figure 6B:
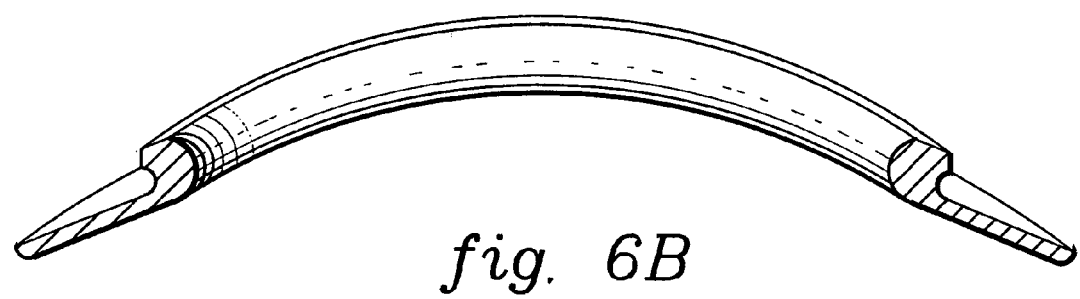
Figure 6C:
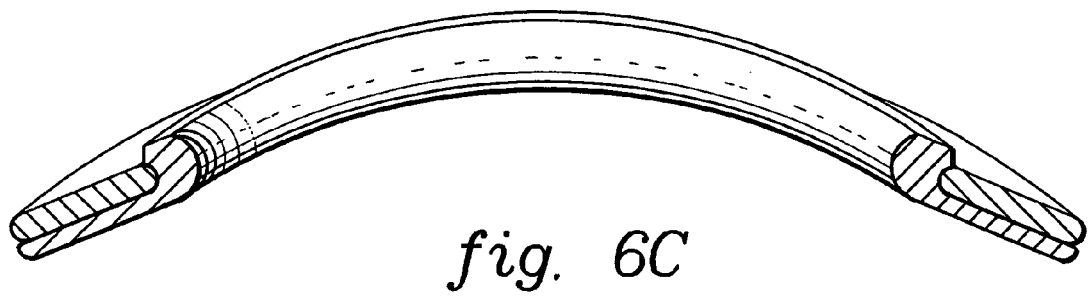
FIG. 6C is a perspective view of the rings of FIGS. 6A and 6B in locking engagement with one another.
Figure 6D:
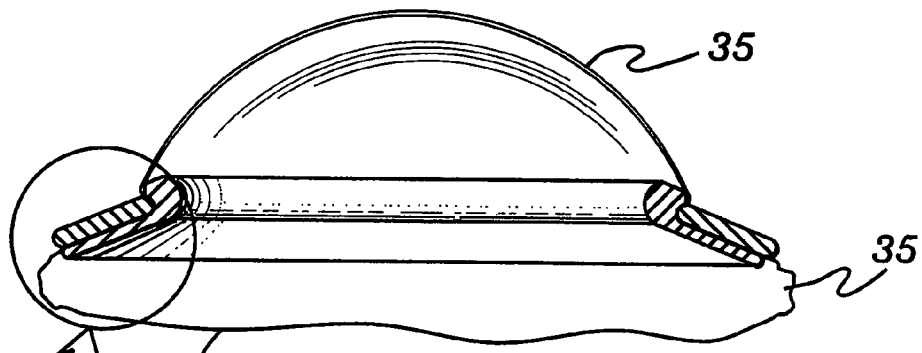
FIG. 6D is a partial transectional perspective view of the rings of FIGS. 6A and 6B with membrane (35) fastened between the rings.
Figure 6E:
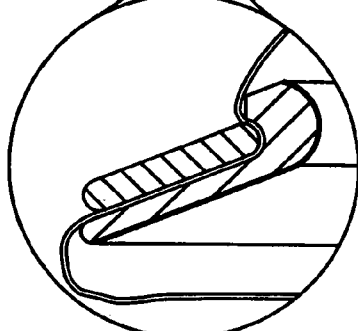
FIG. 6E is an enlargement of a section of FIG. 6D to better show membrane (35).
Figure 6F:
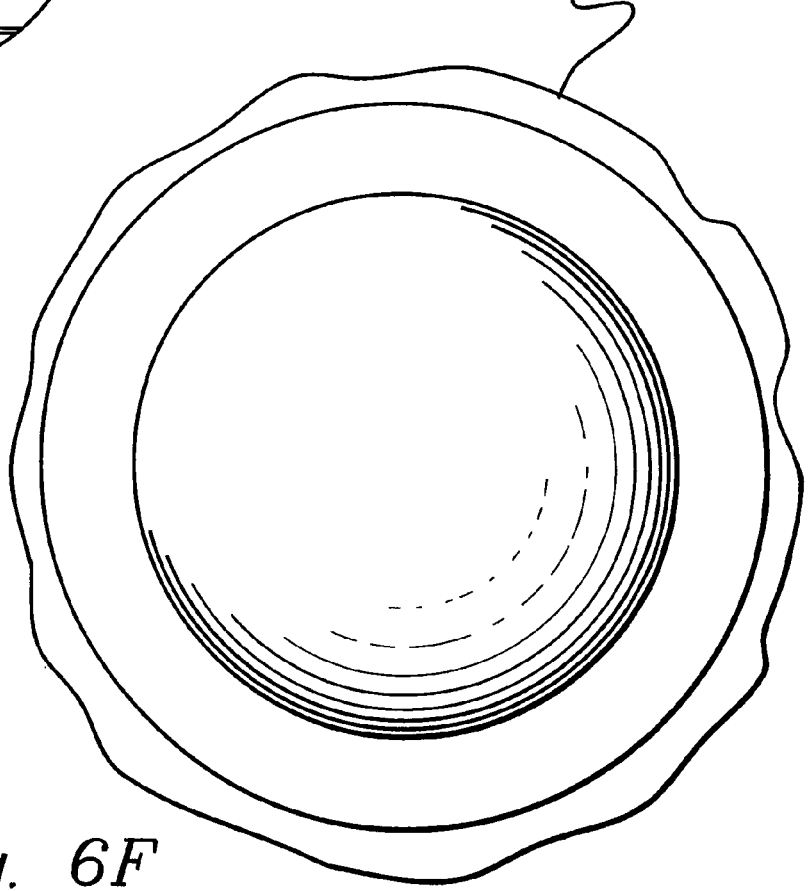
FIG. 6F is a top plan view of membrane (35) fastened between the rings of FIGS. 6A and 6B.

In yet another embodiment (shown in FIG. 6A-6F) the membrane (35) is attachable to a support by placing membrane (35) over a lower support ring as shown in FIG. 6B, and then pinching or sandwiching membrane (35) between the ring of FIG. 6B and the ring of FIG. 6A, by pressing the rings together, the rings having a snap together fit, as shown in FIG. 6C-6F. As the term is used herein, a "snap together fit" refers to the fit of a first ring (FIG. 6B) within a second, concentric ring (6A), wherein the two rings can be attached to one another by means of a peripheral annular edge of the first ring (FIG. 6B) lockingly engaging an inner annular edge of the second ring (FIG. 6A), as depicted in 6C. As used herein, the term "snap together rings" refers to two concentric rings having a snap together fit. For example, FIG. 6D is a perspective sectional view of two snap together rings that comprise a support for an embodiment of an amniotic membrane covering for a tissue surface such as an ocular surface. The covering, an amniotic membrane (35) fastened between two snap together rings, is shown as a top plan view in FIG. 6F, and can be used as a bandage or dressing for chemical or thermal burns to the eye. FIG. 6D, a full sectional view of the covering, shows the amniotic membrane (35) clamped between the snap rings of FIGS. 6A-6C.

Figure 6G:
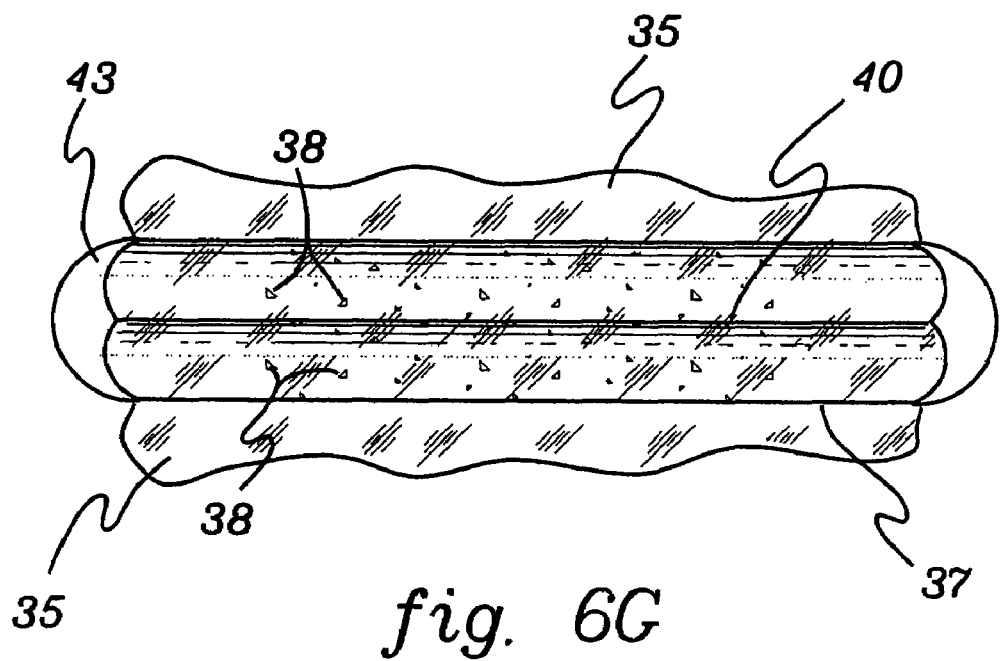
FIG. 6G is a partial transectional elevational view of two snap-together rings, the inner ring (37) having burs on the outer peripheral surface thereof.
Figure 6H:
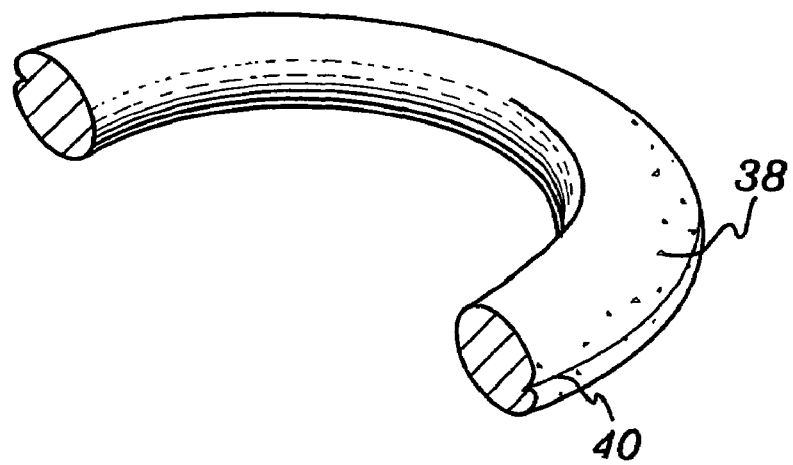
FIG. 6H is a sectional view of inside ring 37, having burs on the outer edge thereof.

FIG. 6G is a partial cross sectional lateral view of two snap together rings, wherein the inside ring (37) has burs (38) on the outer edges thereof. The burs (38) and the seam (40) can be used to help hold the membrane in place between the inside ring (37) and outside ring (43). FIG. 6H is a sectional perspective view of the inside snap together ring of FIG. 6G, showing the burs (38) along the outside edge thereof.

Use of Support Members Having Fastener Posts and Fastener Post Apertures

Figure 7A:
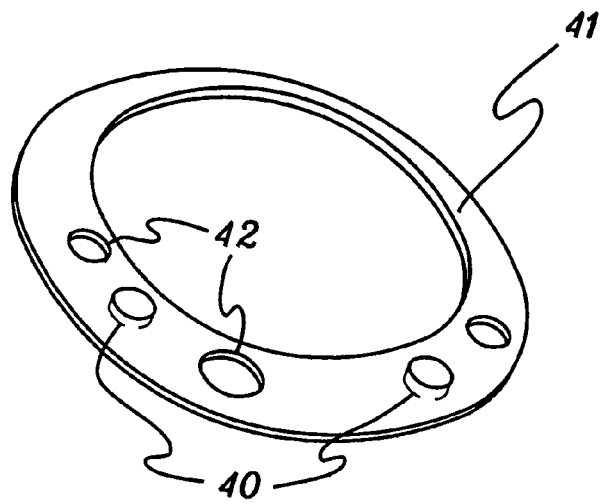
FIG. 7A is a perspective view of snap-together ring (41) including holes (42) thereon to fit over fastener posts (40) on a second ring (39) shown in FIG. 7C.

Another embodiment of the invention is a device and a method using a fastener system that allows for the attachment of a membrane to two support members, for example, two rings, without the need for hardware or glue. The fasteners, which may be continuous with the body of the support members, comprise two members, a fastener post, which is also referred to as a "male snap pin," and a fastener post aperture, which serves as a receiver for the fastener post. The fastener post aperture is also referred to as a "female snap hole." The fastener posts define prongs or projecting areas on the surface of one of the support pieces or snap together rings. Fastener post apertures on the surface of one of the support pieces are spaced and configured to mate or lockingly engage with the fastener posts. According to an embodiment illustrated in FIG. 7A-7C, a membrane is fastened between a first snap together ring (39) (FIG. 7C) and a second snap together ring (41) (FIG. 7A). According to an embodiment, the first snap together ring (39) includes a surface comprising a plurality of spaced fastener posts (40), and the second snap together ring (41) includes a surface defining a plurality of spaced fastener post apertures (42). In another embodiment, each of the first and second snap rings comprise a surface including fastener posts spaced between fastener post apertures.

The assembly of a culture insert or an amniotic membrane covering for a tissue surface using an amniotic membrane and two supports or rings according to an embodiment is easily accomplished, and the amniotic membrane and supports required to fabricate a culture insert or a covering for a tissue surface can be supplied as components of a kit according to an embodiment. The interlocking engagement of the supports having fastener posts mated with fastener post apertures is secure, in that considerable force is required to separate the fastener posts from the fastener post apertures.

The supports or rings can be fabricated, according to a particular embodiment, from a flexible material. A flexible material, as the term is used herein, is a material which is bendable or deformable and able to return to its original shape to a greater extent than is a non-flexible material. An embodiment includes, for example, a support comprised of a polymer such as polyethylene, vinyl, plastic and silastic material.

Figure 7B:
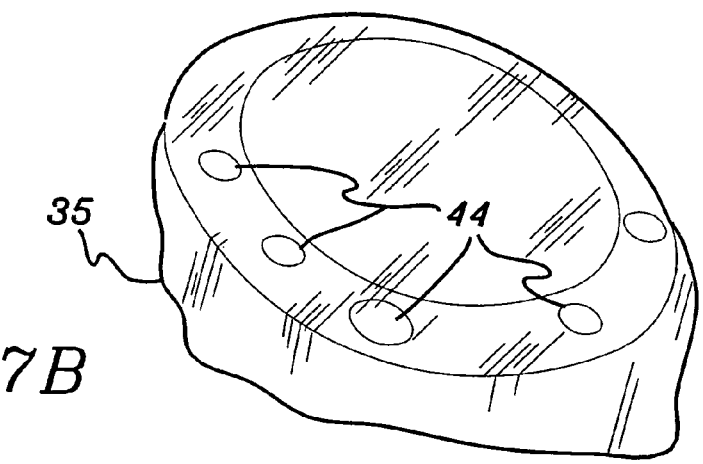
FIG. 7B is a perspective view of ring (41) with membrane (35) draped thereon.
Figure 7C:
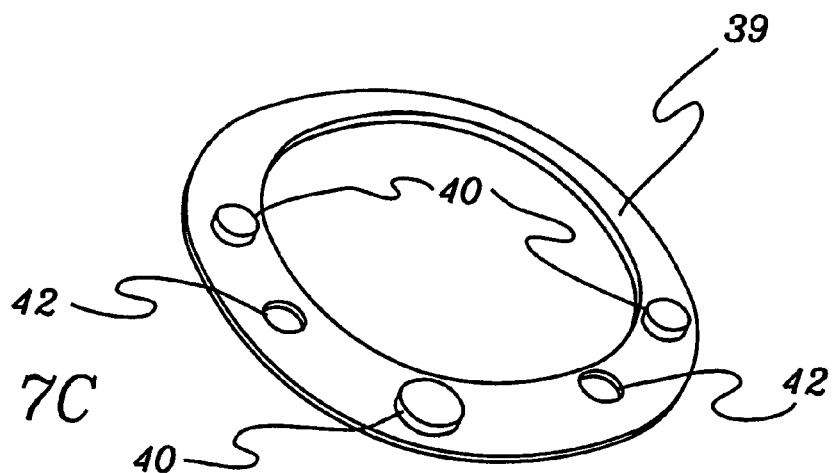
FIG. 7C is a pictorial view of a snap together ring (39) including spaced fastener posts (40) thereon.

The method includes the steps of contacting the membrane (35) to be fastened with the surface of the first ring (39); positioning the membrane on the first ring (39), thereby completely covering the first ring (39) with the membrane, as depicted in FIG. 7B; positioning the second ring (41) over the first ring (39) for alignment of at least one of the spaced fastener posts (40) with at least one of the spaced fastener post apertures (42); and lockingly engaging the first ring (39) with the second ring (41), by inserting at least one of the posts (40) in a fastener post aperture (42), thereby fastening the membrane between the first ring (39) and the second ring (41). According to an embodiment, the amniotic membrane covers the outside of one or both sides of the snap together rings. The membrane also wraps around the snap together rings so that it will be clamped between the two rings and over the edges of the rings. In a particular embodiment, the amniotic membrane (35), has holes spaced to fit over the fastener posts on the ring (39).

Accordingly, a composite of the invention is a culture insert or an amniotic membrane covering for a tissue surface including a first snap together ring having a first surface; a plurality of spaced fastener posts located on the first surface; a second snap together ring having a second surface defining a plurality of spaced fastener post apertures thereon, wherein at least one of the apertures is spaced to align with a position of at least one of the posts when the two rings are matingly engaged during assembly; and a membrane fastened between the two snap together rings.

Use of a Support Having a Cut Slit

Figure 8A:
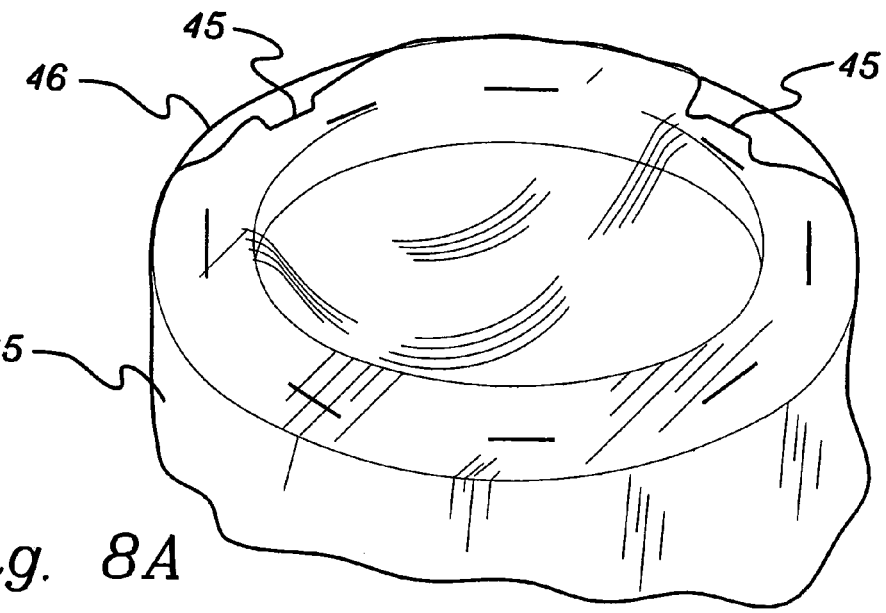
FIG. 8A depicts membrane (35) positioned on a ring (46) with a cut slit (45), the membrane (35) pushed into slit (45) on the peripheral surface of ring (46).

Another embodiment of the invention, illustrated in FIG. 8A-8E, and FIG. 9A-9D, is a device and a method of preparing the device comprising fastening a membrane to a ring (46) having a peripheral annular surface, an inner annular surface, a top surface and a bottom surface, with at least one surface defining at least one cut slit (45) thereon. As depicted in FIG. 8A the method includes the steps of contacting the membrane to be fastened with ring (46); positioning membrane (35) on the top surface or the bottom surface of ring (46), thereby covering ring (46) with membrane (35); and inserting membrane (35) into cut slits (45), thereby fastening membrane (35) to ring (46). According to a particular embodiment, the membrane is inserted into at least one cut slit on the top surface or the bottom surface. In another embodiment, the membrane is inserted into a cut slit on the peripheral annular surface.

Figure 8B:
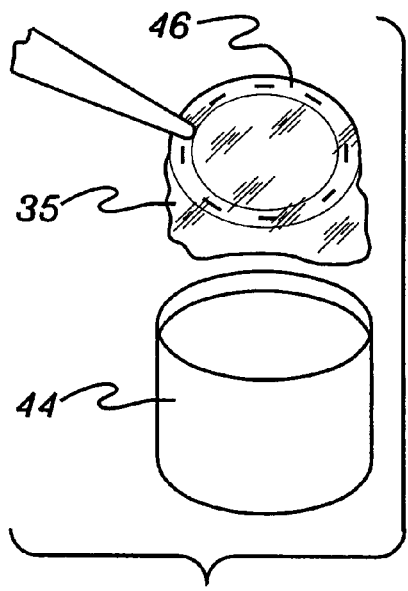
FIG. 8B depicts ring (46) with loosely adherent membrane (35) pushed or inserted into slit 45, ring (46) being lifted out of mold (44) by a forceps.
Figure 8C:
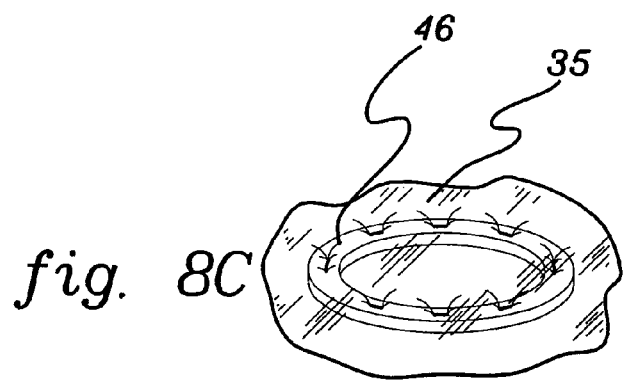
FIG. 8C depicts ring (46) with loosely adherent membrane (35) being pushed or inserted into slit 45.
Figure 8D:
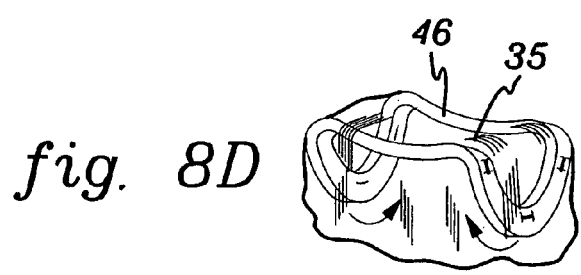
FIG. 8D depicts ring (46) with loosely adherent membrane (35), ring (46) being rotated to wrap the ring in amniotic membrane.
Figure 8E:
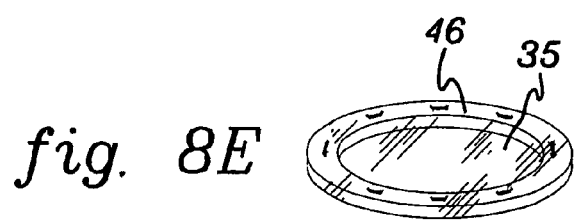
FIG. 8E depicts ring (46) wrapped with membrane (35).

FIG. 8B shows the ring (46) with loosely adherent membrane (35) being lifted out of the mold (44) by use of a forceps. FIG. 8C shows the ring (46), with loosely adherent membrane, being rotated in order to wrap membrane (35) around ring (46) and cover ring (46). Alternatively, the step illustrated in FIG. 8D can be carried out by placing the ring with membrane covering it on a plate, pushing on opposites sides of the ring with a probe to rotate the ring. The ring will flip and cover itself with membrane, as shown in FIG. 8E.

In one embodiment the device made by inserting an amniotic membrane into a slit on a support is a culture insert. In another embodiment the device so made is a covering for a tissue surface.

FIG. 9A-9D shows an embodiment of a biopolymer covering for a tissue surface in which an amniotic membrane (35) is inserted into slits (50) on the upper or lower surface of one of the rings (48). FIG. 9D shows that membrane (35) is stretched over ring (48). If a sufficiently large piece of membrane is used, ring (48) is completely wrapped with membrane (35) by rolling ring (48).

Wrapping a Ring with Membrane and Snap-Fitting the Wrapped Ring Inside a Second Ring According to another embodiment of a device and a method of the invention a biopolymer covering for a tissue surface is made by the steps of contacting a biopolymer membrane with the surface of a first ring having an outer annular edge and an outside diameter sized to snap-fit within the inside diameter of a second ring having an inner annular edge; positioning the membrane on the first ring, thereby completely covering the first ring with the membrane and wrapping the membrane over the outer annular edge of the first ring; positioning the second ring over the first ring for coaxial alignment therewith; and lockingly engaging the first ring with the second ring, thereby fastening the membrane between the first ring and the second ring, and making a biopolymer covering for a tissue surface or a culture insert.

Amniotic Membrane Including Cells Attached Thereto

In one embodiment of the invention, an amniotic membrane fastened between the first ring and the second ring is a biopolymer covering for a tissue surface. As the terms are used herein, a "biopolymer covering for a tissue surface," a "biopolymer covering," or a "covering" includes, for example, a dressing, a bandage, a drape such as a bandage contact lens, a composition or covering to protect tissue, a covering to prevent adhesions, to exclude bacteria, to inhibit bacterial activity, or to promote healing or growth of tissue.

In another embodiment of the invention, an amniotic membrane fastened between the first ring and the second ring is a culture insert. An embodiment of the invention, such as, for example, a biopolymer membrane of a covering for a tissue surface, a biopolymer membrane of a culture insert, or of any other device according to the invention, may include one or more cells. In a particular embodiment, the cells are grown on the membrane or attached to the membrane before the membrane is contacted with or attached to the surface of the first ring. In another embodiment, the cells are grown on or attached to the membrane after the membrane is fastened between the first and second rings.

The cells grown thereon may be any type of cells, for example, epithelial stem cells, retinal pigment epithelial cells, limbal stem cells, and limbal epithelial cells.

A covering according to an embodiment can be used as a scaffold or matrix for tissue engineering in vitro or in vivo. Methods of culturing cells in vitro are well know to those of skill in the tissue culturing art. For example, amniotic membrane fastened to a culture insert or a silicone ring according to an embodiment of the invention can first be used in a culture for growing cells or tissue engineering, according to methods known in the art. Then the amniotic membrane with one or more cells attached thereto can be used to make a biopolymer covering for a tissue surface according to an embodiment of the invention. The source of the cells attached to the amniotic membrane may be tissue from a biopsy taken from a healthy site corresponding biologically and histocompatible to the recipient site.

As described earlier, amniotic compositions are known to promote healing, reduce inflammation and fibrovascular ingrowth, and to facilitate epithelialization in animal models. As such, the covering containing amniotic membrane, when placed on a damaged tissue surface and allowed to remain until a noticeable improvement occurs, can help to heal or grow new tissue.

In another embodiment, the biopolymer covering for a tissue surface includes one or more cells, pre-engineered for gene therapy, attached to the membrane. In one embodiment, the membrane includes cells that incorporate genetic material such as, for example, genes or antisense. According to an embodiment, the biopolymer covering for a tissue surface with one or more cells attached to the membrane can then be used as a graft and implanted at a target tissue site. The graft or implant incorporating genetic material can thus be used for gene therapy.

Biopolymer Coverings Conforming to Contours of a Body Tissue Surface

The biopolymer covering for a tissue surface can be modified to stretch the amniotic membrane or to make the support rings conform to the contours of a body tissue surface. For example, in one embodiment, the first ring and the second ring are each sized and contoured for placement on an outer surface of an eye.

Figure 19A:
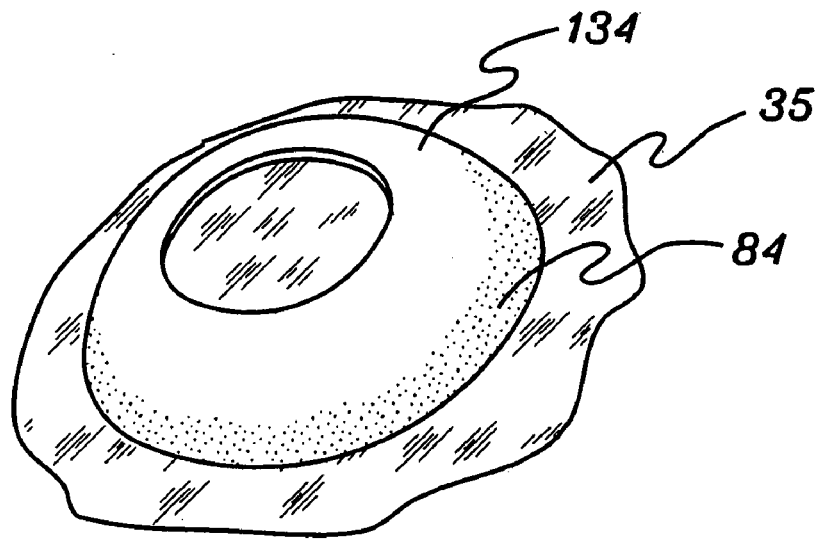
FIG. 19A is a pictorial view of a support (134) shaped to fit over an ocular surface, the support having an adhesive composition (84) as previously described in contact with a portion of the outer peripheral surface of support (134), and a membrane (35) positioned over the inner surface of support (134), membrane (35) positioned to be folded up and over the outer peripheral surface of support (134), such that membrane (35) is in contact with glue (84) and is held in place by glue (84).
Figure 20A:
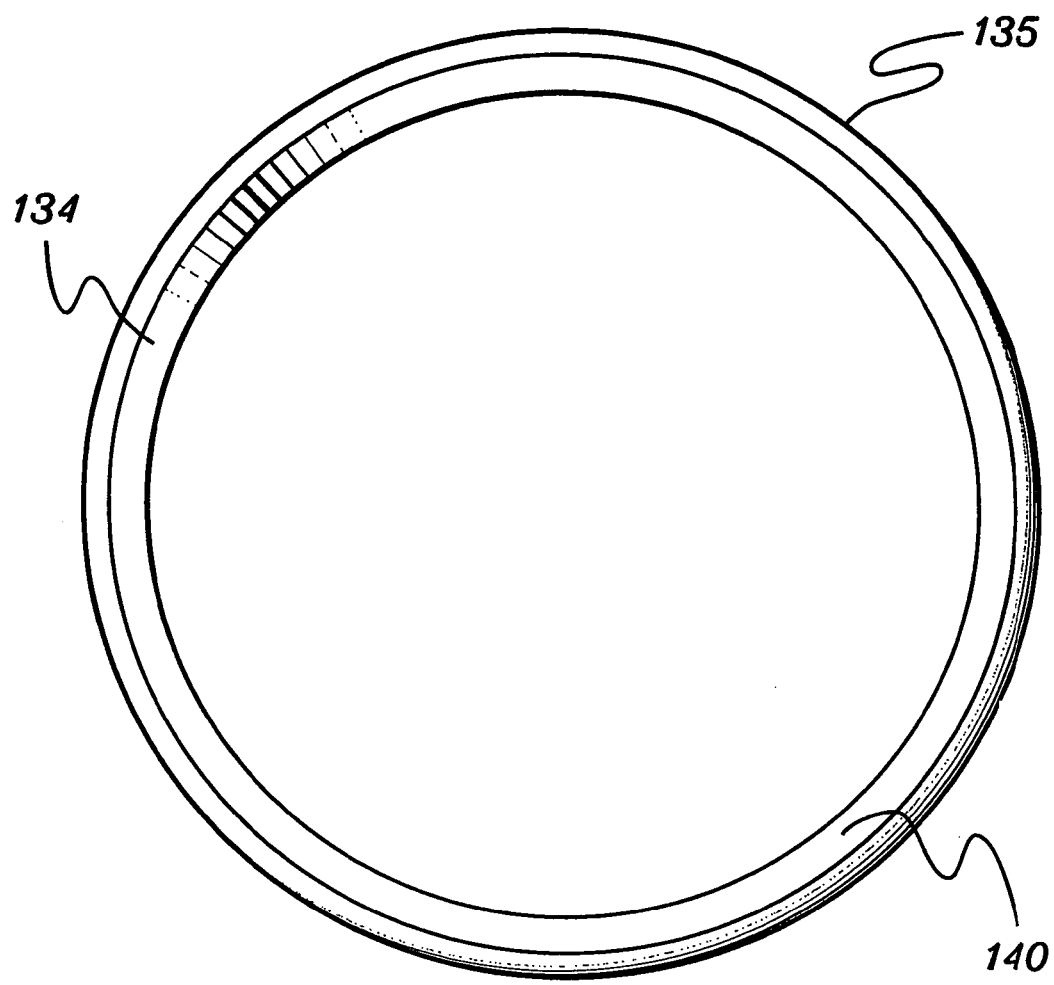
FIG. 20A is a top plan view of another embodiment of a support for an amniotic membrane covering for an ocular surface, the support having a beveled, inside, annular groove (140), and a surface (134), and an outside, rounded edge (135) on the periphery thereof.
Figure 20B:
FIG. 20B is a partial transectional side elevational view depicting the profile of the support shown in FIG. 20A, the support having a sloped inside annular surface (134) that lockingly engages annular groove (150) in FIGS. 21A and 21B.
Figure 21A:
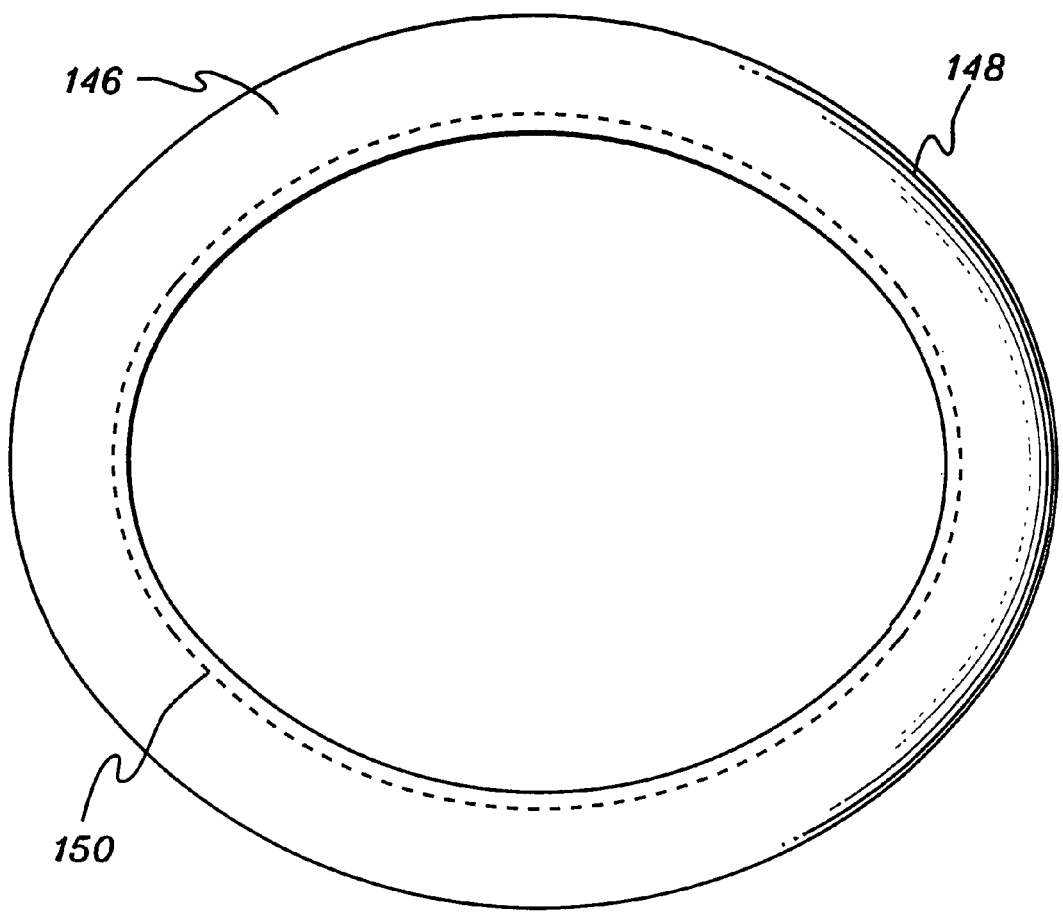
FIG. 21A is a top plan view of a support for an amniotic membrane covering for an ocular surface, the support having a sloped concave inner surface (146); a rounded annular edge (148); and an annular groove (150) that lockingly engages sloped inside annular surface (134) in FIGS. 20A and 20B.
Figure 21B:
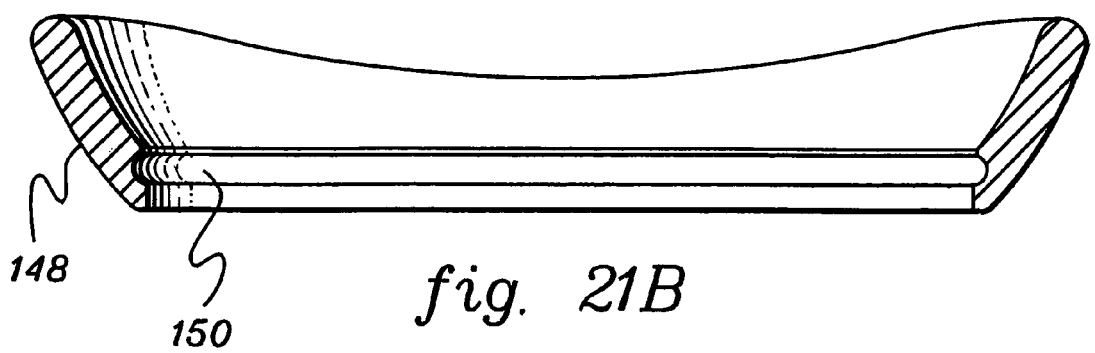
FIG. 21B is a partial transectional side elevational view depicting the profile (148) of a support for an amniotic membrane covering an ocular surface shown in FIG. 21A, and incorporating an annular groove (150) in the inside bottommost vertical wall.

For example, as shown in FIG. 19A, a support may be a conformer ring with a surface contoured to the ocular surface. Similarly, FIG. 20A depicts a conformer ring having a sloping surface (140) that snaps together with the groove (150) of the conformer ring shown in FIG. 21A, securing between the rings a membrane that is previously placed over the surface (146) of the ring of FIG. 21A. How the two rings fit securely together is best understood from a comparison of FIG. 20B with FIG. 21B. The rings may, independently, each be circular or elliptical in shape. The rings in FIGS. 20A and 21A are flexible and may be stretched to accomplish locking together, even if both rings do not have the same shape. The support depicted in 21A may be shaped like a conformer such as, for example, the support shown in FIG. 19A.

In another embodiment, the biopolymer membrane, the first ring, and the second ring are each sized for placement on a tissue surface which is dermal tissue, gastrointestinal tract tissue, respiratory tract tissue, genital system tissue, urinary system tissue, circulatory system tissue, or bone tissue.

Biodegradable Support and Controlled Drug Release

According to one embodiment, the first ring and the second ring are biodegradable. According to another embodiment, either the first ring or the second ring is biodegradable. A "biodegradable substance," as that term is used herein, is one that is capable of being decomposed by natural biological processes. In a particular embodiment of the invention, if the support in a biopolymer covering is biodegradable, and if the covering is used as a surgical implant, the support would disintegrate and dissolve or be absorbed, eliminating the necessity to surgically remove the implant.

In one embodiment, at least one of the supports or rings in a biopolymer covering for a tissue surface includes a bioactive molecule, which may be a pharmaceutically active or therapeutic substance such as a drug. As the term is used herein, "bioactive molecule" includes substances that are capable of causing specific effects or reactions on target tissue or organisms. If the support is biodegradable, the pharmaceutically active molecule or drug is slowly released as the support breaks down. The rate of degradation of a given support, and the rate of the accompanying release of a therapeutic substance included in the support, is predictable when a support made of a material with a known, suitable rate of degradation is used in an embodiment of a covering for a tissue surface. Thus, a biopolymer covering for a tissue surface according to this embodiment is a controlled release delivery vehicle for a therapeutic substance.

Any substance that has biological or pharmaceutical activity and which is normally considered to be a drug can be used as the drug component in an embodiment of the invention. Pharmaceutically active substances suitable for use in an embodiment include, but are not limited to, cells, analytes, growth factors, enzymes, therapeutic drugs, biopolymers, anti microbials, and deodorant agents.

A "therapeutic drug," "therapeutic agent," or "therapeutic substance," as those terms are used herein, include, for example: compounds and compositions recognized in the official United States Pharmacopoeia, the official Homeopathic Pharmacopoeia of the United States, or the official National Formulary, or any supplement of any of them; compounds and compositions intended for use in the diagnosis, cure, mitigation, treatment, or prevention of disease in man or other animals; and compounds and compositions (other than food) intended to affect the structure or any function of the body of man or other animals.

Examples of classes of therapeutic drugs include steroidal and non steroidal anti-inflammatory drugs, hormones and any synthetic analogues and pharmaceutically active fragments thereof. Therapeutic drugs which are suitable for use in embodiments of the invention may be fat-soluble, water soluble, anionic or cationic, as long as they can be dispersed within or on the membrane or the support, or interact with a group on the membrane or the support to form either covalent or ionic bonds or hydrophobic or hydrophilic interactions.

The delivery system of the invention is well suited for administering growth factors (e.g., interleukins, prostaglandins, thromboxanes, leukotrienes and cytokines), steroidal and non steroidal contraceptive agents, antibiotics, analgesics, sedatives, barbiturates, aminoalkybenzenes, catecholamines, narcotics, narcotic antagonists, anti-neoplastic agents and anticoagulants.

A controlled release drug delivery vehicle, such as, for example, a biopolymer covering for a tissue surface according to an embodiment of the invention, including a membrane or a biodegradable support that further includes a therapeutic agent, can provide the appropriate level of bioavailability of a therapeutic agent at the affected area to achieve a desired clinical result. The bioavailability of a drug depends upon the nature of the drug, the drug delivery vehicle used, and the route of delivery, for example, oral, topical, transdermal, mucosal, administration by injection, administration by inhalation, or administration by a combination of two or more of these routes. The bioavailability may be low as a result of, for example, the degradation of the drug by stomach acid, elimination from the gastrointestinal tract, or high aqueous solubility of the drug. As a result, frequent administration may be required, and the amount of drug delivered with each administration may be high, leading to an increase in the occurrence of damaging side effects. A controlled release drug delivery vehicle can alleviate some of the aforementioned problems.

For example, in one embodiment of the invention, a drug such as cyclosporin A, which has severe, damaging systemic effects if taken internally, can be administered by being incorporated in the amniotic membrane or the biodegradable ring of a biopolymer covering for an ocular surface, and delivered topically, thereby minimizing absorption by the body and resulting damage to internal organs.

Snap Together Rings Having Gripping Surfaces According to Another Embodiment

Figure 10A:
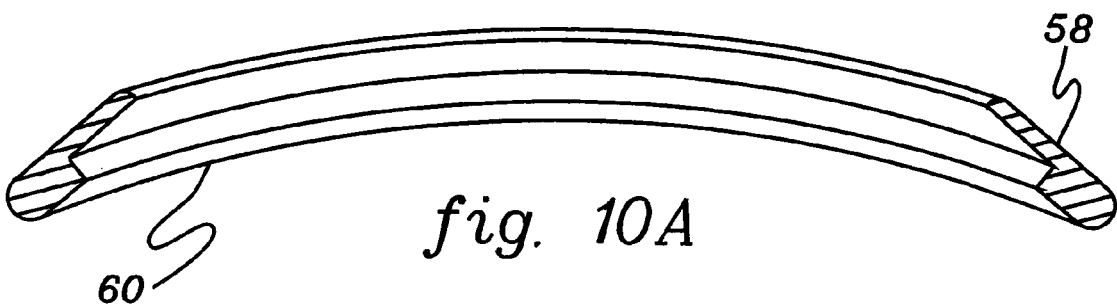
FIG. 10A is a partial transectional view of an outer snap together ring.
Figure 10B:
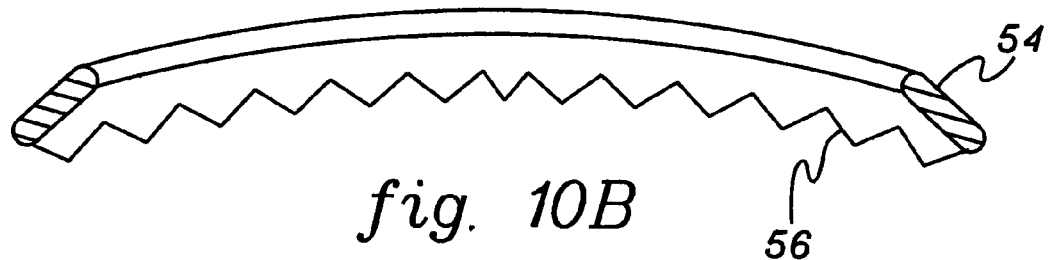
FIG. 10B is a partial transectional view of an inner snap together ring having a gripping edge (56).
Figure 10C:
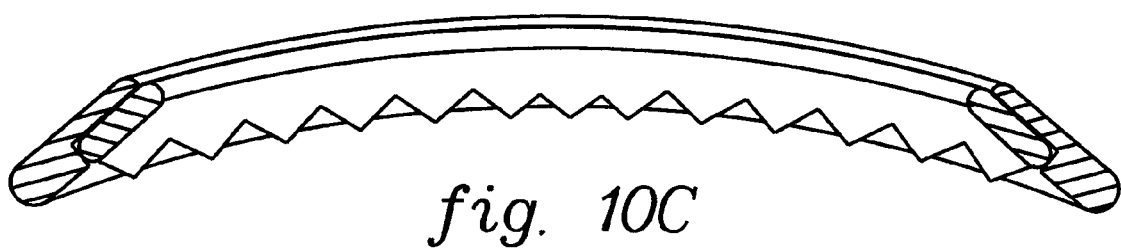
FIG. 10C is a partial transectional view of the snap together rings of FIGS. 10A-10B lockingly engaged.
Figure 10D:
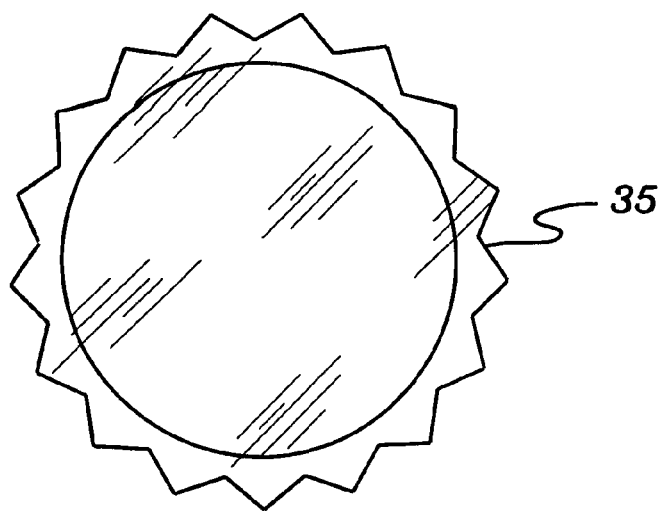
FIG. 10D is a top plan view of a biopolymer covering for a tissue surface with membrane (35) fastened between the snap together rings of FIGS. 10A and 10B, showing how the membrane can be positioned on top of the covering.

In addition to an embodiment of the invention including a support ring having an area defining fastener posts and fastener post apertures, as described above, other types of gripping surfaces on the two support pieces are used in other embodiments. For example, as shown in FIGS. 10A-10C, one embodiment of the invention is a device useful as a biopolymer covering for a tissue surface or as a culture insert. The device, shown in FIG. 10D with membrane (35) sandwiched between the snap together rings, includes snap together rings (54, 58), wherein the outer annular edge (56) of the inner ring (54) includes a first gripping surface (56) and the inner annular edge (60) of the outer ring (58) includes a second gripping surface (60). As shown in a top plan view of the covering in FIG. 10D, a membrane such as an amniotic membrane (35) is secured by being clamped between the two gripping surfaces of rings 54 and 58. In a particular embodiment, a partial sectional perspective view of which is shown in FIGS. 10A-10C, a secure snap together fit of the outer ring and the inner ring is achieved by tapering or angling the inner annular edge (66) of the ring (64) to, for example, 90° or more, and the edge (70) of ring (68) to 90° or less, so that the edges (66 and 70) that are to contact one another, grip, and lockingly engage one another.

In another embodiment of the invention, the gripping surfaces include a gripping device that is burs.

Use of Adhesive to Fasten Amniotic Membrane to a Support

Figure 11A:
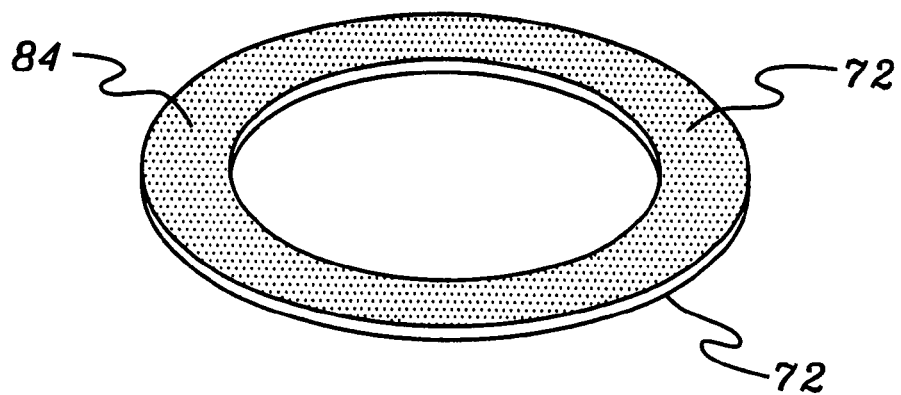
FIG. 11A is a pictorial view of a support (72) with glue (84) added to a surface thereof.
Figure 11B:
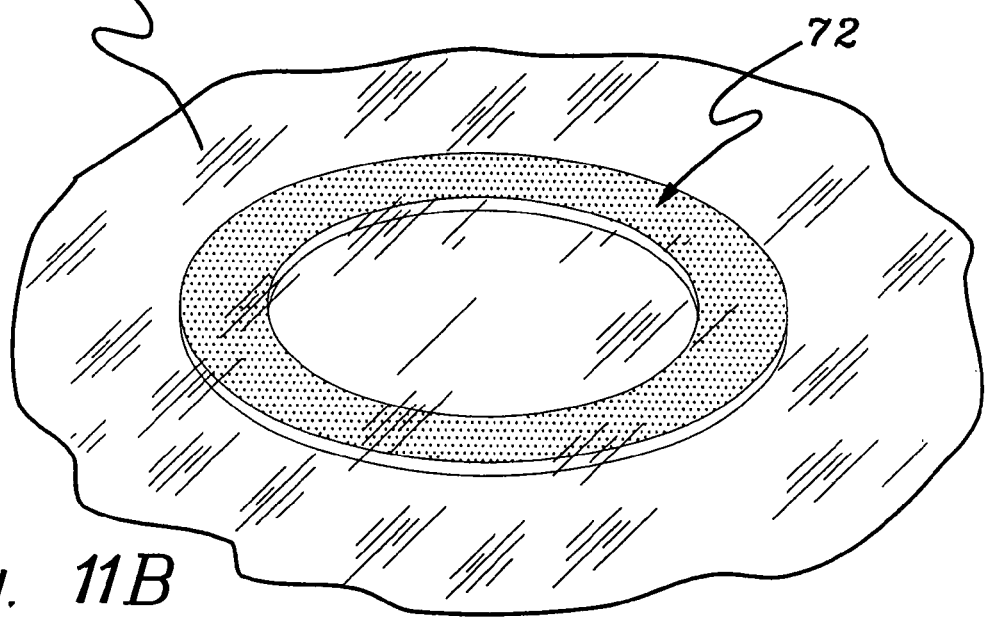
FIG. 11B is a pictorial view of support (72) with glue (84) in contact with membrane (35) positioned over support (72).
Figure 11C:
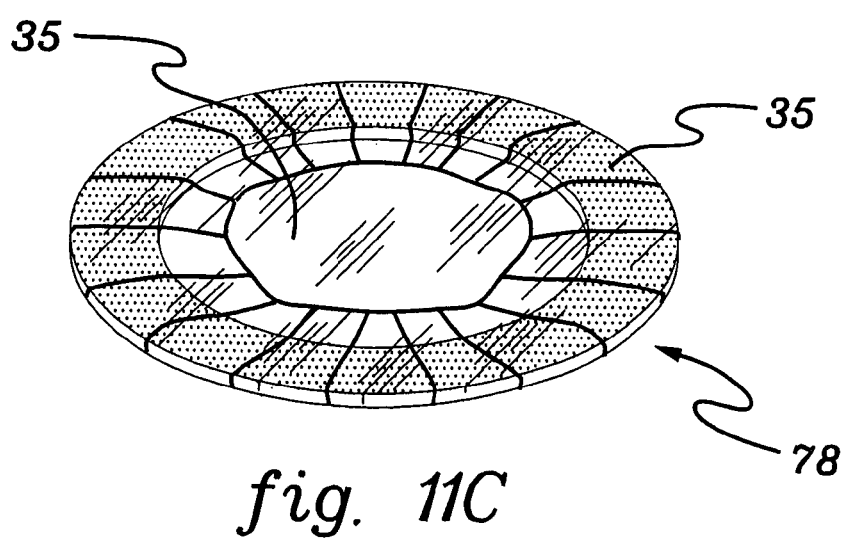
FIG. 11C is a pictorial view of membrane (35) wrapped over support (72) to form an amniotic membrane covering for a tissue surface (78).

In one embodiment of a method and a composition of the invention, as shown in FIGS. 11-12, for example, a membrane is glued to a support. According to an embodiment shown in FIG. 11A, to at least one surface of a support ring (72) having smooth edges is added an adhesive composition (84). Next, as shown in FIG. 11B, the adhesive composition (84) on the surface of support (72) is contacted with an amniotic membrane (35), membrane (35) having a surface with a diameter greater than the outside diameter of support (72). Support (72) is positioned on membrane (35) such that membrane (76) can be folded inwardly over support (72). Membrane (35) is then folded over support (72), as shown in FIG. 11C, such that support (72) is covered by membrane (35) and adheres to membrane (35) by means of adhesive composition (84), thereby making an amniotic membrane covering for a tissue surface (78). In one embodiment of the amniotic membrane covering for a tissue surface the support is a ring. In another embodiment of the covering, the support is a disc. In another embodiment of the covering, the support is a conformer, such as (134) in FIG. 19A. In another embodiment, a double-layered covering is formed by repeating the above-described steps, placing a second piece of amniotic membrane under an amniotic membrane covering for a tissue surface and folding it over the covering.

In one embodiment of the covering the adhesive composition comprises a fibrin sealant (also known as a "fibrin glue") including fibrinogen. In another embodiment, the adhesive composition comprises sinoacralate, chemically known as 2-cyano-3t-(2) furyl-acrylic acid. A "fibrin sealant," as the term is used herein, is a tissue adhesive used during surgical procedures to control bleeding and to seal tissues. A fibrin sealant contains two blood clotting factors, fibrinogen and thrombin, from human plasma. A virally inactivated fibrin sealant suitable for use in an embodiment of the invention is sold under the brand name TISSEEL® (Immuno, Aktiengesellschaft fur Chemischmedizinische Producte Corporation, Austria), available from Baxter Healthcare Corporation (Glendale, Calif.). Another virally-inactivated fibrin sealant suitable for use in an embodiment is available from Vitex Technologies, Inc. (New York, N.Y.).

Figure 12A:
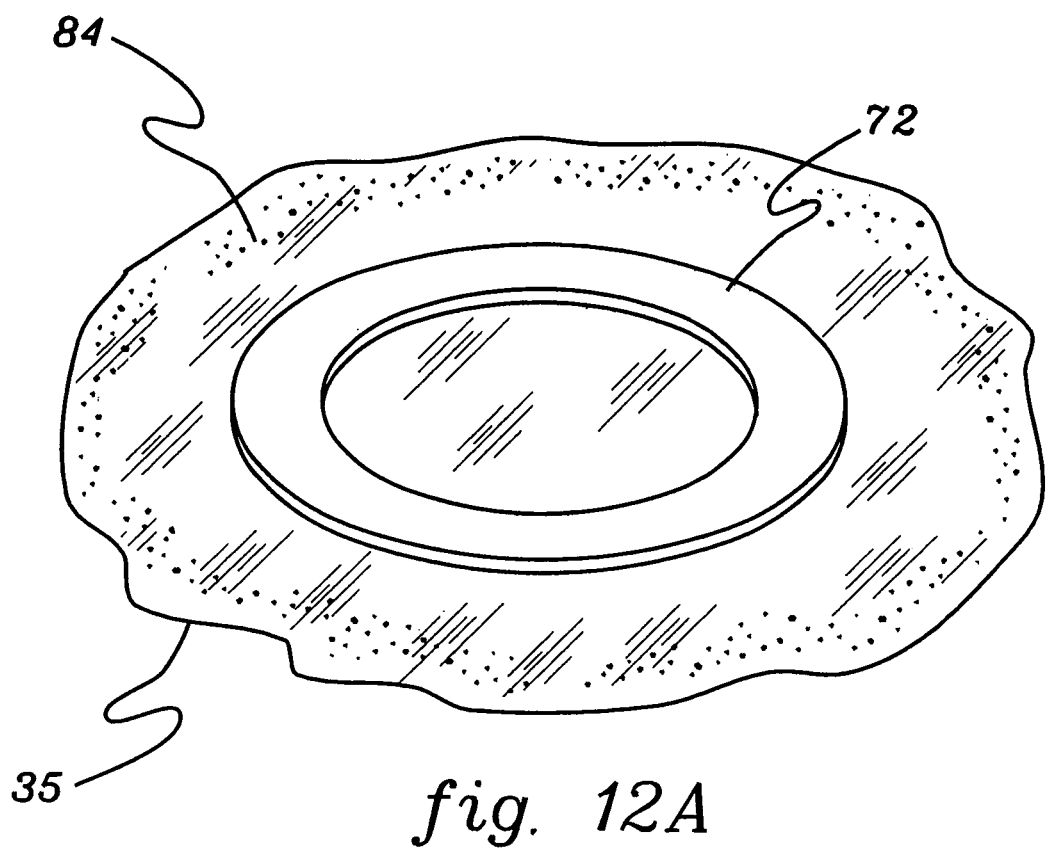
FIG. 12A is a pictorial view of a support (72) placed in contact with membrane (35) to which glue (84) has been added.
Figure 12B:
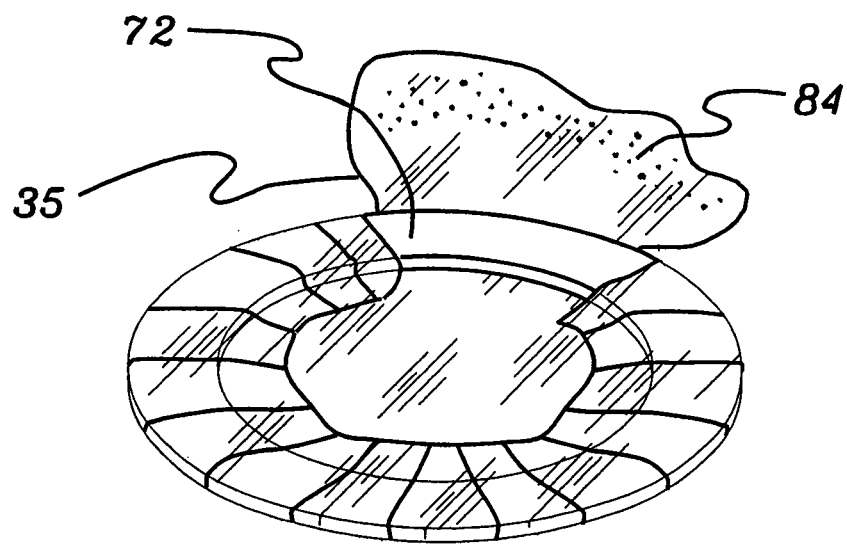
FIG. 12B is a pictorial view of the membrane (35) being wrapped over support (72) to form an amniotic membrane covering for a tissue surface.

Another embodiment of a composition and a method of preparing the composition, an amniotic membrane covering for a tissue surface wherein the membrane is fastened to the support by means of an adhesive composition, is shown in FIGS. 12A and 12B. According to an embodiment of the method, a ring support (72) is positioned on a center portion of amniotic membrane (35), having a surface with a diameter greater than the outside diameter of support (72). An adhesive composition (84) such as a fibrin sealant described above is added to a portion of a surface of membrane (35) that extends beyond the outside diameter of support (72). The outer edge portion of membrane (35) having adhesive (84) thereon is then folded inwardly over the support (72), as shown in FIG. 12B, such that support (72) is covered by membrane (35), and the portion of a surface of the membrane having adhesive composition thereon is glued to another portion of the membrane, thereby making an amniotic membrane covering for a tissue surface. In one embodiment the support is a ring; in another embodiment the support is a disc. In one embodiment the adhesive composition is a fibrin sealant or sinoacralate.

Figure 13:
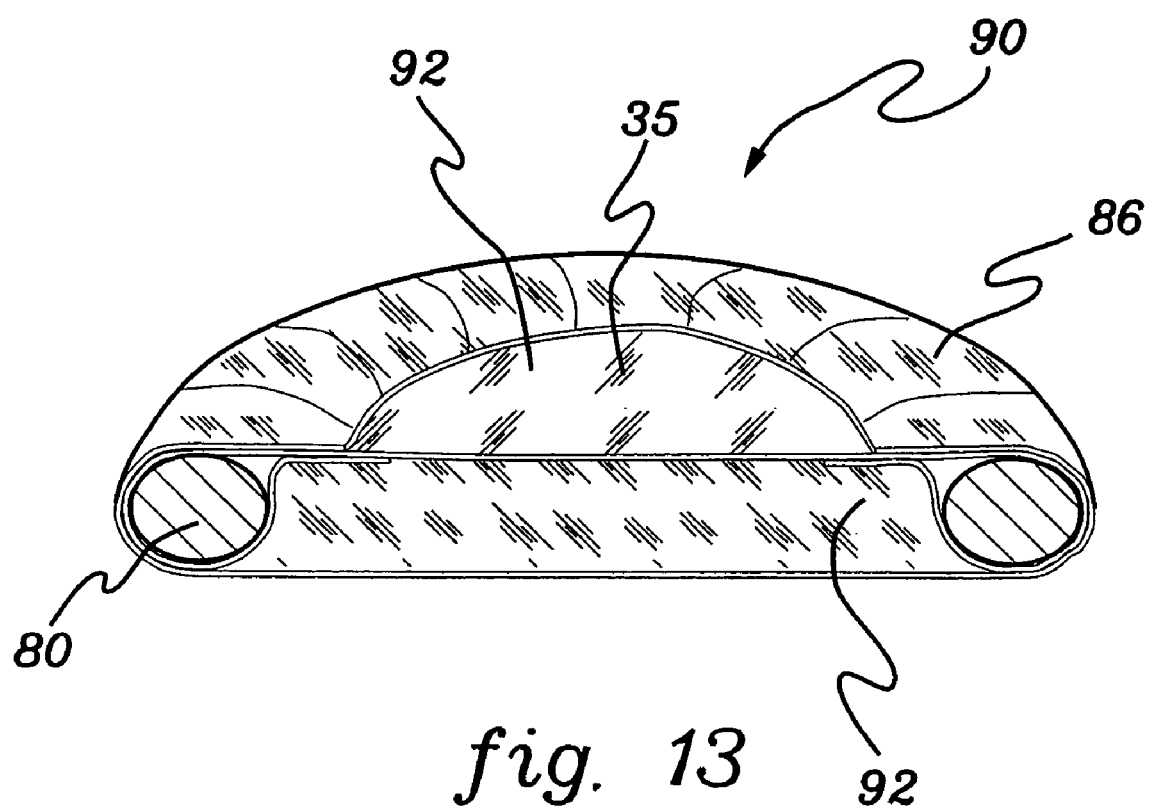
FIG. 13 is a sectional view of two pieces of membrane (35) folded over one support to form a double-layered amniotic membrane covering for a tissue surface (90).

In one embodiment, the method of preparing an amniotic membrane covering for a tissue surface wherein the membrane is fastened to the support by means of an adhesive composition as described above, includes additional steps to make a double-layered amniotic membrane covering for a tissue surface (90), as shown in the sectional perspective view of FIG. 13. The first piece of amniotic membrane (35) covering ring (80) is visible in the sectional view. In this embodiment, a second piece of amniotic membrane (86) is folded over an amniotic membrane covering for a tissue surface to form a pocket (92) that can contain a therapeutic substance. The method includes the additional steps of positioning the amniotic membrane covering for a tissue surface on a center portion of a second amniotic membrane (86) having a surface with a diameter greater than the outside diameter of the amniotic membrane covering; applying an adhesive composition to a portion of the surface of the second amniotic membrane (86) that extends beyond the outside diameter of the amniotic membrane covering; and folding the second amniotic membrane (86) inwardly over the amniotic membrane covering such that the amniotic membrane covering is covered by second amniotic membrane (86), thereby making a double-layered amniotic membrane covering for a tissue surface (90).

According to an embodiment, amniotic membrane can be attached to each of two support rings having a snap together fit, thereby making a double-layered amniotic membrane covering for a tissue surface. For example, amniotic membrane can be attached to each of the support rings shown in FIGS. 4, 5, 6, 7, 8, 9, 10, 11, and 12 and to the support shown in FIG. 20A, thereby making a double-layered amniotic membrane covering for a tissue surface. According to an embodiment, an amniotic membrane covering with or without a pocket may have a perforation to allow trapped air to escape when the covering is applied to a tissue surface. One embodiment of a double-layered amniotic membrane covering for a tissue surface includes one or more therapeutic agents in the space or pocket formed between the two membrane layers.

Figure 14A:
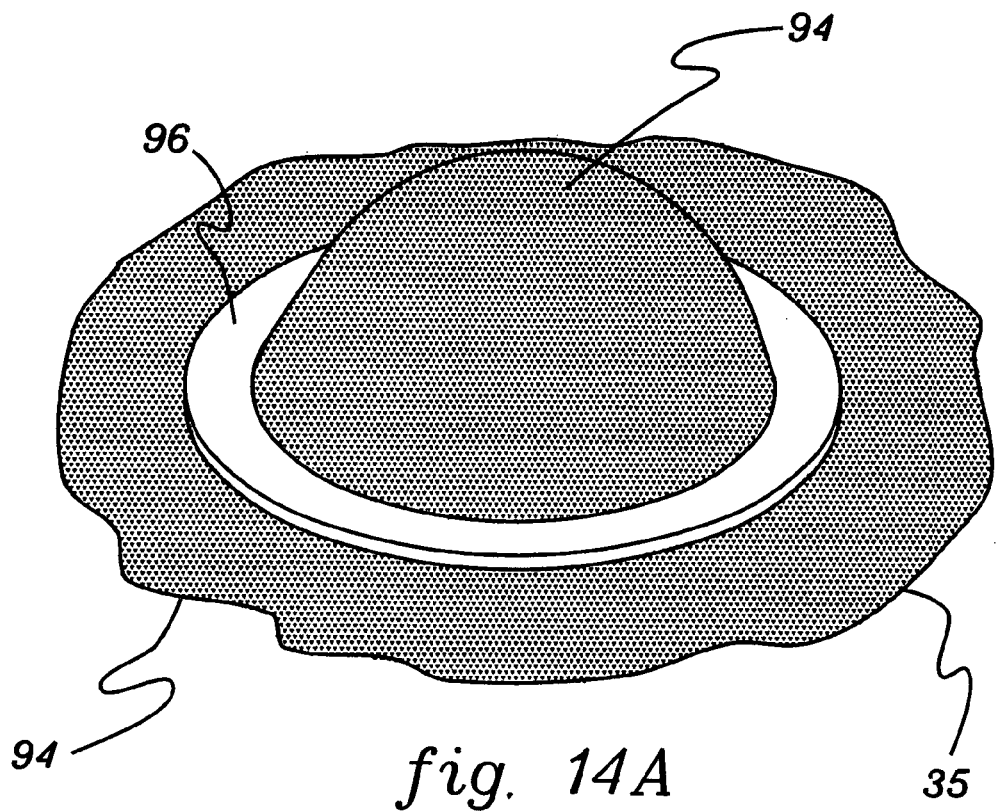
FIG. 14A is a pictorial view of support (96) in contact with a center portion of a stromal side (94) of amniotic membrane (35).
Figure 14B:
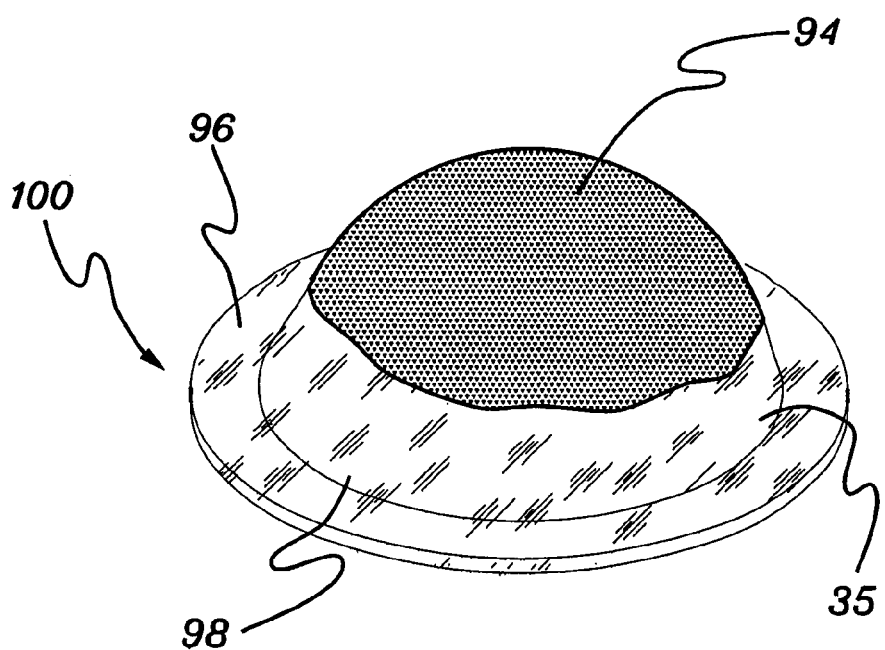
FIG. 14B is a perspective view of an amniotic membrane covering for a tissue surface (100), showing membrane (35) folded over support (96) such that a portion of the stromal side (94) of membrane (35) adheres to another portion of side (94), thereby holding the support in place.

Use of the "Sticky" Stromal Side of Amniotic Membrane to Secure the Membrane on a Support As described above, amniotic membrane has two sides: a thick basement membrane and an avascular stroma. The stromal side of amniotic membrane can be distinguished from the side of the basement membrane by touch with a sponge, such as a WECK-CEL® sponge (Edward Weck, Incorporated, Princeton, N.J.). The stromal side is sticky and will adhere to the sponge. The adhesive nature of the stromal side of amniotic membrane can be employed to make a composite according to another embodiment of the invention, as shown in FIGS. 14A and B. In this embodiment, an amniotic membrane covering for a tissue surface (100) includes support (96) having an outside diameter; amniotic membrane (35) having a surface with a diameter greater than the outside diameter of support (96), and having a stromal side (94); support (96) positioned on a center portion of the stromal side (94) of membrane (35), membrane (35) folded inwardly over support (96) during assembly such that support (96) is covered by membrane (35), and a portion of stromal side (94) of the folded membrane adheres to another portion of stromal side (94) of membrane (35), due to the stickiness of the stroma, thereby holding support (96) in place and making an amniotic covering for a tissue surface. In FIG. 14B, the non-stromal side (98) is visible where the amniotic membrane is folded up over support (96). According to an embodiment the support is a ring or a disc or a conformer.

Figure 14C:
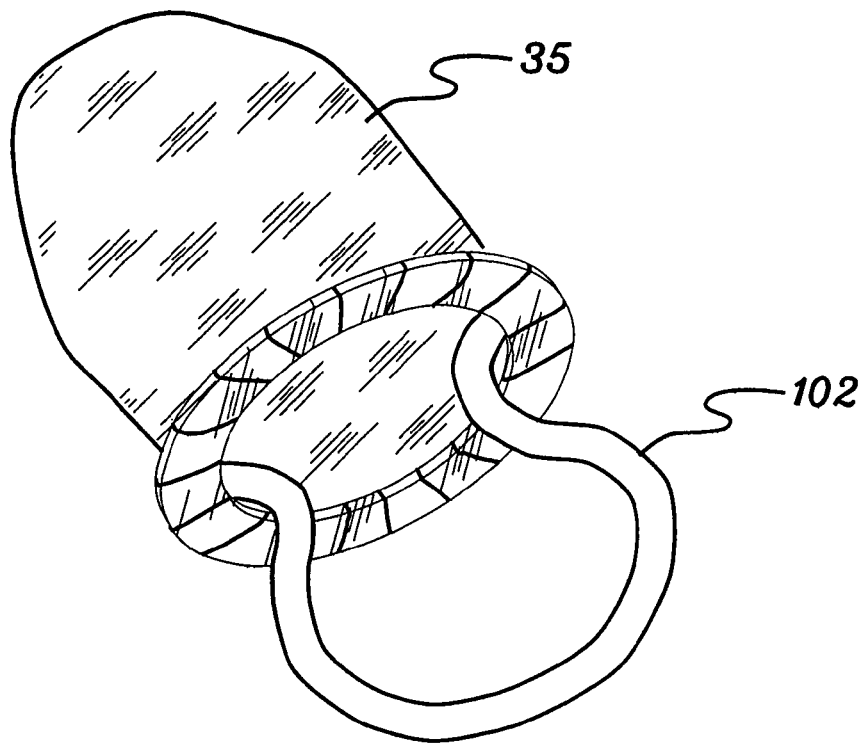
FIG. 14C is a pictorial view of covering (100), with a flexible O-ring (102) being inserted under the covered support.
Figure 14D:
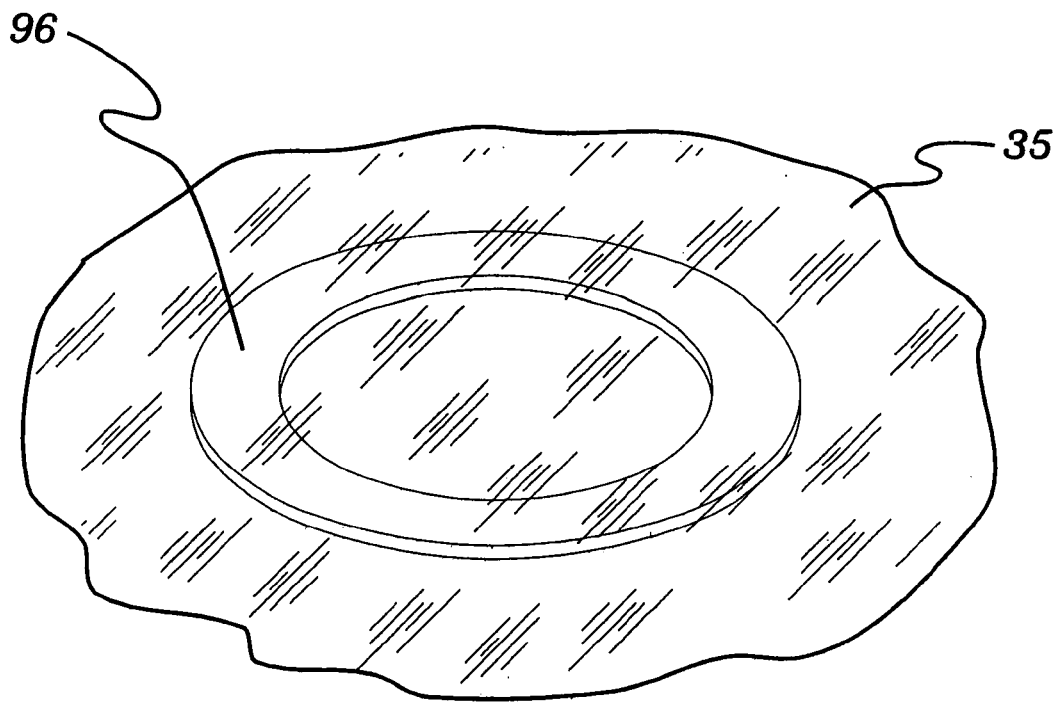
FIG. 14D is a perspective view of an amniotic membrane (35) positioned over a support (96).
Figure 15A:
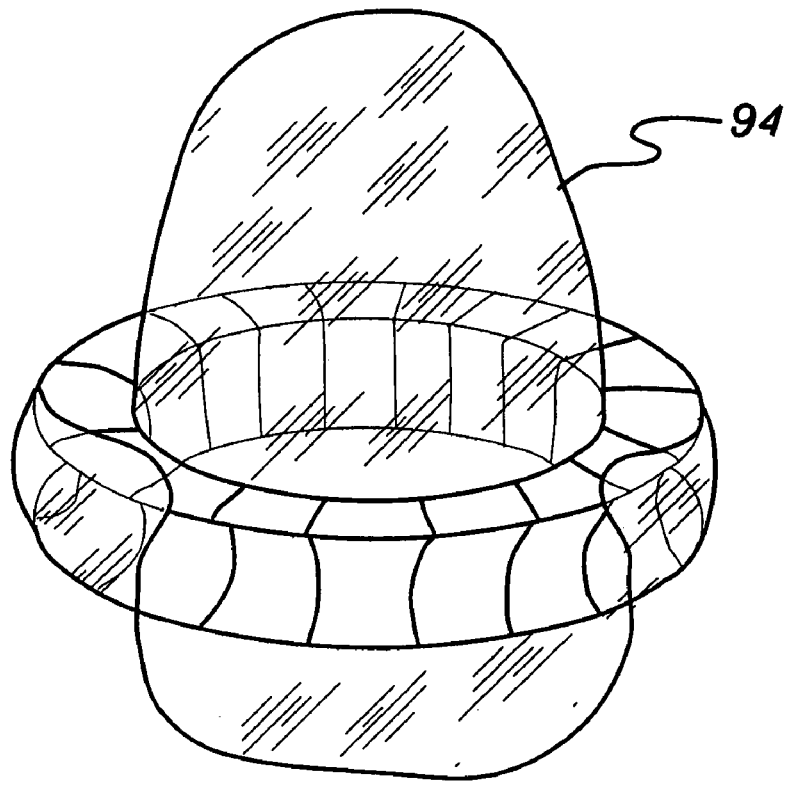
FIG. 15A is a perspective view of an amniotic membrane (35) being wrapped around a support.
Figure 15B:
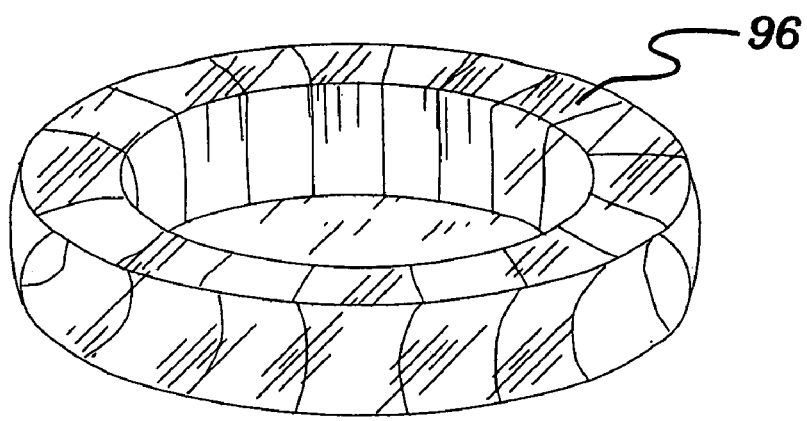
FIG. 15B is a perspective view of a wrapped support shown in FIG. 15A.
Figure 15C:
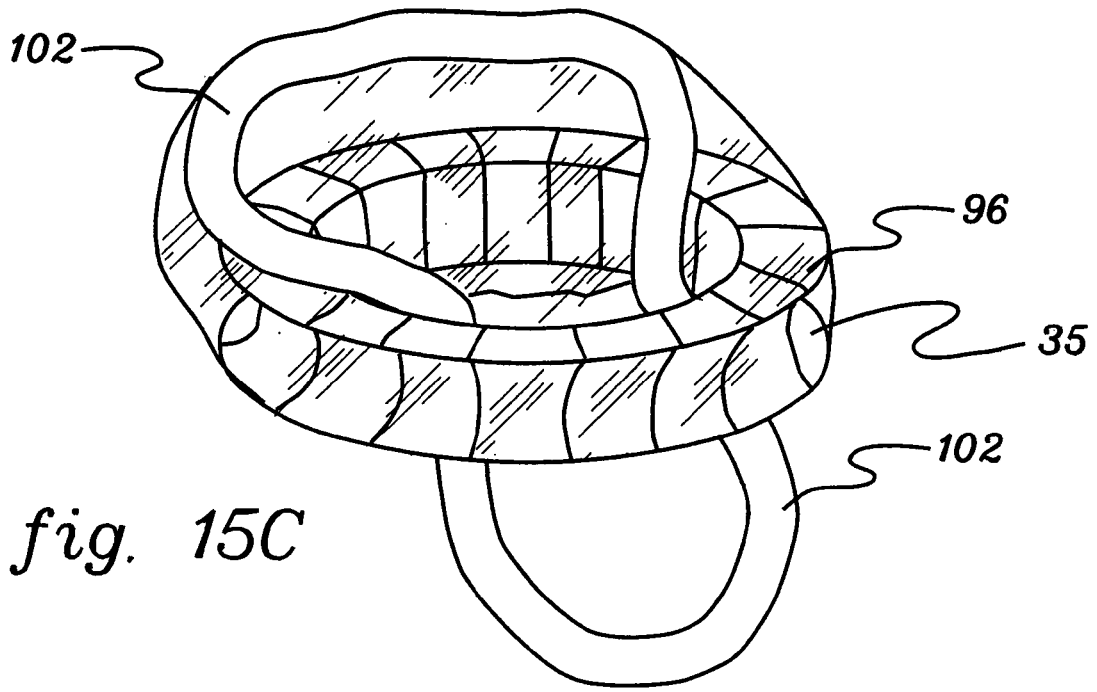
FIG. 15C is a perspective view of a flexible O-ring (102) being inserted inside the support of the amniotic membrane covering for a tissue surface of FIG. 15B.
Figure 15D:
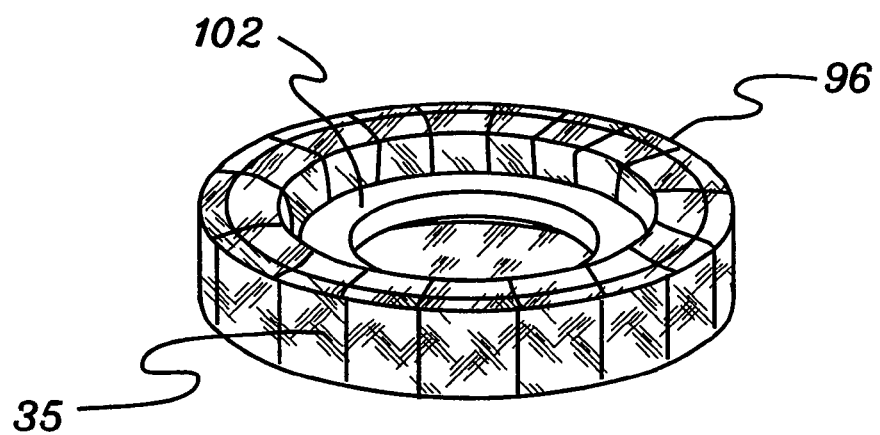
FIG. 15D is a pictorial view of the covering for a tissue surface showing the O-ring (102) seated inside the support.

As shown in FIG. 14C, according to another embodiment, a second support (102) is inserted under the covered support, and second support (102) is positioned for contacting at least a portion of the amniotic membrane covering the support, thereby securing the amniotic membrane between the covered support and second support (102).

FIGS. 15A-B and 15C-D are alternate representations of the embodiment shown in FIG. 14.

Use of a Clamping Ring to Secure a Membrane

Figure 16A:
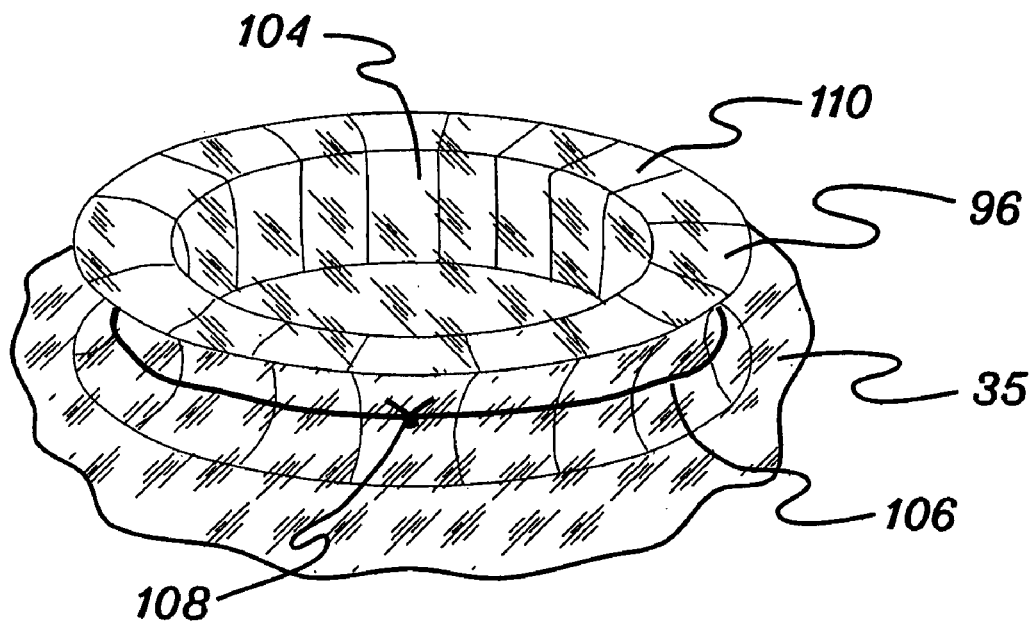
FIG. 16A is a pictorial view of an amniotic membrane covering for a tissue surface showing membrane (35) secured on a grooved ring support (96) with a suture thread (106).
Figure 16B:
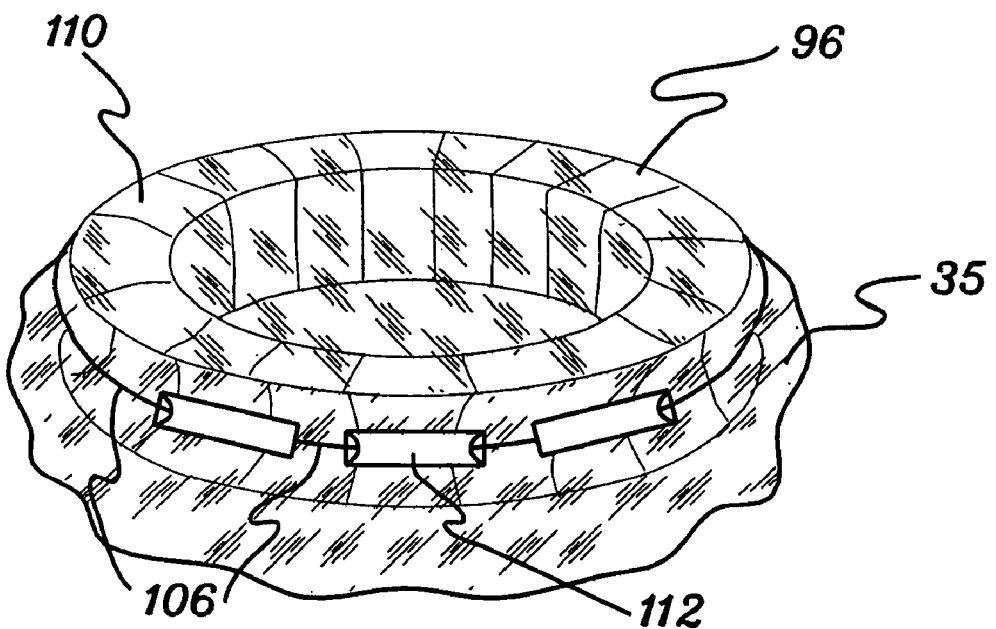
FIG. 16B is a pictorial view of an amniotic membrane covering for a tissue surface depicting membrane (35) secured on a grooved ring support (96) with a clamping ring (112) and sutures (106).

FIGS. 16A-16B depict other embodiments of an amniotic membrane covering for a tissue surface or a culture insert. In the embodiment shown in FIG. 16A, amniotic membrane (35) is positioned over support ring (96) including a peripheral, annular groove; a suture thread (106) is positioned in the groove, and tied with a knot (108) around membrane (35) to secure membrane (35) to support (96). In another embodiment, the support ring does not have a peripheral, annular groove. In yet another embodiment, the membrane is sutured directly to the support.

In the embodiment depicted in FIG. 16B, a clamping ring (112) is positioned in the groove of support ring (110) and clamped in place. Many types of clamping rings are suitable for use in this embodiment of the invention, provided that they have smooth surfaces that will not tend to tear the membrane. An amniotic membrane (35) having a diameter larger than the outside diameter of support ring (96) is then positioned over clamping ring (112). Membrane (35) is then pulled into clamps (112) on ring (96) with a suture thread (106), thereby securing membrane (35) to support ring (110). Suture thread (106) may be tied in place, and may be removed by pulling on an end of the thread. In an alternate embodiment, the amniotic membrane (35) is placed over support ring (96) before clamping ring (112) is attached. Clamping ring (112) is then positioned over membrane (35) and into the groove of support ring (96) and clamped in place, thereby securing membrane (35) to support ring (96).

Use of Slits in the Support, Clips, or Tacks to Secure a Membrane

Figure 17A:
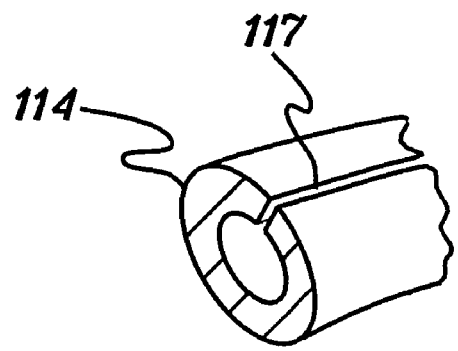
FIG. 17A is a partial sectional view of a hollow support ring (114) having a surface defining a slit (117).
Figure 17B:
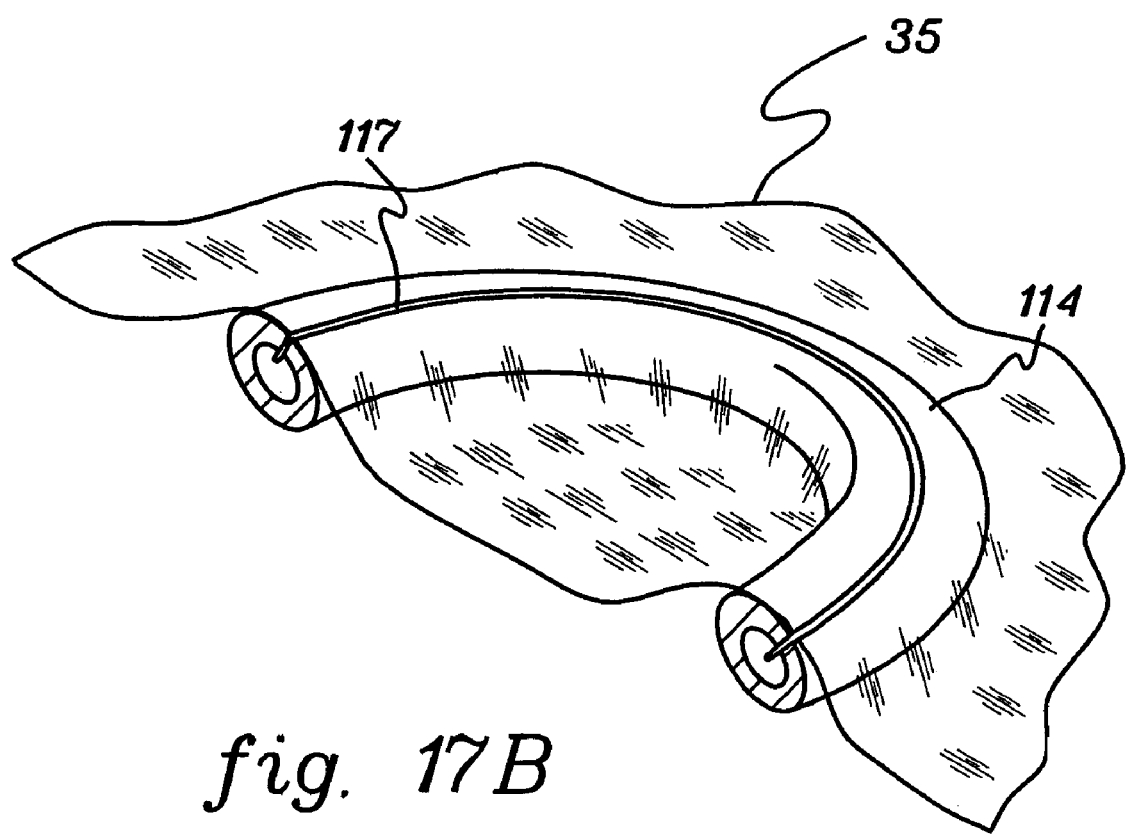
FIG. 17B is a perspective view of ring (114), covered loosely by membrane (35), with portions of membrane (35) pressed into slit (117).
Figure 17C:
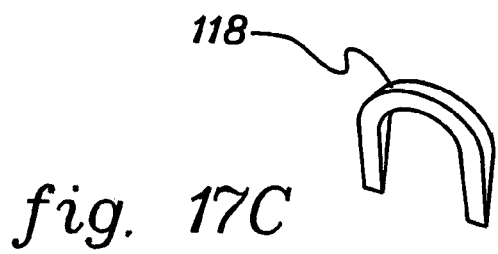
FIG. 17C is a pictorial view of a clip.

FIGS. 17A and B shows an embodiment of the invention wherein the surface of a support ring (114) to be contacted with amniotic membrane (35) defines a slit (117) or cavity. FIG. 17A is a perspective sectional view of a portion of ring (114). Amniotic membrane (35) is placed over ring (114), and a vacuum is used to pull membrane (35) into slit (117). Alternatively, membrane (35) is pushed into slit (117).

Figure 17D:
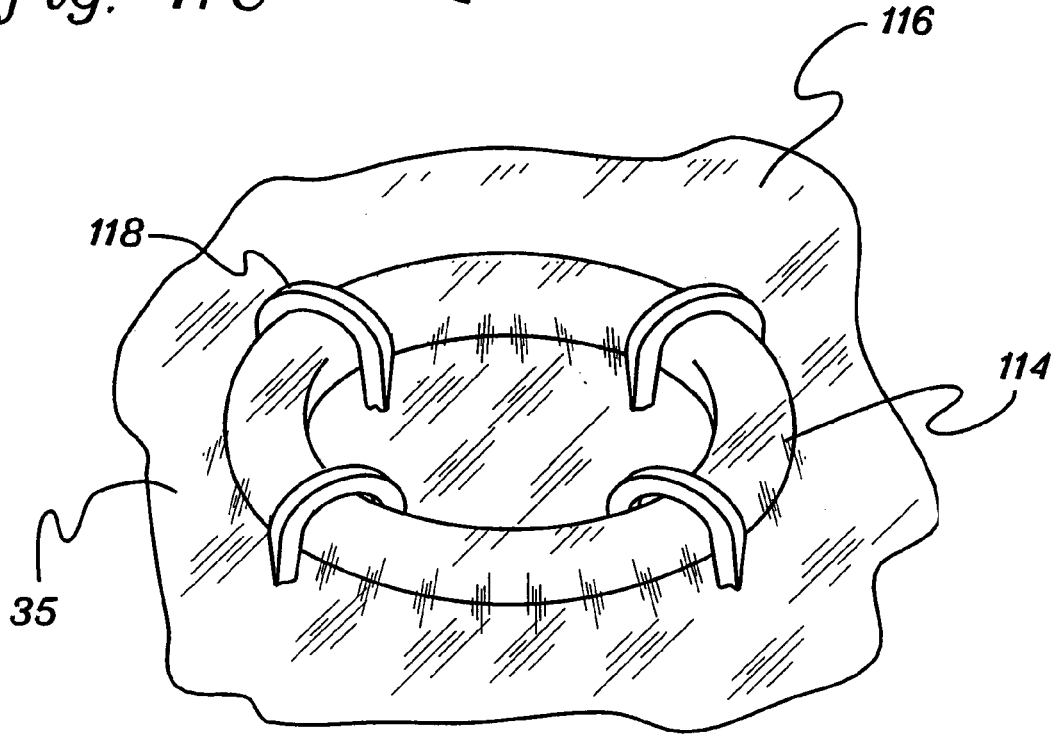
FIG. 17D is a perspective view of a culture insert showing membrane (35) secured on a ring support (114) with clips (118).

As shown in FIG. 17D, a clip (118) is used to secure the membrane (116) to the support ring (114). Clip (118) can be crimped to more securely hold membrane (116) onto support ring (114). Clips (118) are made of biocompatible materials such as, for example, plastic, stainless steel, platinum, or gold.

Figure 17E:
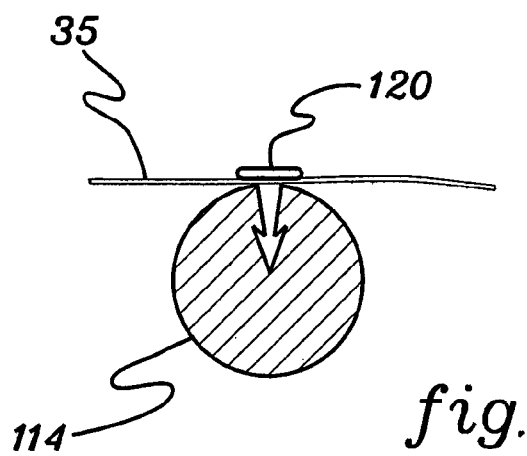
FIG. 17E is a partial sectional view of ring (114) covered by membrane (35) secured to ring (114) with a tack (120).

In an alternate embodiment, shown in FIG. 17E, a tack (120) with a burred tip, the tip made of a biocompatible material, is used to pierce membrane (35) and support ring (114), securing the membrane (35) to support ring (114).

Use of a Biopolymer Covering for a Tissue Surface to Treat a Target Tissue

A biopolymer covering for a tissue surface, such as an amniotic membrane covering for a tissue surface according to an embodiment of the invention can be placed on a target tissue for therapeutic treatment of tissue. The covering according to an embodiment is allowed to remain in place on the tissue for a sufficient period of time to bring about a noticeable improvement in the condition of the tissue. The invention provides a composite and a method for treating tissue, and alleviating pain, reducing inflammation, swelling, and scarring, accelerating healing of burns and wounds, and otherwise treating diseased or injured tissue, by applying to the surface of the affected tissue an amniotic membrane covering for a tissue surface.

The stroma of amniotic membrane contains growth factors, anti-angiogenic and anti-inflammatory proteins, as well as natural inhibitors to various proteases. These factors diffuse out of the amniotic membrane placed in contact with a tissue surface, and appear to accelerate the healing process. The cornea, for example, is considered to be at least partially "healed" when it has been re-epithelialized. Thus, an embodiment of a tissue covering of the invention can be used as a dressing over skin wounds, for ocular surface reconstruction, for treating a corneal epithelial defect or stromal ulcer, and can be implanted at a target tissue site to prevent adhesion in surgeries or to reconstruct soft tissues.

A tissue covering according to an embodiment of the invention can be impregnated with cells grown thereon or attached thereto, and used as a scaffold for in vivo tissue reconstruction or for gene therapy. Therapeutic substances, as described above, can be included in the membrane or in the support, in particular a biodegradable support, and the tissue covering according to an embodiment of the invention can be used as a sustained or controlled release drug delivery vehicle.

The membrane and support of any tissue surface covering according to an embodiment of the invention can be each sized for placement on a surface of the eye or on a surface of tissue including dermal tissue, gastrointestinal tract tissue, respiratory tract tissue, genital system tissue, urinary system tissue, circulatory system tissue, and bone tissue. As such, the support of a tissue surface covering of an embodiment of the invention has a radius of curvature corresponding to a measured base curve of a body tissue, for example, a cornea, which is to be contacted with the tissue surface covering.

In an embodiment of a tissue surface covering of the invention comprising a support and a membrane, the support is compliant with the target tissue. As used herein, the terms "compliant," "compliance," and grammatical variations thereof, refer for example to the ability of the support to closely match the mechanical and physiological properties of the target tissue.

A Kit: an Embodiment of the Invention

A kit according to an embodiment of the invention can comprise any combination of compositions or devices of the invention such as, for example, membranes, films, elastic bands, supports, rings, tissue sealants, suture threads, clamping rings, clips, tacks, conical shaped expanders, and apparatuses for frictionally engaging a radially elastic band placed over the apex of an expander.

Figure 18A:
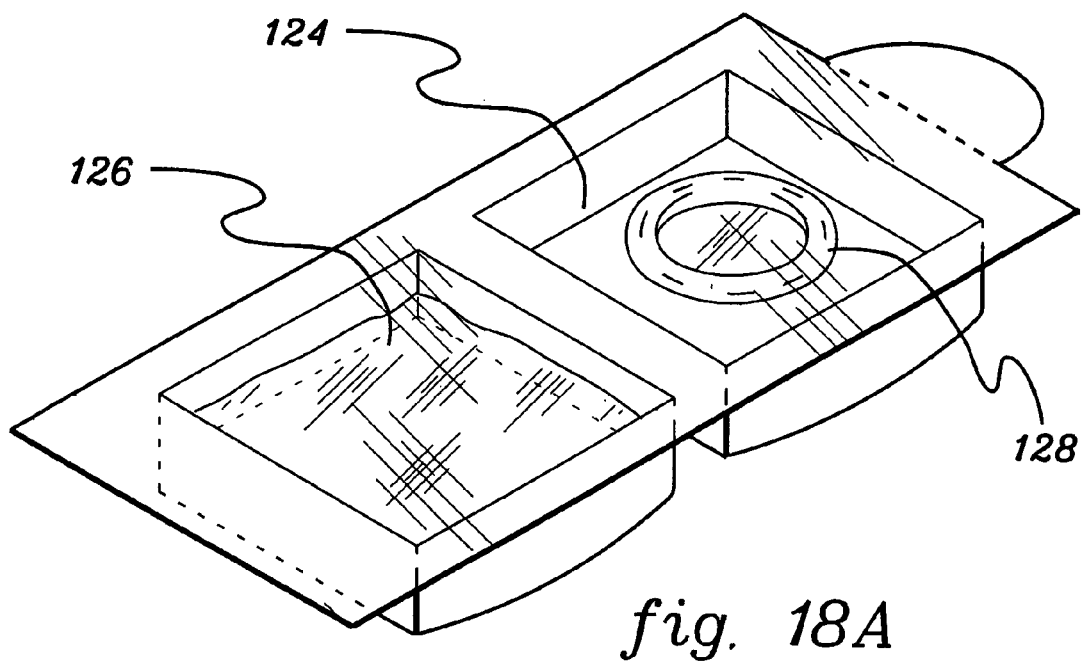
FIG. 18A is a pictorial view of a sealed package for a dry-freeze membrane (128), the package having a re-hydrating solution in compartment (126) and membrane (128) in compartment (124).
Figure 18B:
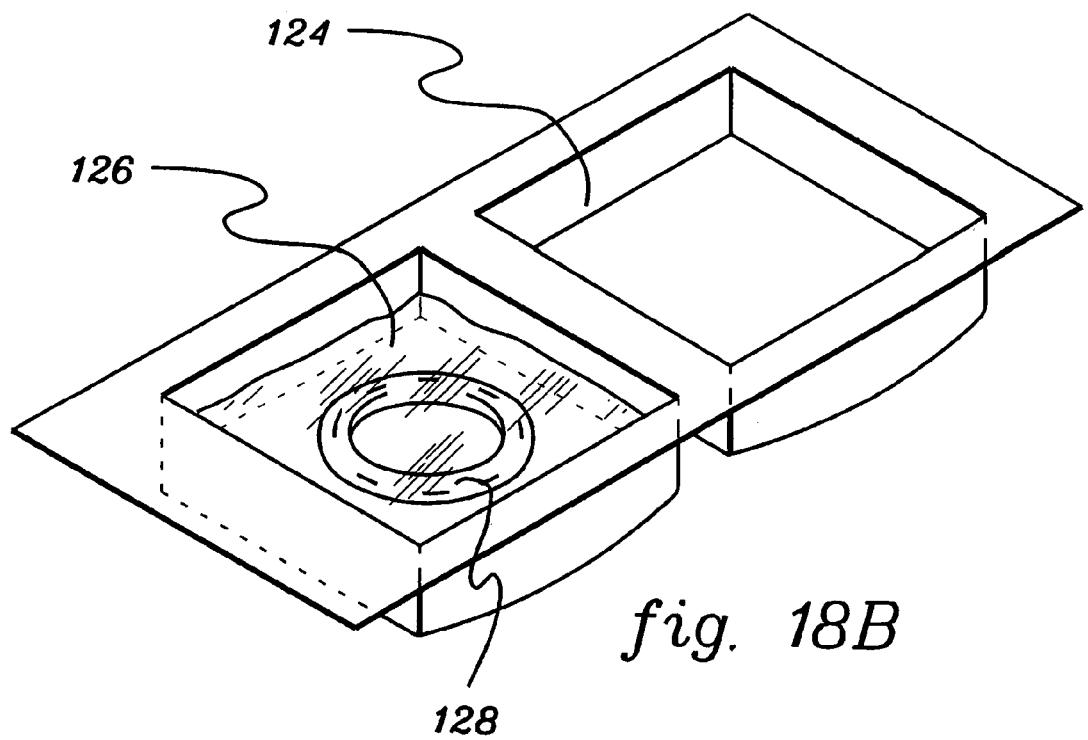
FIG. 18B is a pictorial view of the package of FIG. 18A with the seal broken and membrane 128 positioned in the re-hydrating solution.

An embodiment of the invention is a sealed package containing an amniotic membrane covering for a tissue surface. One example of this embodiment is a sealed package having two sealed compartments, as shown before the seal is broken, in FIG. 18A. One compartment (124) contains a freeze-dried amniotic membrane covering for an ocular surface (128), to be used as a bandage contact lens. The other compartment (126) contains a medium to hydrate the bandage contact lens (128). FIG. 18B shows the package after the seal is broken, and the bandage contact lens (128) being hydrated in compartment (126).

Figure 19B:
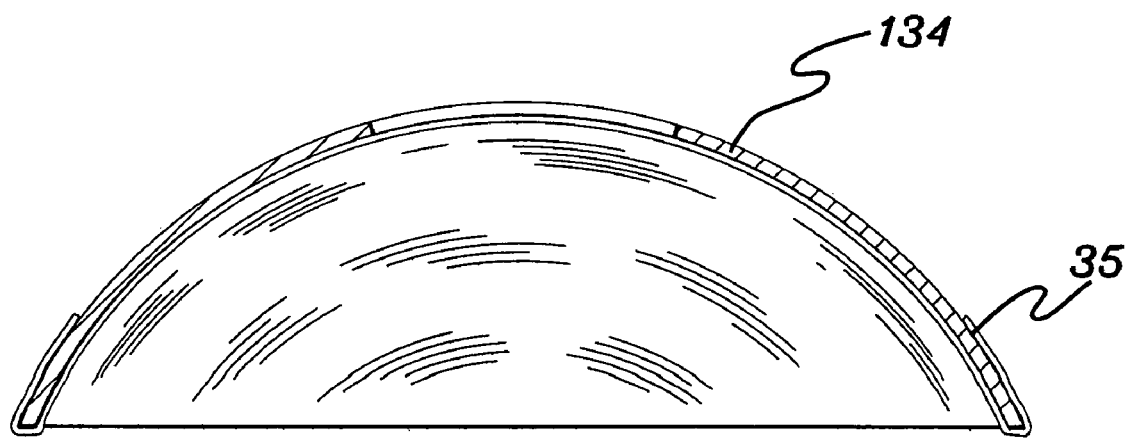
FIG. 19B is an elevational view of the covering for an ocular surface shown in FIG. 19A.

FIG. 19A is a perspective view of a support (134) shaped to fit over an ocular surface, the support having an adhesive composition (84) as previously described on a portion of the outer peripheral surface, and amniotic membrane (35) positioned on the inner surface or the concave side of support (134). As depicted in FIG. 19B, membrane (35) is positioned over the inner surface of support (134) and folded up and over the outer peripheral surface, such that membrane (35) is in contact with adhesive composition (84) and membrane (35) is held in place by composition (84).

In another embodiment, support (134) has a peripheral groove (not shown) on the outer surface; membrane (35) is positioned on the inner surface of support (134), and folded up to cover the outer peripheral edge of support (134) and the peripheral groove. To hold membrane (35) against the inner surface of support (134), a second annular support, concentric with support (134) and having an edge designed to snap-lock in the peripheral groove of support (134) is positioned over support (134) and snap-locked in place with support (134), thereby fastening membrane (35) to the support.

As described above, the amniotic membrane and supports required to fabricate a culture insert or a covering for a tissue surface can also be supplied as components of a kit according to an embodiment. In addition, the kit according to a particular embodiment includes samples of one or more antibacterial compositions and therapeutic substances to be added to the amniotic membrane or administered with the use of the amniotic membrane covering for a tissue surface.

The invention is described in further detail in the following examples. These examples are given by way of illustration and are not intended to limit the invention in any way.

The solid support used in the three prototypes described below can be changed with respect to materials, dimension, and shape in order to fulfill various purposes.

All of the three prototypes described below can be used for culturing cells in vitro. Furthermore, therapeutic genes can be incorporated in cultured cells during in vitro growth so that these prototypes can then be used as a means to deliver the cultured cells over-expressing a gene of interest for a potential gene therapy in the future.

The prototypes can be modified as described previously, with no more than routine experimentation, so that the shape will fit well on the ocular surface.

The prototypes can be used to deliver cultured cells ex vivo, the cells expanded for a therapeutic reason.

Exemplification:

Prototype 1: Fastening Amniotic Membrane to a Culture Insert

Prototype 1 consisted of a set of devices shown in FIGS. 1A-1D and FIGS. 2, 3A and 3B. The devices include a conical shaped expander, as shown in FIGS. 1A-1D (20) and FIG. 2; an apparatus (30) for engaging the elastic band (24), and a ring for transfer of the elastic band to the insert (shown in FIGS. 1A-1D at base of expander (20). The original purpose of these devices is to facilitate the fastening of amniotic membrane onto a culture insert so that cells can be cultured on the amniotic membrane substrate. Therefore, prototype 1 illustrates how amniotic membrane was fastened on a solid support, i.e., the culture insert, by an elastic band. The operation of these devices to create prototype 1 involved the following steps depicted in FIG. 1A-1D.

Step 1: An elastic band (24) was placed over the apex of a conical shaped expander (20), while the base of the expander was in contact with a ring having a peripheral annual groove for receiving the band (FIG. 1A).

Step 2: An apparatus (30) was used for frictionally engaging the elastic band while applied over the apex of the expander (FIG. 1A).

Step 3: The apparatus (20) was used to urge the band in a direction from the apex of the expander toward the base of the expander, and into the peripheral annual groove on the ring (FIG. 1B-1D).

Step 4: An amniotic membrane was placed on the surface of an insert.

Step 5: The ring was then lifted to apply over the membrane on the insert.

Step 6: The band was translocated from the ring to the insert (See FIG. 4D).

Prototype 2: Fastening Amniotic Membrane between Two Rings with One Being an O-ring The prototype 2 is depicted in FIGS. 4A-4D and in FIGS. 5A-5D. The prototype comprises two sets of rings, with one being a solid support, while the other is an elastic O-ring (FIGS. 4A and 5A). In this prototype, an amniotic membrane (35) was fasten to a solid support (22), a solid ring, which has an annular groove (21 or 23) in the inside or outside surface of the ring (22), so that it can be sized to receive an elastic O-ring (24 or 25). The operation involved the following steps depicted in FIGS. 4 and 5.

Step 1: The amniotic membrane (35) was placed on the solid ring (22) with a groove (24) in FIG. 4D, or (21) in FIG. 5D.

Step 2: The elastic O-ring (24 or 25) was transferred to the solid ring support (22) to secure the membrane (35) by being inserted into the outside groove (23) of the ring (FIG. 4D), or the inside groove (21) of the ring (FIG. 5D).

Prototype 3: Fastening Amniotic Membrane between Two Solid Rings by a Snap Mechanism The prototype 3 is illustrated in FIGS. 8A-8D and FIG. 9A-9D. The prototype included the fabrication of a polymer ring, which has a cut slit (45) in FIG. 8 and (50) in FIG. 9. The operation involved the following 4 steps depicted in FIG. 8A-8E.

Step 1: The amniotic membrane (35) was applied onto the surface of the ring (FIGS. 8A-8C), and pushed into the slits along the outer edge of the ring. This operation was performed while the ring was in a mold (44) so that the membrane could droop or drape downward in the middle. The ring (46) with loosely adherent membrane was then lifted out of the mold by a forceps (FIG. 8B). On a solid supporting board, a pressure was applied to twist the ring by inner or outer rotation so that the membrane covered this ring completely (FIG. 8D). This action allowed the fastening of the amniotic membrane to the ring (FIG. 8E).

Experimental Design and Methods

Aim 1: To develop an amniotic membrane covering for an ocular surface, or "bandage contact lens" by modifying the existing prototypes based on the shape of a conformer to be fitted to cover the corneal surface and the entire ocular surface, respectively.

1) Rationale:

Our preliminary studies have demonstrated that amniotic membrane can be fastened onto several kinds of solid supports. Therefore, we believe that it is also feasible to develop a sutureless "bandage contact lens" by modifying the solid support based on the experimental design proposed below so that it can be applied to cover the corneal or the entire ocular surface.

2) Experimental Design:

The design of the bandage contact lens of the invention will require resolving the following three key issues.

The first issue is the size of the "lens." Based on the pathology of the ocular surface to be treated, the bandage contact lens will need to cover either the entire corneal surface for treating corneal diseases or the entire ocular surface for treating diffuse ocular surface diseases involving both the cornea and the conjunctiva. Therefore, we will design at least two bandage contact lenses for either corneal uses (e.g., 15 mm) or the entire ocular surface uses (e.g., up to the conjunctival fornices).

We will adopt the shape (or contour) of a conformer. A conformer is a plastic shell to be fitted in the space between the eyelids and the ocular surface. Different sizes of conformers are commercially available. Conformers (also known as SYMBLEPHARON RING) were obtained from Jardon Eye Prosthetics, Southfield, Mich., and are made of acrylic resin known as LUCITE® (polymethylmethacrylate, PMMA) (Dupont de Nemours) that is also used to make hard contact lenses. The current design of conformers and contact lenses does not cause any edge problem in patients wearing them.

A conformer is frequently used by oculoplastic surgeons at the end of the reconstructive surgery to prevent the postoperative formation of symblepharon, i.e., fibrotic adhesion between the tarsal conjunctiva of the eyelid and the bulbar conjunctiva of the globe.

The second issue is the material used to make the solid support for fastening the amniotic membrane. Either acrylic, silicone elastomer, or a combination of both will be tested for making the support.

The third issue is further testing of the mechanism to fasten the amniotic membrane to the solid silicone support, including either the use of acrylic and silicone elastomer according to Prototype 2 mechanism or a flexible silicone rubber (polydimethylsiloxane, trimethyl terminated) support where slits will be made in the inner aspect of the O-ring support, using Prototype 3 mechanism.

The O-ring support will be made of silicone rubber (Material to be 50±5 or 75±5 Shore A class, translucent, base material certifiable to USPCL VI, all other ingredients within FDA guidelines). The length, depth, and width of each slit, in and through the circumference of the skirt, will be varied to provide the best fastening of amniotic membrane to the skirt.

By considering the aforementioned three issues, we propose to develop the bandage contact lens of the invention for corneal or ocular surface use in the following ways.

First, based on the Prototype 3 mechanism, different sizes, i.e., from 13, 15, 17 and 19 mm O-rings made of silicone will be obtained (DA/PRO RUBBER INC., Tulsa, Okla.). Under a microscope, the O-ring will be placed on a rotational stage and affixed in a groove. A blade will be used to create slits at different intervals through the inner surface of the O-ring. Also various depths and lengths of the slits will be tested to see which will provide the best fastening of the amniotic membrane.

Second, based on the Prototype 3 mechanism, we will develop a mechanical guide that will spread the slit open allowing the insertion of the peripheral edge of amniotic membrane into the slit. The mechanism will be similar to a smooth edge vacuum needle.

Third, we will use an O-ring that has the contour of the rabbit eye surface, similar to the human conformer for ocular surface use in Aim 3 rabbit testing, while a circular configuration with the contour resembling that of a contact lens will be adopted for corneal use.

3) Anticipated Results & Interpretation:

The aforementioned experimental designs are highly achievable with no more than routine experimentation, based on our experiences described in the Preliminary Studies. We anticipate that amniotic membrane will be tightly fastened to the solid support for both corneal and ocular surface uses. We also expect that the strength of fastening should be strong enough to withstand the stretch applied to the membrane. To quantify such strength of the bandage contact lens in vitro, we will use a strain-gauge device that will hold a manufactured bandage contact lens of the invention by its outer contour edge and will include a fixture to vary the pressure applied upon the membrane until detachment of the membrane from the O-ring takes place. The stress-strain relation will be recorded on a PC and the break point determined. This device will be used to compare the strength of each bandage contact lens manufactured according to the aforementioned different variables.

4) Potential Problems & Solutions:

Once placed on the eye, the deflection pressure exerted by the tissue is rather small, probably less than 10 grams. If the deflection force as assessed, as described above, prematurely separates amniotic membrane from the silicone O-ring, we will first change the O-ring durometer from 50 to 75 to improve the union between the O-ring and the skirt.

If there is a statistical difference in these various designs, we will choose the one that gives the highest breakpoint. If, however, even if the one with the highest break point is not strong enough, we will change the configuration of the O-ring cross-section from circular to oval and, if need be, change the ring from a circular to an oval lumen so that the edge will become more tapered as it increases the amount of membrane inserted.

If, however, after changing the O-ring durometer/hardness and aforementioned alteration in the slit dimension and shape, we still do not achieve satisfactory fastening, we will change the fastening mechanism to Prototype 3, and the material for making the skirt will be changed from silicone to PMMA and silicone. That is, the fastening will be operated by an O-ring fitting in a groove made in the inner edge or the outer edge of the PMMA skirt. The breakpoint pressure will be measured and compared to see if the fastening strength has been improved.

If, however, the design based on Prototype 2 is not satisfactory in fastening amniotic membrane to a PMMA skirt, we will abandon the O-ring approach altogether, and design a two cavity injectable mold to create the two pieces of the skirt that will snap together. The mold will be manufactured either by Small Parts Inc., Miami Lakes, Fla., or by Innovia Inc, Miami, Fla. When snapped together, these two pieces sandwich and fasten the amniotic membrane, resulting in the original shape and thickness of the conformer shown in FIGS. 20A and B and 21A and B.

The snapping mechanism will be one of the following, all previously described and illustrated in the accompanying drawing: 1) fitted groove on the inner side of one piece and a raised flange on the outer side of the other piece; 2) male and female union with posts created on one piece and holes created on the other piece; or 3) serrated surface on one piece and complementary surfaces on the other.

The edge of a bandage contact lens is fashioned according to the design of the conformer to avoid any potential side effect to the ocular surface that could be created by friction (chafing) during lid blinking. If there is such a concern, we will enwrap the excess amniotic membrane around the outer edge of the solid support so that only amniotic membrane is in contact with the eye tissue.

Aim 2: To examine the durability and stability of manufactured bandage contact lens after cryopreservation 1) Rationale:

Once the bandage contact lens is successfully manufactured for both corneal and ocular surface uses, we will need to examine its durability and stability following a certain period of cryopreservation at the temperature of $-80°$ C. and in the preservation medium, which was described in our proprietary method (see U.S. Pat. No. 6,152,142 incorporated herein by reference) of preparing AmnioGraft™, currently made by Bio-Tissue. The potency of the anti-inflammatory and anti-scarring effects of amniotic membrane is maintained under such a proprietary method of preservation when AmnioGraft™ is distributed to the end user, i.e., ophthalmic surgeons. For the AmnioGraft™, the period of cryopreservation, i.e., the expiration period, has been determined to be at least one year. Therefore, we will need to determine whether the flexible skirts still maintain their integrity under such a storage condition. If that were the case, we will also need to determine if the fastening strength (as measured by breakpoint pressure) is still maintained after various periods of cryopreservation. Cryopreservation of the amniotic membrane fastened to a support is optional.

2) Design:

We will test whether the integrity of the O-ring chosen and the manufactured bandage contact lens (with a fastened amniotic membrane) are still preserved after long-term cryopreservation. We will place a series of O-rings (of different materials) and made with these same O-rings materials in individual glass vials containing the storage medium normally used for storing AmnioGrafts™. We will store these vials in a deep freezer at −80° C. After various periods of storage, we will examine the integrity of the devices under a dissecting microscope to see if there is any crack or defect, and the original material properties will be assessed using the breaking pressure test and compared to the non-frozen membrane, respectively. The duration of cryopreservation will last for a year one period, but data points will be taken weekly within this period (while the manufacturing process is ongoing—Aim 1).

3) Anticipated Results & Interpretation:

From the preliminary test we performed, namely testing the integrity of 3 types of silicone rubber O-rings (pure PDMS, VITON, and fluorosilicone rubber) at −80° C., we anticipate the flexible support of the bandage contact lens to be stable during the 1-year cryopreservation period, and for the fastening strength to remain sufficiently strong. We will also test the physiological action of such fastened amniotic membrane after storage by testing its ability to support epithelial growth in culture (see Methods), and compared to controls before cryopreservation of AmnioGrafts™ following the same amount of time in cryopreservation.

4) Potential Problems & Solutions:

If, however, we noted that the integrity of the flexible support is threatened by the cryopreservation, we will first determine if this adverse effect is time-dependent, and find out the shortest time that still can keep the assembly intact.

If a shorter time of cryopreservation is needed, we will modify our bandage contact lens manufacturing process using the best material but keeping in mind the limited storage period. If however, we discover that the integrity and the fastening strength of the flexible support are not satisfactory, we will look into other elastomeric materials.

Alternatively, we can fasten the membrane, which has been cryopreserved as AmnioGraft™, to the flexible support immediately before distribution, thus avoiding problems that could be associated with long-term cryopreservation.

Aim 3: To examine the safety of the bandage contact lens when applied on rabbit eyes 1) Rationale:

Once we have obtained a satisfactory bandage contact lens for both corneal and ocular surface uses after completing Aims 1 and 2, we will then examine whether such bandage contact lens can be used safely on rabbit's eye. Aim 3 can be started in parallel with Aim 2 after completion of Aim 1.

2) Design:

The protocol will be carried out in a total of 25 NZW rabbit eyes (27 rabbits will be needed with anticipated 10% attrition rate) to test the safety of manufactured bandage contact lens of the invention. We will use those bandage contact lens made to fit rabbit corneal and ocular surface uses. The design of the bandage contact lens with respect to the size, curvature, and contour will be based on the knowledge that rabbit eyes increase in size with the age. Rabbits will be of 2-3 kg of body weight and of either sex. After inserting the rabbit bandage contact lens on the rabbit eye (the other eye serving as a control), each rabbit eye will be examined twice daily by hand light examination and weekly by slit lamp examination for a period of 3 weeks to see if there is any adverse reaction to the lens wear. Specifically, under the slit lamp we will look for inflammation, with respect to tissue swelling, redness, and mucus build up of the ocular surface and the external adnexae including the lids and the skin. Furthermore, corneal epithelial integrity will be monitored by fluorescein staining, and if necessary by histology at the end of study.

In addition, we will record the integrity of the inserted bandage contact lens. Specifically, we will look into the integrity of the membrane (whether it is detached or dissolved), the stability of the fastening of the membrane to the solid support, and the position of the bandage contact lens on the eye surface. The duration of wearing bandage contact lens safely will also be determined. The end point of lens wear will occur when there is any fitting problem with respect to the bandage contact lens, the host tissue, or a combination of both. Statistics will be performed by an analysis of variance followed by post-hoc least significant difference tests to evaluate the statistical differences between the groups with respect to: conjunctiva injection (scale 0-4), corneal epithelium damage (fluorescein staining) (scale 0-4), pannus (scale 0-4), and anterior chamber cell flare (scale 0-4) using the standard scale: 0=none, 1=low, 2=mild, 3=strong, 4=severe.

3) Anticipated Results and Interpretation:

We anticipate that the rabbit eye will wear rabbit bandage contact lens well without any complication, and the integrity of the membrane should last for at least one week, preferably up to three weeks, a time interval that has been found to be sufficient to treat human ocular surface diseases using conventional sutured AmnioGrafts™. During this period of time we anticipate that there will not be any fitting problem in the integrity of the bandage contact lens (for both corneal and ocular surface uses), or the rabbit ocular surface tissues and adnexa.

4) Potential Problems & Solutions:

Rabbit eyes differ from human eyes in having a slower blinking rate, and in having an extra nictitating membrane in the nasal bulbar conjunctiva. The former may cause a longer exposure time of the eye surface, leading to the dryness of the membrane on the rabbit eye. In human patients with an exposure problem, we have observed early dissolution of the AmnioGraft™, i.e., shorter than one week. If such an exposure problem in rabbits indeed creates unfavorable testing environment, we will first verify this concern by measuring the blink rate in rabbits before and after insertion of a bandage contact lens. Once confirmed, this problem will be dealt with by performing a small sutured tarsorrhaphy, i.e., closure of upper and lower eyelids by sutures, to see if this will reduce the unwanted premature dissolution of the membrane.

The existence of a nictitating membrane in a rabbit eye may cause mechanical friction to the bandage contact lens, especially to the one for corneal surface use with a smaller diameter. This mechanical friction and movement generated by the nictitating membrane, which is not present in human eyes, could make the wear of bandage contact lens impossible. If this were the case, we will excise the nictitating membrane ahead of time before insertion of a bandage contact lens.

It has been reported that human amniotic membrane may elicit in rabbits xenograft inflammatory reactions mediated by lymphocytes, especially after two weeks after transplanting to the conjunctival surface as a graft with sutures (31;32). If this became our concern, we will verify it by histological examination of the residual membrane, and switch to the use of rabbit amniotic membrane when bandage contact lens is to be tested for a longer period of wear in rabbits.

Key Methods

1. Preparation of Amniotic Membrane:

Human amniotic membrane for research use will be procured according to an IRB protocol (# 01/554A) approved by the Medical Science Subcommittee for the Protection of Human Subjects in Research of the University of Miami School of Medicine on Feb. 1, 2002.), and prepared according to the patented procedure (See U.S. Pat. No. 6,152,142, the teachings of which are incorporated herein by reference.) established by Bio-Tissue using its proprietary method. The confidentiality of the donor information is kept by Bio-Tissue and not disclosed to any personnel involved in this grant proposal and will not be used in any report generated from this study.

As stated in Potential Problems of Aim 3, if rabbit amniotic membrane will have to be used for testing, it will be procured under an IACUC-approved protocol (UM ACUC#00-127renewal03), and prepared in an identical manner to that described for human amniotic membrane. Both human and rabbit amniotic membrane will be processed and prepared for this proposal at the laboratory facility in Bio-Tissue, Inc.

2. Limbal Explant Culture on Amniotic Membrane:

The method is used to test the physiological action of amniotic membrane when such a testing becomes necessary, and has been reported in our previous publications (33-35). In brief, limbal explants will be obtained from the corneoscleral remnant of each donor cornea after being trephined for conventional corneal transplantation. Explants of 1 to 2 mm$^3$ including 0.5 mm within the limbus and 0.5 mm beyond the limbus will be prepared and placed in a culture dish and incubated in Dispase II (1.2 U/ml in Mg$^{2+}$- and Ca$^{2+}$-free Hank's balanced salt solution (HBSS)) for 15 to 30 min at 37° C. under humidified 5% $CO_2$ and rinsed with DMEM containing 10% FBS. The solid support with fastened amniotic membrane with or without additional cryopreservation will be used as a substrate with the basement membrane surface facing up to culture the limbal explant, which will be placed at the center of the membrane with one drop of FBS overnight to allow adequate adhesion, and then cultured in a medium of equal volume of HEPES-buffered DMEM containing bicarbonate and Ham's F12 supplemented with 0.5% dimethyl sulfoxide, 2 ng/ml mouse EGF, 5 mg/ml insulin, 5 mg/ml transferrin, 5 ng/ml selenium, 0.5 mg/ml hydrocortisone, 30 ng/ml cholera toxin A subunit, 5% FBS, 50 mg/ml gentamicin, and 1.25 mg/ml amphotericin B (collectively, termed the SHEM medium). The cultures will be incubated at 37° C. under 5% $CO_2$ and 95% air and the medium will be changed every 2-3 days.

Human limbal tissue will be obtained from the Florida Lion's Eye Bank from cadaver donors whose identity cannot be identified. Human preserved amniotic membrane will be procured according to an IRB-approved protocol (# 01/554A) and processed by Bio-Tissue, while the living donor's identity cannot be identified.

Vertebrate Animals

This animal protocol has been approved by University of Miami (No. 02-142 on Jul. 11, 2002). The major animal to be used is the rabbit. This animal is chosen because of its size and easy manipulation of lens insertion. An extensive Medline, Agricola, and Altweb search showed references matched to following keywords: amniotic membrane, contact lens, ocular surface, and animals, but they are not related to our topic. Therefore, rabbits are the best animal used in the pre-clinical safety testing of the bandage contact lens described in Aim 3.

A total of 25 New Zealand white rabbits (and additional 2 used for possible attrition), either sex with body weight of 2-3 Kg will be used. They will be housed in filter-covered cages under temperature-, humidity-, and light- (12 h light cycle; lights on at 7.00 AM) controlled conditions, and kept on standard chow and water ad libitum.

One rabbit each will be used to test if the lens wear will be interfered by the presence of the nictitating membrane for each design of two types of bandage contact lens, i.e., for corneal and ocular surface uses, respectively. So a total of four rabbits will be needed. One rabbit will be used a control without being tested for lens wear. Additional 20 rabbits will be subdivided into four groups with 5 each to test two different designs of bandage contact lens for corneal and ocular surface uses, respectively. This is a safety study, and not to be used to compared among these four different groups.

The insertion of bandage contact lens will follow the same manner as insertion of contact lens in human patients. This will follow topical application of one drop of 0.5% proparacaine (local anesthetics used in human eyes). Casual daily examination will be performed by hand light or slit lamp without anesthesia. However, if a detailed slit examination is determined to be essential to know the lens wear condition, each rabbit will receive intramuscular injections of 35 mg/kg ketamine, 5 mg/kg xylazine, and 0.75 mg/kg acepromazine.

If there is adverse reaction to the wear of bandage contact lens that warrants euthanasia, this will be conducted by intravenous injection of an overdose of pentobarbital, a method consistent with the recommendation of Panel on Euthanasia of the American Veterinary Medical Association under the approved protocol, ACUC #_02-142. We will continue to conform to the PHS policy on Humane Care and Use of Laboratory Animals, as revised in September 1986.

The following literature may be useful background reading for physicians and clinical investigators.

Literature Cited

1. Kim J C, Tseng S CG. Transplantation of preserved human amniotic membrane for surface reconstruction in severely damaged rabbit corneas. *Cornea* 1995; 14:473-84.
2. Dua H S, Azuara-Blanco A. Amniotic membrane transplantation. *Br J Ophthalmol* 1999;83:748-52.
3. Kruse F E, Rohrschneider K, Voelcker H E. Transplantation von amnio-membran zur rekonstruktion der hornhautoberfläche. *Ophthalmologe* 1999;96:673-8.
4. Sippel K C, Ma J J K, Foster C S. Amniotic membrane surgery. *Curr Opin Ophthalmol* 2001; 12:269-81.
5. Tseng S C G, Tsubota K. Amniotic Membrane Transplantation for Ocular Surface Reconstruction. In: Holland E J, Mannis M J, eds. *Ocular Surface Disease*, 1st ed. NY, Berlin, Heidelberg: Springer, 2002; chap. 20.
6. Kruse F E, Joussen A M, Rohrschneider K, et al. Cryoperserved human amniotic membrane for ocular surface reconstruction. *Graefe's Arch Clin Exp Ophthalmol* 2000; 238:68-75.
7. Trelford J D, Trelford-Sauder M. The amnion in surgery, past and present. *Am J Obstet Gynecol* 1979;134:833-45.
8. de Rotth A. Plastic repair of conjunctival defects with fetal membrane. *Arch Ophthalmol* 1940;23:522-5.
9. Brown A L. Lime burns of the eye: Use of rabbit peritoneum to prevent severe delayed effects. *Arch Ophthalmol* 1941;26:754-69.
10. Sorsby A, Symons H M. Amniotic membrane grafts in caustic burns of the eye. *Br J Ophthalmol* 1946;30:337-45.
11. Sorsby A, Haythorne J, Reed H. Further experience with amniotic membrane grafts in caustic burns of the eye. *Br J Ophthalmol* 1947;31:409-18.

12. Koizumi N, Inatomi T, Sotozono C, et al. Growth factor mRNA and protein in preserved human amniotic membrane. *Curr Eye Res* 2000;20:173-7.
13. Hao Y, Ma D H-K, Hwang D G, et al. Identification of antiangiogenic and antiinflammatory proteins in human amniotic membrane. *Cornea* 2000; 19:348-52.
14. Na B K, Hwang J H, Kim J C, et al. Analysis of human amniotic membrane components as proteinase inhibitors for development of therapeutic agent of recalcitrant keratitis. *Trophoblast Res* 1999; 13:459-66.
15. Solomon A, Rosenblatt M, Monroy D C, et al. Suppression of Interleukin-1a and Interleukin-1b in the human corneal epithelial cells cultured on the amniotic membrane matrix. *Br J Ophthalmol* 2001;85:444-9.
16. Park W C, Tseng S C G. Modulation of acute inflammation and keratocyte death by suturing, blood and amniotic membrane in PRK. *Invest Ophthalmol Vis Sci* 2000;41:2906-14.
17. Wang M X, Gray T B, Parks W C, et al. Corneal haze and apoptosis is reduced by amniotic membrane matrix in excimer laser photoablation in rabbits. *J Cat Refract Surg* 2001; 27:310-9.
18. Kim J S, Kim J C, Na B K, et al. Amniotic membrane patching promotes healing and inhibits protease activity on wound healing following acute corneal alkali burns. *Exp Eye Res* 1998;70:329-37.
19. Shimmura S, Shimazaki J, Ohashi Y, Tsubota K. Antiinflammatory effects of amniotic membrane transplantation in ocular surface disorders. *Cornea* 2001;20:408-13.
20. Heiligenhaus A, Meller D, Meller D, et al. Improvement of HSV-1 necrotizing keratitis with amniotic membrane transplantation. *Invest Ophthalmol Vis Sci* 2001;42: 1969-74.
21. Tseng S C G, Li D-Q, Ma X. Suppression of Transforming Growth Factor isoforms, TGF-b receptor II, and myofibroblast differentiation in cultured human corneal and limbal fibroblasts by amniotic membrane matrix. *J Cell Physiol* 1999;179:325-35.
22. Lee S-B, Li D-Q, Tan D T H, et al. Suppression of TGF-b signaling in both normal conjunctival fibroblasts and pterygial body fibroblasts by amniotic membrane. *Curr Eye Res* 2000;20:325-34.
23. Choi T H, Tseng S C G. In vivo and in vitro demonstration of epithelial cell-induced myofibroblast differentiation of keratocytes and an inhibitory effect by amniotic membrane. *Cornea* 2001;20:197-204.
24. Choi Y S, Kim J Y, Wee W R, Lee J H. Effect of the application of human amniotic membrane on rabbit corneal wound healing after excimer laser photorefractive keratectomy. *Cornea* 1998;17:389-95.
25. Woo H-M, Kim M S, Kweon O-K, et al. Effects of amniotic membrane on epithelial wound healing and stromal remodelling after excimer laser keratectomy in rabbit cornea. *Br J Ophthalmol* 2001;85:345-9.
26. Meller D, Pires R TF, Mack R J S, et al. Amniotic membrane transplantation for acute chemical or thermal burns. *Ophthalmology* 2000;107:980-90.
27. Sridhar M S, Bansal A K, Sangwan V S, Rao G N. Amniotic membrane transplantation in acute chemical and thermal injury. *Am J Ophthalmol* 2000;130:134-7.
28. Kim J C. Use of temporary amniotic membrane graft for corneal diseases. Inaugural Scientific Meeting of Asia Pacific Society of Cornea and Refractive Surgery, 49. 1998.
29. Sridhar M S, Sangwan V S, Bansal A K, Rao G N. Amniotic membrane transplantation in the management of shield ulcers of vernal keratoconjunctivitis. *Ophthalmology* 2001;108:1218-22.
30. Shields C L, Shields J A, Armstrong T. Management of conjunctival and corneal melanoma with surgical excision, amniotic membrane allograft, and topical chemotherapy. *Am J Ophthalmol* 2001; 132:576-8.
31. Kubo M, Sonoda Y, Muramatsu R, Usui M. Immunogenicity of human amniotic membrane in experimental xenotransplantation. Invest Ophthalmol Vis Sci 2001;42: 1539-46.
32. Barton K, Budenz D, Khaw P T, Tseng S C G. Glaucoma filtration surgery using amniotic membrane transplantation. *Invest Ophthalmol Vis Sci* 2001;42:1762-8.
33. Grueterich M, Espana E, Tseng S C. Connexin 43 expression and proliferation of human limbal epithelium on intact and denuded amniotic membrane. *Invest Ophthalmol Vis Sci* 2002;43:63-71.
34. Meller D, Pires R T F, Tseng S C G. Ex vivo preservation and expansion of human limbal epithelial progenitor cells by amniotic membrane. *Br J Ophthalmol* 2002;86:463-71.
35. Grueterich M, Tseng S C G. Human limbal progenitor cells expanded on intact amniotic membrane. *Arch Ophthalmol*. 2002; 120:783-790.
36. John T, Foulks G N, John M E, Cheng K, Hu D. Amniotic membrane in the surgical management of acute toxic epidermal necrolysis. *Ophthalmology* 2002;109:351-60.

Equivalents

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of fastening a membrane to a culture insert comprising:
   a) contacting the membrane with the culture insert;
   b) positioning the membrane on the culture insert, thereby completely covering the culture insert with the membrane;
   c) placing a radially elastic band over the apex of a conical shaped expander having an apex, a base, and an outer surface of increasing diameter from the apex towards the base thereof, the base having a shoulder;
   d) placing the base of said expander in contact with a ring having a peripheral annular groove for receiving said band;
   e) urging said band in a direction from the apex of said expander over the outer surface of said expander towards the shoulder of the base of said expander, thereby causing said band to stretch and form a radially expanded state;
   f) urging said band over the shoulder of said expander and into the peripheral annular groove on the ring, thereby controllably releasing said band from said expander and attaching said band to the ring;
   g) contacting the ring having said band attached thereto with the membrane on the insert; and
   h) controllably releasing the band from the ring such that the band is translocated from the ring to the insert, thereby fastening the band over the membrane and fastening the membrane to the insert.

2. The method of claim 1, wherein the membrane comprises an amniotic membrane.

3. The method of claim 1, wherein the membrane comprises a biocompatible material.

4. The method of claim 1, wherein urging said band over the outer surface of said expander is carried out by:
   a) contacting said band placed over the apex of said expander with an apparatus comprising:
      a longitudinally extending cannula having a proximal end portion and a distal end portion, said cannula defining a bore extending longitudinally therethrough from said proximal end portion to said distal end portion, and said cannula fitting coaxially over the apex of said expander and radially expandable at said distal end portion;
   b) frictionally engaging said band with said distal end portion of said cannula; and
   c) biasing said band over the outer surface of said expander by advancing the cannula towards the base of said expander.

5. The method of claim 4, wherein said expander defines a rod-receiving space having a first diameter and extending longitudinally from the apex of said expander at least partially through said expander towards the base of said expander; and
   wherein said cannula further comprises a rod extending through the bore of said cannula, the rod having a second diameter that is less than the first diameter, the rod fitting coaxially in the rod-receiving space of said expander to frictionally engage said expander and act as a stop to control the movement of said cannula when said cannula is fitted coaxially over the apex of said expander and advanced towards the base of said expander.

6. The method of claim 4, wherein said cannula has a first shape which is substantially cylindrical when not subjected to mechanical stress, and a second shape in which said distal end portion is substantially a radial flange when subjected to mechanical stress in a direction perpendicular to the axis of the cannula.

7. The method of claim 6, wherein said distal end portion of said cannula comprises a plurality of segments defined by a plurality of longitudinally cut slits therein, the segments having a body portion and an end portion, and wherein as the cannula is advanced over the surface of said expander towards the base of said expander the segments thereof are splayed outwardly in a radial direction, thereby forming the radial flange, and wherein the end portion of the segments are capable of frictionally engaging the radially elastic band placed over the apex of said expander.

8. A method of fastening a membrane to a ring having an inner surface defining a hole and having at least one annular groove sized to receive an O-ring, the method comprising:
   a) contacting the membrane to be fastened with the ring;
   b) positioning the membrane on the ring, thereby completely covering the ring with the membrane; and
   c) inserting the O-ring into the annular groove, thereby fastening the membrane to the ring, wherein the annular groove is located on the inner surface of the ring.

9. The method of claim 8, wherein there are at least two annular grooves.

10. A method of fastening a membrane between an O-ring having an outer peripheral annular surface and a ring having an inner annular surface defining a hole and having at least one annular groove, the method comprising:
   a) contacting the membrane to be fastened with the O-ring;
   b) positioning the membrane on the O-ring, thereby completely covering the O-ring with the membrane;
   c) wrapping the membrane over the outer peripheral annular surface of the O-ring to form a wrapped O-ring; and
   d) inserting the wrapped O-ring into the annular groove, thereby fastening the membrane between the O-ring and the ring, wherein the annular groove is located on the inner surface of the ring.

11. A method of fastening a membrane between a first snap together ring and a second snap together ring, the first snap together ring comprising a surface including a plurality of spaced fastener posts, and the second snap together ring comprising a surface defining a plurality of spaced fastener post apertures, the method comprising:
   a) contacting the membrane to be fastened with the surface of the first ring;
   b) positioning the membrane on the first ring, thereby completely covering the first ring with the membrane;
   c) positioning the second ring over the first ring for alignment of at least one of the spaced fastener posts with at least one of the spaced fastener post apertures; and
   d) lockingly engaging the first ring with the second ring, thereby fastening the membrane between the first ring and the second ring.

12. The method of claim 11, wherein the membrane fastened between the two snap together rings is a culture insert.

13. The method of claim 11, wherein the membrane comprises an amniotic membrane.

14. The method of claim 11, wherein the membrane comprises a biocompatible material.

15. A method of fastening a membrane to a ring having a peripheral annular surface, and inner annular surface, a top surface and a bottom surface, with at least one surface defining at least one cut slit thereon, the method comprising:
   a) contacting the membrane to be fastened with the ring;
   b) positioning the membrane on the top surface or the bottom surface of the ring, thereby covering the ring with the membrane; and
   c) inserting the membrane into the cut slit, thereby fastening the membrane to the ring.

16. The method of claim 15, wherein the membrane is inserted into the cut slit on the top surface or the bottom surface.

17. The method of claim 15, wherein the membrane is inserted into the cut slit on the peripheral annular surface.

18. The method of claim 15, wherein the fastened membrane is a culture insert.

19. The method of claim 15, wherein the membrane comprises an amniotic membrane.

20. The method of claim 15, wherein the membrane comprises a biocompatible material.

21. A method of preparing a biopolymer covering for a tissue surface comprising:
   a) contacting a biopolymer membrane with the surface of a first snap together ring having an outer annular edge and an outside diameter sized to snap-fit within the inside diameter of a second snap together ring having an inner annular edge;
   b) positioning the membrane on the first snap together ring, thereby completely covering the first ring with the membrane and wrapping the membrane over the outer annular edge of the first snap together ring;
   c) positioning the second snap together ring over the first snap together ring for coaxial alignment; and
   d) lockingly engaging the first snap together ring with the second snap together ring, thereby fastening the membrane between the first snap together ring and the second snap together ring, and preparing a biopolymer covering for a tissue surface.

22. The method of claim 21, wherein the biopolymer membrane is an amniotic membrane.

23. The method of claim 21, wherein the biopolymer membrane comprises at least one cell.

24. The method of claim 23, wherein before contacting the membrane with the surface of the first ring, the cells are grown on the membrane or the cells are attached to the membrane.

25. The method of claim 23 wherein after the membrane is fastened between the first ring and the second ring, the cells are grown on the membrane or the cells are attached to the membrane.

26. The method of claim 23, wherein the cells are pre-engineered for gene therapy.

27. The method of claim 21, wherein the biopolymer membrane, the first ring, and the second ring are each sized for placement on an outer surface of an eye.

28. The method of claim 21, wherein the biopolymer membrane, the first ring, and the second ring are each sized for placement on a tissue surface selected from the group consisting of dermal tissue, gastrointestinal tract tissue, respiratory tract tissue, genital system tissue, urinary system tissue, circulatory system tissue, and bone tissue.

29. The method of claim 21, wherein the first ring and the second ring are biodegradable.

30. The method of claim 21, wherein the outer annular edge of the first ring includes a first gripping surface and the inner annular edge of the second ring includes a second gripping surface.

31. The method of claim 30, wherein the first and second gripping surfaces include a gripping device selected from the group consisting of burs, an area defining fastener post apertures, and fastener posts.

32. The method of claim 29, wherein at least one of the rings comprises a polymer which further includes at least one bioactive molecule.

33. The method of claim 32, wherein the bioactive molecule is a therapeutic substance.

34. A method of preparing an amniotic membrane covering for a tissue surface comprising:
a) applying an adhesive composition to at least one surface of a support having an outside diameter;
b) contacting the adhesive composition on the surface of the support with an amniotic membrane, the membrane having a surface with a diameter greater than the outside diameter of the support;
c) positioning the support on the membrane so that the membrane can be folded inwardly over the support; and
d) folding the membrane inwardly over the support such that the support is covered by the membrane, thereby preparing an amniotic membrane covering for a tissue surface.

35. The method of claim 34, wherein the support is chosen from a ring and a disc.

36. The method of claim 34, wherein the adhesive composition comprises a material chosen from a fibrin sealant and cyanoacrylate.

37. A method of preparing an amniotic membrane covering for a tissue surface comprising:
a) positioning a support having an outside diameter on a center portion of an amniotic membrane having a surface with a diameter greater than the outside diameter of the support;
b) applying an adhesive composition to a portion of the surface of the amniotic membrane that extends beyond the outside diameter of the support; and
c) folding the amniotic membrane inwardly over the support such that the support is covered by the amniotic membrane, thereby preparing an amniotic membrane covering for a tissue surface.

38. The method of claim 37, wherein the support is chosen from a ring and a disc.

39. The method of claim 37, wherein the adhesive composition comprises a material chosen from a fibrin sealant and cyanoacrylate.

40. The method of claim 37, further comprising:
a) positioning the amniotic membrane covering for a tissue surface on a center portion of a second amniotic membrane having a surface with a diameter greater than the outside diameter of said amniotic membrane covering;
b) applying an adhesive composition to a portion of the surface of the second amniotic membrane that extends beyond the outside diameter of said amniotic membrane covering; and
c) folding the second amniotic membrane inwardly over said amniotic membrane covering such that said amniotic membrane covering is covered by the second amniotic membrane, thereby preparing a double-layered amniotic membrane covering for a tissue surface.

41. The method of claim 40, wherein the adhesive composition comprises a material chosen from a fibrin sealant and cyanoacrylate.

42. A method of preparing an amniotic membrane covering for a tissue surface comprising:
a) positioning a support having an outside diameter on a center portion of a stromal side of an amniotic membrane having a surface with a diameter greater than the outside diameter of the support;
b) folding the amniotic membrane inwardly over the support such that the support is covered by the amniotic membrane to form a covered support; and
c) allowing a portion of the stromal side of the folded membrane to adhere to another portion of the stromal side of the membrane, thereby holding the covered support in place and preparing an amniotic membrane covering for a tissue surface.

43. The method of claim 42, wherein the support is chosen from a ring and a disc.

44. The method of claim 42, further comprising:
a) inserting a second support under the covered support; and
b) positioning the second support for contacting at least a portion of the amniotic membrane covering the covered support, thereby securing the amniotic membrane between the covered support and the second support.

45. An apparatus for frictionally engaging a radially elastic band placed over the apex of a conical shaped expander having an apex, a base, and an outer surface of increasing diameter from the apex towards the base thereof, and urging said band in a direction from the apex of said expander over the outer surface of said expander towards the base of said expander, thereby causing said band to stretch and form a radially expanded state; the apparatus comprising: a longitudinally extending cannula having a proximal end portion and a distal end portion, said cannula defining a bore extending longitudinally therethrough from said proximal end portion to said distal end portion, and fitting coaxially over the apex of said expander and radially expandable at said distal end portion, further comprising a rod extending longitudinally through the bore of said cannula from said proximal end portion to said distal end portion, the rod capable of being resiliently biased into coaxial, releasable engagement with a rod-receiving space in said expander, to frictionally engage said expander and act as a stop to control the movement of said cannula when said cannula is fitted coaxially over the apex of said expander and advanced towards the base of said expander.

46. An apparatus for frictionally engaging a radially elastic band placed over the apex of a conical shaped expander having an apex, a base, and an outer surface of increasing diameter from the apex towards the base thereof, and urging said band in a direction from the apex of said expander over the outer surface of said expander towards the base of said expander, thereby causing said band to stretch and form a radially expanded state; the apparatus comprising: a longitudinally extending cannula having a proximal end portion and a distal end portion, said cannula defining a bore extending longitudinally therethrough from said proximal end portion to said distal end portion, and fitting coaxially over the apex of said expander and radially expandable at said distal end portion, wherein said cannula has a first shape which is substantially cylindrical when not subjected to mechanical stress, and a second shape in which said distal end portion is substantially a radial flange when subjected to mechanical stress in a direction perpendicular to the axis of said cannula, wherein said distal end portion of said cannula comprises:
a plurality of segments defined by a plurality of longitudinally cut slits therein, the segments having a body portion and an end portion, the segments capable of being splayed outwardly apart from each other in a radial direction, thereby forming the radial flange as the cannula is advanced over the surface of said expander towards the base of said expander; and
wherein the end portion of the segments are capable of frictionally engaging the radially elastic band placed over the apex of the conical shaped expander.

47. A culture insert comprising:
a ring having an inner surface defining a hole and having at least one annular groove sized to receive an O-ring;
a membrane mounted to the ring, the membrane completely covering the ring; and the O-ring inserted in the annular groove to fasten the membrane to the ring during assembly, wherein the inner surface of the ring defines an annular groove sized to receive the O-ring, and the O-ring is inserted in the annular groove on the inner surface of the ring to fasten the membrane to the ring.

48. A culture insert comprising:
an O-ring having an inner surface defining a hole and an outer peripheral annular surface;
a membrane mounted to the O-ring, the membrane completely covering the O-ring and wrapped over the outer peripheral annular surface thereof to form a wrapped O-ring;
a ring having an inner annular surface defining a hole and having at least one annular groove sized to receive said wrapped O-ring; and
wherein said wrapped O-ring is positioned in the annular groove to fasten the membrane between the O-ring and the ring during assembly, and wherein the annular groove is located on the inner annular surface of the ring.

49. A culture insert comprising:
a first snap together ring having a first surface;
a plurality of spaced fastener posts located on the first surface;
a second snap together ring having a second surface defining a plurality of spaced fastener post apertures thereon, wherein at least one of the apertures is spaced to align with a position of at least one of the posts when the two rings are matingly engaged during assembly; and
a membrane fastened between the two snap together rings.

50. The culture insert of claim 49 wherein the membrane comprises an amniotic membrane.

51. The culture insert of claim 49, wherein the membrane comprises a biocompatible material.

52. A culture insert comprising:
a ring having a peripheral annular surface, an inner annular surface, a top surface and a bottom surface, with at least one surface defining at least one cut slit thereon; and
a membrane positioned on the top surface or the bottom surface of the ring, said membrane covering the ring, and at least a portion of said membrane inserted into the cut slit to thereby fasten the membrane to the ring during assembly.

53. The culture insert of claim 52, wherein the membrane is inserted into the cut slit on the top surface or the bottom surface.

54. The culture insert of claim 52, wherein the membrane is inserted into the cut slit on the peripheral annular surface.

55. The culture insert of claim 52, wherein the membrane comprises an amniotic membrane.

56. The culture insert of claim 52, wherein the membrane comprises a biocompatible material.

57. A tissue surface covering comprising:
a) a first snap together ring having an outer annular edge and an outside diameter;
b) a membrane completely covering the first snap together ring, the membrane wrapped over the outer annular edge of the first snap together ring; and c) a second snap together ring having an inner annular edge and an inside diameter, the inside diameter of the second snap together ring sized to snap-fit over the outside diameter of the first snap together ring, and positioned over the first snap together ring for coaxial alignment therewith; the membrane fastened between the first snap together ring and the second snap together ring by a locking engagement of the first snap together ring with the second snap together ring during assembly of the tissue surface covering.

58. The tissue surface covering of claim 57, wherein the membrane is a biopolymer membrane.

59. The tissue surface covering of claim 57, wherein the membrane is an amniotic membrane.

60. The tissue surface covering of claim 57, wherein the first ring and the second ring are biodegradable.

61. The tissue surface covering of claim 57, wherein at least one of the rings comprises a polymer which further includes at least one bioactive molecule.

62. The tissue surface covering of claim 61, wherein the bioactive molecule is a therapeutic substance.

63. The tissue surface covering of claim 57, wherein the first ring and the second ring comprise a biocompatible material.

64. The tissue surface covering of claim 57, wherein the membrane, the first ring, and the second ring are each sized for placement on a surface of an eye.

65. The tissue surface covering of claim 57, wherein the membrane, the first ring, and the second ring are each sized for placement on a surface of a tissue selected from the group consisting of dermal tissue, gastrointestinal tract tissue, respiratory tract tissue, genital system tissue, urinary system tissue, circulatory system tissue, and bone tissue.

66. The tissue surface covering of claim 57, wherein the outer annular edge of the first ring includes a first gripping surface and the inner annular edge of the second ring includes a second gripping surface.

67. The tissue surface covering of claim 66, wherein the first and second gripping surfaces include a gripping device selected from the group consisting of burs, fastener posts, and an area defining fastener post apertures.

68. The tissue surface covering of claim 66, wherein the first gripping surface includes an area defining fastener post apertures and the second gripping surface includes fastener posts spatially aligned with the fastener post apertures.

69. The tissue surface covering of claim 66, wherein the first gripping surface includes fastener posts and the second gripping surface includes an area defining fastener post apertures spatially aligned with the fastener posts.

70. The tissue surface covering of claim 67, wherein the first or second gripping surface includes fastener posts and the membrane includes an area defining fastener post apertures spatially aligned with the fastener posts to secure the membrane between the first and second gripping surfaces.

71. An amniotic membrane covering for a tissue surface comprising:
   a) a support having an outside diameter;
   b) an adhesive composition applied to at least one surface of the support; and
   c) an amniotic membrane in contact with the adhesive composition, the membrane having a surface with a diameter greater than the outside diameter of the support and folded inwardly over the support during assembly such that the support is covered by the membrane and secured to the membrane by the adhesive composition.

72. The amniotic membrane covering for a tissue surface of claim 71, wherein the adhesive composition comprises a material chosen from a fibrin sealant and cyanoacrvlate.

73. The amniotic membrane covering for a tissue surface of claim 71, wherein the support is biodegradable.

74. The amniotic membrane covering for a tissue surface of claim 71, wherein the support comprises a polymer which further includes at least one bioactive molecule.

75. The amniotic membrane covering for a tissue surface of claim 74, wherein the bioactive molecule is a therapeutic substance.

76. The amniotic membrane covering for a tissue surface of claim 71, wherein the support comprises a biocompatible material.

77. The amniotic membrane covering for a tissue surface of claim 71, wherein the support has a radius of curvature corresponding to a measured base curve of a body tissue which is to be contacted with the amniotic membrane covering for a tissue surface.

78. The amniotic membrane covering for a tissue surface of claim 71, wherein the support has a radius of curvature corresponding to a measured base curve of a cornea which is to be contacted with the amniotic membrane covering for a tissue surface.

79. An amniotic membrane covering for a tissue surface comprising:
   a) a support having an outside diameter;
   b) an amniotic membrane having a surface with a diameter greater than the outside diameter of the support; and
   c) an adhesive composition applied to at least one surface of the membrane for securing the membrane to the support, the membrane folded inwardly over the support such that the support is contacted by the adhesive composition and is covered by the membrane during assembly of the amniotic membrane covering for a tissue surface.

80. The amniotic membrane covering for a tissue surface of claim 77, wherein the support comprises a biocompatible material.

81. The amniotic membrane covering for a tissue surface of claim 71, wherein the support has a radius of curvature corresponding to a measured base curve of a body tissue which is to be contacted with the amniotic membrane covering for a tissue surface.

82. The amniotic membrane covering for a tissue surface of claim 77, wherein the support has a radius of curvature corresponding to a measured base curve of a cornea which is to be contacted with the amniotic membrane covering for a tissue surface.

83. The amniotic membrane covering for a tissue surface of claim 77, wherein the adhesive composition comprises a material chosen from a fibrin sealant and cyanoacrylate.

84. The amniotic membrane covering for a tissue surface of claim 77, wherein the support is biodegradable.

85. The amniotic membrane covering for a tissue surface of claim 79, wherein the support comprises a polymer which further includes at least one bioactive molecule.

86. The amniotic membrane covering for a tissue surface of claim 79, wherein the bioactive molecule is a therapeutic substance.

87. The amniotic membrane covering for a tissue surface of claim 79, further comprising:
   a) a second amniotic membrane having a surface with a diameter greater than the outside diameter of the amniotic membrane covering for a tissue surface;
   b) a second adhesive composition applied to a portion of the surface of the second amniotic membrane that extends beyond the outside diameter of the amniotic membrane covering for a tissue surface when the amniotic membrane covering for a tissue surface is positioned on a center portion of the second amniotic membrane during assembly; and
   c) the second amniotic membrane folded inwardly over the amniotic membrane covering for a tissue surface during assembly such that the amniotic membrane covering for a tissue surface is covered by the second amniotic membrane, thereby making a double-layered amniotic membrane covering for a tissue surface.

88. The double-layered amniotic membrane covering for a tissue surface of claim 87, wherein the second adhesive composition comprises a material chosen from a fibrin sealant and cyanoacrylate.

89. An amniotic membrane covering for a tissue surface comprising:
   a) a support having an outside diameter;
   b) an amniotic membrane having a surface with a diameter greater than the outside diameter of the support, and having a stromal side; and
   c) the support positioned on a center portion of the stromal side of the membrane, the membrane folded inwardly over the support during assembly such that the support is covered by the membrane, and a portion of the stromal side of the folded membrane adheres to another portion of the stromal side of the membrane, thereby holding the support in place.

90. The amniotic membrane covering for a tissue surface of claim 89, wherein the support is chosen from a ring and a disc.

91. The amniotic membrane covering for a tissue surface of claim 89, further comprising:
   a second support positioned under the covered support, the second support in contact with at least a portion of the membrane covering the covered support, thereby securing the membrane between the covered support and the second support during assembly.

92. The amniotic membrane covering for a tissue surface of claim 89, wherein the support is biodegradable.

93. The amniotic membrane covering for a tissue surface of claim 89, wherein the support comprises a polymer which further includes at least one bioactive molecule.

94. The amniotic membrane covering for a tissue surface of claim 93, wherein the bioactive molecule is a therapeutic substance.

95. The amniotic membrane covering for a tissue surface of claim 89, wherein the support comprises a biocompatible material.

96. The amniotic membrane covering for a tissue surface of claim 89, wherein the support has a radius of curvature corresponding to a measured base curve of a body tissue which is to be contacted with the amniotic membrane covering for a tissue surface.

97. The amniotic membrane covering for a tissue surface of claim 89, wherein the support has a radius of curvature corresponding to a measured base curve of a cornea which is to be contacted with the amniotic membrane covering for a tissue surface.

98. The amniotic membrane covering for a tissue surface of claim 78, wherein the tissue surface is an eye.

99. The amniotic membrane covering for a tissue surface of claim 79, wherein the tissue surface is an eye.

100. The amniotic membrane covering for a tissue surface of claim 80, wherein the tissue surface is an eye.

101. A sutureless covering for an ocular surface, the covering comprising: a conformer having an inner surface contoured to contact the ocular surface;

a support member sized to fit in a groove in an edge of the conformer, the support member attached to the conformer by a snap together attachment; and an amniotic membrane fastened between the conformer and the support member.

102. A tissue surface covering according to claim 57 for use as a composition to reduce ocular pain and corneal haze following excimer laser surgery and to improve the success of keratoprosthesis implantation.

103. A covering for an ocular surface according to claim 101, further comprising cells chosen from the group consisting of cells pre-engineered for gene therapy, retinal pigment epithelial cells, epithelial stem cells, limbal stem cells, and limbal epithelial cells.

104. The covering for an ocular surface according to claim 101, wherein the conformer is shaped to fit in a space between an ocular surface and an eyelid.

105. The covering for an ocular surface according to claim 101, wherein the conformer is a symblepharon ring and the support member is chosen from an O-ring and a piece of polymethyl methacrylate skirt.

106. An amniotic membrane covering for a tissue surface according to claim 71 for use as a composition to reduce ocular pain and corneal haze following excimer laser surgery and to improve the success of keratoprosthesis implantation.

107. An amniotic membrane covering for a tissue surface according to claim 79 for use as a composition to reduce ocular pain and corneal haze following excimer laser surgery and to improve the success of keratoprosthesis implantation.

108. An amniotic membrane covering for a tissue surface according to claim 89 for use as a composition to reduce ocular pain and corneal haze following excimer laser surgery and to improve the success of keratoprosthesis implantation.

109. An amniotic membrane covering for a tissue surface according to claim 101 for use as a composition to reduce ocular pain and corneal haze following excimer laser surgery and to improve the success of keratoprosthesis implantation.

* * * * *